(12) United States Patent
Guo et al.

(10) Patent No.: US 9,107,942 B2
(45) Date of Patent: Aug. 18, 2015

(54) METHODS OF DIAGNOSING AND TREATING FIBROSIS

(75) Inventors: Jia Guo, Pittsford, NY (US); Xin Lin, Rochester, NY (US); Steve Georas, Rochester, NY (US); Patricia Sime, Pittsford, NY (US)

(73) Assignee: University of Rochester, Rochester, NY (US)

(*) Notice: Subject to any disclaimer, the term of this patent is extended or adjusted under 35 U.S.C. 154(b) by 757 days.

(21) Appl. No.: 13/126,875

(22) PCT Filed: Nov. 2, 2009

(86) PCT No.: PCT/US2009/063016
§ 371 (c)(1),
(2), (4) Date: Jul. 25, 2011

(87) PCT Pub. No.: WO2010/051550
PCT Pub. Date: May 6, 2010

(65) Prior Publication Data
US 2011/0286990 A1 Nov. 24, 2011

Related U.S. Application Data

(60) Provisional application No. 61/110,267, filed on Oct. 31, 2008.

(51) Int. Cl.
*A61K 45/00* (2006.01)
*A61K 31/7088* (2006.01)
*A61K 39/395* (2006.01)
*C12Q 1/68* (2006.01)

(52) U.S. Cl.
CPC .......... *A61K 45/00* (2013.01); *A61K 31/7088* (2013.01); *A61K 39/395* (2013.01); *A61K 39/39533* (2013.01); *A61K 39/39583* (2013.01); *C12Q 1/6883* (2013.01); *C12Q 2600/136* (2013.01); *C12Q 2600/154* (2013.01); *C12Q 2600/158* (2013.01)

(58) Field of Classification Search
None
See application file for complete search history.

(56) References Cited

U.S. PATENT DOCUMENTS

2004/0254220 A1* 12/2004 Bressi et al. ............... 514/326
2005/0059682 A1 3/2005 Rubinfeld
2005/0159382 A1 7/2005 McSwiggen et al.
2006/0003958 A1 1/2006 Melville et al.
2006/0257403 A1 11/2006 Young et al.

OTHER PUBLICATIONS

Vire, E et al. The polycomb group protein EZH2 directly controls DNA methylation. Nature. Feb. 16, 2006. 439: 871-874 and Corrigendum.*

Yung, GL et al. Outpatient inhaled nitric oxide in a patient with idiopathic pulmonary fibrosis: a bridge to lung transplantation. The Journal of Heart and Lung Transplantation. 2001. 20(11): 1224-1227. Abstract only.*
Hongo, F et al. Inhibition of the transcription factor Ying Yang 1 activity by S-nitrosation. Biochemical and Biophysical Research Communications. 2005. 336: 692-701.*
Agger et al., "UTX and JMJD3 Are Histone H3K27 Demethylases Involved in HOX Gene Regulation and Development," Nature 449:731-34, Supplemental Information (2007).
Baritaki et al., "Inhibition of Yin Yang 1-Dependent Repressor Activity of DR5 Transcription and Expression by the Novel Proteasome Inhibitor NPI-0052 Contributes to Its TRAIL—Enhanced Apoptosis in Cancer Cells," J. Immunol. 180:6199-210 (2008).
Burgess et al., "PPAR-Gamma Agonists Inhibit TGF-Beta Induced Pulmonary Myofibroblast Differentiation and Collagen Production: Implications for Therapy of Lung Fibrosis," Am. J. Physiol. Lung Cell Mol. Physiol. 288:L1146-L1153 (2005).
Lin et al., "Yin Yang 1 Is a Novel Regulator of Pulmonary Fibrosis," Am. J. Respir. Crit. Care Med. 183:1689-97 (2011) (Epub. Dec. 17, 2010).
Martinez-Chantar et al., "Loss of the Glycine N-Methyltransferase Gene Leads to Steatosis and Hepatocellular Carcinoma in Mice," Hepatology 47:1191-99 (2008).
Moeller et al., "The Bleomycin Animal Model: A Useful Tool to Investigate Treatment Options for Idiopathic Pulmonary Fibrosis?" Int'l J. Biochem. Cell Biol. 40:362-82 (2008) (Epub. Aug. 30, 2007).
Vega et al., "Rituximab-Induced Inhibition of YY1 and Bcl-xL Expression in Ramos Non-Hodgkin's Lymphoma Cell Line via Inhibition of NF-{kappa}B Activity: Role of YY1 and Bcl-xL in Fas Resistance and Chemoresistance, Respectively," J. Immunol. 175:2174-83 (2005).
International Search Report, PCT/US09/63016 (Mar. 2, 2010).
Written Opinion of the International Searching Authority, PCT/US09/63016 (Mar. 2, 2010).
Delgado-Olguin et al., "Epigenetic Repression of Cardiac Progenitor Gene Expression by Ezh2 Is Required for Postnatal Cardiac Homeostasis," Nature Genetics 44(3):343-348 (2012).
Vella et al., "Ezh2 Down-Regulation Exacerbates Lipid Accumulation and Inflammation in in Vitro and in Vivo NAFLD," Int. J. Mol. Sci. 14:24154-24168 (2013).
Zeybel et al., AASLD Abstract No. 1216, "DZNep Attenuates Liver Fibrosis by Blocking EZH2 and H3K27me3," Hepatology 56(4 Supp. 1):772A (2012).
International Preliminary Report on Patentability for PCT/US2009/063016 (May 3, 2011).

* cited by examiner

*Primary Examiner* — Allison Fox
*Assistant Examiner* — Susan E Fernandez
(74) *Attorney, Agent, or Firm* — LeClairRyan, a Professional Corporation

(57) ABSTRACT

The present invention is directed to methods of diagnosing and treating a fibrotic condition in a mammalian subject. These methods involve measuring the levels of trimethylation at lysine residue 27 of histone-3 and/or measuring the expression levels of EZH2 or YY-1. Agents useful for treating fibrosis or a fibrotic condition are also disclosed.

5 Claims, 22 Drawing Sheets

Human lung fibroblast (WI38) 1/9/08

SEQUENCE LISTING

```
<160> NUMBER OF SEQ ID NOS: 28

<210> SEQ ID NO 1
<211> LENGTH: 48
<212> TYPE: DNA
<213> ORGANISM: Artificial
<220> FEATURE:
<223> OTHER INFORMATION: shRNA for inhibiting YY-1 expression

<400> SEQUENCE: 1
cgacggttgt aataagaagt tctcgagaac ttcttattac aaccgtcg                 48

<210> SEQ ID NO 2
<211> LENGTH: 48
<212> TYPE: DNA
<213> ORGANISM: Artificial
<220> FEATURE:
<223> OTHER INFORMATION: shRNA for inhibiting YY-1 expression

<400> SEQUENCE: 2
ccctaagcaa ctggcagaat tctcgagaat tctgccagtt gcttaggg                 48

<210> SEQ ID NO 3
<211> LENGTH: 48
<212> TYPE: DNA
<213> ORGANISM: Artificial
<220> FEATURE:
<223> OTHER INFORMATION: shRNA for inhibiting YY-1 expression

<400> SEQUENCE: 3
gtggttgaag agcagatcat tctcgagaat gatctgctct tcaaccac                 48

<210> SEQ ID NO 4
<211> LENGTH: 48
<212> TYPE: DNA
<213> ORGANISM: Artificial
<220> FEATURE:
<223> OTHER INFORMATION: shRNA for inhibiting YY-1 expression

<400> SEQUENCE: 4
cacatcttaa cacacgctaa actcgagttt agcgtgtgtt aagatgtg                 48

<210> SEQ ID NO 5
<211> LENGTH: 48
<212> TYPE: DNA
<213> ORGANISM: Artificial
<220> FEATURE:
<223> OTHER INFORMATION: shRNA for inhibiting YY-1 expression

<400> SEQUENCE: 5
gccctcataa aggctgcaca actcgagttg tgcagccttt atgagggc                 48

<210> SEQ ID NO 6
<211> LENGTH: 63
<212> TYPE: DNA
```

-continued

```
<213> ORGANISM: Artificial
<220> FEATURE:
<223> OTHER INFORMATION: shRNA for inhibiting YY-1 expression

<400> SEQUENCE: 6
ccctcctgat tattcagaat attagtgaag ccacagatgt aatattctga ataatcagga    60
ggt                                                                  63

<210> SEQ ID NO 7
<211> LENGTH: 20
<212> TYPE: DNA
<213> ORGANISM: Artificial
<220> FEATURE:
<223> OTHER INFORMATION: Oligonucleotide primer

<400> SEQUENCE: 7
actgcccatt gcccaaacac                                                20

<210> SEQ ID NO 8
<211> LENGTH: 24
<212> TYPE: DNA
<213> ORGANISM: Artificial
<220> FEATURE:
<223> OTHER INFORMATION: Oligonucleotide primer

<400> SEQUENCE: 8
gatggtctcc acctcgatct catg                                           24

<210> SEQ ID NO 9
<211> LENGTH: 20
<212> TYPE: DNA
<213> ORGANISM: Artificial
<220> FEATURE:
<223> OTHER INFORMATION: Oligonucleotide primer

<400> SEQUENCE: 9
acgctggtca ccgtggcggc                                                20

<210> SEQ ID NO 10
<211> LENGTH: 20
<212> TYPE: DNA
<213> ORGANISM: Artificial
<220> FEATURE:
<223> OTHER INFORMATION: Oligonucleotide primer

<400> SEQUENCE: 10
ttgccgctct tcttgccgcc                                                20

<210> SEQ ID NO 11
<211> LENGTH: 24
<212> TYPE: DNA
<213> ORGANISM: Artificial
<220> FEATURE:
<223> OTHER INFORMATION: Oligonucleotide primer

<400> SEQUENCE: 11
catgccatca tgcgtctgga cttg                                           24

<210> SEQ ID NO 12
<211> LENGTH: 22
<212> TYPE: DNA
<213> ORGANISM: Artificial
<220> FEATURE:
<223> OTHER INFORMATION: Oligonucleotide primer

<400> SEQUENCE: 12
```

```
acgaaggaat agccacgctc ag                                          22

<210> SEQ ID NO 13
<211> LENGTH: 24
<212> TYPE: DNA
<213> ORGANISM: Artificial
<220> FEATURE:
<223> OTHER INFORMATION: Oligonucleotide primer

<400> SEQUENCE: 13
tgccaatggt gctcctggta ttgc                                        24

<210> SEQ ID NO 14
<211> LENGTH: 22
<212> TYPE: DNA
<213> ORGANISM: Artificial
<220> FEATURE:
<223> OTHER INFORMATION: Oligonucleotide primer

<400> SEQUENCE: 14
gagcaccagg ttcaccactg tt                                          22

<210> SEQ ID NO 15
<211> LENGTH: 21
<212> TYPE: DNA
<213> ORGANISM: Artificial
<220> FEATURE:
<223> OTHER INFORMATION: Oligonucleotide primer

<400> SEQUENCE: 15
gccacccaga agactgtgga t                                           21

<210> SEQ ID NO 16
<211> LENGTH: 20
<212> TYPE: DNA
<213> ORGANISM: Artificial
<220> FEATURE:
<223> OTHER INFORMATION: Oligonucleotide primer

<400> SEQUENCE: 16
gaaggccatg ccagtgagct                                             20

<210> SEQ ID NO 17
<211> LENGTH: 28
<212> TYPE: DNA
<213> ORGANISM: Artificial
<220> FEATURE:
<223> OTHER INFORMATION: Oligonucleotide primer

<400> SEQUENCE: 17
cccgctcgag atggtcctta atcatgct                                    28

<210> SEQ ID NO 18
<211> LENGTH: 29
<212> TYPE: DNA
<213> ORGANISM: Artificial
<220> FEATURE:
<223> OTHER INFORMATION: Oligonucleotide primer

<400> SEQUENCE: 18
cccaagcttc ttaccctgac agcgactgg                                   29

<210> SEQ ID NO 19
<211> LENGTH: 58
<212> TYPE: DNA
```

```
<213> ORGANISM: Artificial
<220> FEATURE:
<223> OTHER INFORMATION: shRNA

<400> SEQUENCE: 19
ccgggcagct gccagatagc atgaactcga gttcatgcta tctggcagct gctttttg      58

<210> SEQ ID NO 20
<211> LENGTH: 58
<212> TYPE: DNA
<213> ORGANISM: Artificial
<220> FEATURE:
<223> OTHER INFORMATION: shRNA

<400> SEQUENCE: 20
aattcaaaaa gcagctgcca gatagcatga actcgagttc atgctatctg gcagctgc      58

<210> SEQ ID NO 21
<211> LENGTH: 54
<212> TYPE: DNA
<213> ORGANISM: Artificial
<220> FEATURE:
<223> OTHER INFORMATION: shRNA

<400> SEQUENCE: 21
ccggcgtacg cggaatactt cgactcgagt cgaagtattc cgcgtacgtt tttg          54

<210> SEQ ID NO 22
<211> LENGTH: 54
<212> TYPE: DNA
<213> ORGANISM: Artificial
<220> FEATURE:
<223> OTHER INFORMATION: shRNA

<400> SEQUENCE: 22
caaaaacgta cgcggaatac ttcgactcga gtcgaagtat tccgcgtacg ccgg          54

<210> SEQ ID NO 23
<211> LENGTH: 58
<212> TYPE: DNA
<213> ORGANISM: Artificial
<220> FEATURE:
<223> OTHER INFORMATION: shRNA for inhibiting YY-1 expression

<400> SEQUENCE: 23
ccgggccctc ataaaggctg cacaactcga gttgtgcagc ctttatgagg gctttttg      58

<210> SEQ ID NO 24
<211> LENGTH: 58
<212> TYPE: DNA
<213> ORGANISM: Artificial
<220> FEATURE:
<223> OTHER INFORMATION: shRNA for inhibiting YY-1 expression

<400> SEQUENCE: 24
caaaaagccc tcataaaggc tgcacaactc gagttgtgca gcctttatga gggcccgg      58

<210> SEQ ID NO 25
<211> LENGTH: 58
<212> TYPE: DNA
<213> ORGANISM: Artificial
<220> FEATURE:
<223> OTHER INFORMATION: shRNA for inhibiting YY-1 expression

<400> SEQUENCE: 25
ccgggtggtt gaagagcaga tcattctcga gaatgatctg ctcttcaacc acttttg       58
```

```
<210> SEQ ID NO 26
<211> LENGTH: 58
<212> TYPE: DNA
<213> ORGANISM: Artificial
<220> FEATURE:
<223> OTHER INFORMATION: shRNA for inhibiting YY-1 expression

<400> SEQUENCE: 26
caaaaagtgg ttgaagagca gatcattctc gagaatgatc tgctcttcaa ccacccgg        58

<210> SEQ ID NO 27
<211> LENGTH: 30
<212> TYPE: DNA
<213> ORGANISM: Artificial
<220> FEATURE:
<223> OTHER INFORMATION: DNA probe

<400> SEQUENCE: 27
tcagttcctg gtttcattac tacaacacaa                                       30

<210> SEQ ID NO 28
<211> LENGTH: 30
<212> TYPE: DNA
<213> ORGANISM: Artificial
<220> FEATURE:
<223> OTHER INFORMATION: DNA probe

<400> SEQUENCE: 28
ttgtgttgta gtaatgaaac caggaacaga                                       30
```

METHODS OF DIAGNOSING AND TREATING FIBROSIS

This application is a U.S. national stage entry under 35 U.S.C. 371 of International Patent Application No. PCT/US2009/063016, filed Nov. 2, 2009, which claims the benefit of U.S. Provisional Patent Application Ser. No. 61/110,267, filed Oct. 31, 2008, which is hereby incorporated by reference in its entirety.

This invention was made with government support under grant number R01 HL073952 awarded by the National Institutes of Health. The government has certain rights in this invention.

FIELD OF THE INVENTION

The present invention is directed to methods of diagnosing and treating a fibrotic condition in a mammalian subject.

BACKGROUND OF THE INVENTION

Idiopathic pulmonary fibrosis (IPF) is a progressive, chronic interstitial lung disease associated with high mortality (median survival of newly diagnosed patients is ~3 years) and a uniformly poor prognosis (Khalil et al., "Idiopathic Pulmonary Fibrosis: Current Understanding of the Pathogenesis and the Status of Treatment," *CMAJ* 171(2):153-60 (2004)). IPF is the pathological hallmark of interstitial lung diseases (Green, F. H., "Overview of Pulmonary Fibrosis," *Chest* 122(6 Suppl):334S-339S (2002)) and is characterized by increased deposition of extracellular matrix (ECM), including collagen. This lethal lung disorder presents a major clinical challenge, since effective therapeutic agents for reversing lung fibrosis have not yet been discovered (Phan et al., "The Myofibroblast as an Inflammatory Cell in Pulmonary Fibrosis," *Curr. Top. Pathol.* 93:173-82 (1999)). The current hypothesis is that IPF represents a chronic injury/repair response to specific environmental insults (such as silica or asbestos). However, the precise molecular mechanisms underlying persistent fibroblast activation remains poorly understood. Myofibroblasts are now recognized as major effector cells in pulmonary fibrosis. They are characterized by the expression of α-smooth muscle actin (α-SMA), enhanced proliferation, and synthesis of ECM proteins (Sheppard et al., "Transcriptional Activation by NF-κB Requires Multiple Coactivators," *Mol. Cell. Biol.* 19(9):6367-78 (1999)), and are thought to be derived from fibroblasts via the activity of TGF-β and other stimuli (Roy et al., "Regulation of α-Smooth Muscle Actin Gene Expression in Myofibroblast Differentiation from Rat Lung Fibroblasts," *Int'l J. Biochem. Cell Biol.* 33(7):723-34 (2001)). In pulmonary fibrosis, myofibroblasts acquire resistance to apoptosis, which may account for the increased number of these cells present in fibroblastic foci (Horowitz et al., "Combinatorial Activation of FAK and AKT by Transforming Growth Factor-β1 Confers an Anoikis-Resistant Phenotype to Myofibroblasts," *Cell Sign.* 19(4):761-71 (2007)).

Myofibroblasts are crucial effector cells in lung fibrosis, and derive from epithelial to mesenchymal transition (EMT) (Bedi et al., "Epithelial-to-Mesenchymal Transition and Chronic Allograft Tubulointerstitial Fibrosis," *Transplant. Rev.* 22(1):1-5 (2008)), circulating fibrocytes (Andersson-Sjoland et al., "Fibrocytes Are a Potential Source of Lung Fibroblasts in Idiopathic Pulmonary Fibrosis," *Int. J. Biochem. Cell Biol.* 40(10):2129-40 (2008)), and by self renewal in response to lung injury or chronic inflammation induced by stimuli such as silica and bleomycin. These myofibroblasts are accumulated in the injured lung and block alveolar gas exchange. Avoiding the formation of over-myofibroblasts would provide protection against lung fibrosis, and this could be achieved by inhibition of α-SMA expression in lung fibroblasts (Meyer-Ter-Vehn et al., "Lovastatin Inhibits TGF-β-Induced Myofibroblast Transdifferentiation in Human Tenon Fibroblasts," *Invest. Ophthalmol. Vis. Sci.* 49(9):3955-60 (2008)).

After inhalation of pro-fibrotic stimuli (e.g. asbestos, silica, bleomycin) alveolar macrophages produce cytokines including TGF-β1 and TNF-α) that contribute to lung inflammation and fibrosis via different mechanisms (Hardie et al., "Conditional Expression of Transforming Growth Factor-α in Adult Mouse Lung Causes Pulmonary Fibrosis," *Am. J. Physiol. Lung Cell. Mol. Physiol.* 286(4):L741-49 (2004); Liu et al., "Transforming Growth Factor-$β_1$ Overexpression in Tumor Necrosis Factor-α Receptor Knockout Mice Induces Fibroproliferative Lung Disease," *Am. J. Respir. Cell Mol. Biol.* 25(1):3-7 (2001)). TGF-$β_1$ plays an essential role in wound healing and matrix molecule deposition. It induces myofibroblast differentiation and alveolar remodeling in vivo (Leask & Abraham, "TGF-β Signaling and the Fibrotic Response," *Faseb. J.* 18(7):816-27 (2004); Lee et al., "Early Growth Response Gene 1-Mediated Apoptosis Is Essential for Transforming Growth Factor $β_1$-Induced Pulmonary Fibrosis," *J. Exp. Med.* 200(3):377-89 (2004)), and overexpression of this potent profibrotic mediator leads to progressive fibrosis in mice, with minimal inflammation (Sime et al., "Adenovector-Mediated Gene Transfer of Active Transforming Growth Factor-β1 Induces Prolonged Severe Fibrosis in Rat Lung," *J. Clin. Invest.* 100(4):768-76 (1997)). TNF-α also contributes to lung fibrosis (Ortiz et al., "Expression of TNF and the Necessity of TNF Receptors in Bleomycin-Induced Lung Injury in Mice," *Exp. Lung Res.* 24(6):721-43 (1998)), and its effects may be mediated through activation of other growth factors. TNF-α may also regulate the balance between cell survival and cell death. For example, TNF-α-deficient mice are protected against bleomycin-induced lung inflammation via reduced apoptosis of inflammatory cells (Kuroki et al., "Repression of Bleomycin-Induced Pneumopathy by TNF," *J. Immunol.* 170(1):567-74 (2003)) Inhibition of TNF-α with infliximab may stabilize the progression of pulmonary fibrosis associated with collagen vascular disease (CVD) (Antoniou et al., "Infliximab Therapy in Pulmonary Fibrosis Associated with Collagen Vascular Disease," *Clin. Exp. Rheumatol.* 25(1):23-28 (2007)).

Yin Yang 1 (YY1) is a ubiquitously expressed zinc finger transcription factor that can either activate or repress gene transcription, and plays an important role in cellular proliferation, differentiation, and apoptosis. Growing evidence indicates that YY1 contributes to the pathogenesis of cancer and inflammation (Austen et al., "Characterization of the Transcriptional Regulator YY1. The Bipartite Transactivation Domain Is Independent of Interaction with the TATA Box-Binding Protein, Transcription Factor IIB, TAFII55, or cAMP-Responsive Element-Binding Protein (CBP)-Binding Protein," *J. Biol. Chem.* 272(3):1709-17 (1997); Gordon et al., "Transcription Factor YY1: Structure, Function, and Therapeutic Implications in Cancer Biology," *Oncogene* 25(8):1125-42 (2006)). For example, YY1 negatively regulates p53, a tumor suppressor gene (Sui et al., "Yin Yang 1 Is a Negative Regulator of p53," *Cell* 117(7):859-72 (2004)), and promotes tumor cell survival in part by preventing apoptosis (Huerta-Yepez et al., "Involvement of the TNF-α Autocrine-Paracrine Loop, via NF-κB and YY1, in the Regulation of Tumor Cell Resistance to Fas-Induced Apoptosis," *Clin. Immunol.* 120(3):297-309 (2006); Vega et al., "Rituximab (Chimeric anti-CD20) Sensitizes B-NHL Cell Lines to Fas-Induced Apoptosis," *Oncogene* 24(55):8114-27 (2005)). TNF-α-induced YY1 represses Fas expression, providing a mechanism whereby YY1 contributes to TNF-α-induced cell survival (Huerta-Yepez et al., "Involvement of the TNF-α Autocrine-Paracrine Loop, via NF-κB and YY1, in the Regulation of Tumor Cell Resistance to Fas-Induced Apoptosis," *Clin. Immunol.* 120(3):297-309 (2006)). In fibroblasts, TNF-α induces YY1 in an NF-κB-dependent manner (Wang et al., "NF-κB Regulation of YY1 Inhibits Skeletal Myogenesis Through Transcriptional Silencing of Myofibrillar Genes," *Mol. Cell Biol.* 27(12):4374-87 (2007)), supporting a link between the NF-κB pathway and YY1 expression (Huerta-Yepez et al., "Involvement of the TNF-α Autocrine-Paracrine Loop, via NF-κB and YY1, in the Regulation of Tumor Cell Resistance to Fas-Induced Apoptosis," *Clin. Immunol.* 120(3):297-309 (2006); Vega et al., "Rituximab (Chimeric anti-CD20) Sensitizes B-NHL Cell Lines to Fas-Induced Apoptosis," *Oncogene* 24(55):8114-27 (2005); Lei et al., "p38 MAPK-Dependent and YY1-Mediated Chemokine Receptors CCR5 and CXCR4 Up-Regulation in U937 Cell Line Infected by *Mycobacterium tuberculosis or Antinobacillus actinomycetemcomitans*," *Biochem. Biophys. Res. Commun.* 329(2):610-15 (2005)). YY1 can bind to and activate type I and type II collagen gene promoters in fibroblasts (Riquet et al., "YY1 Is a Positive Regulator of Transcription of the Colla1 Gene," *J. Biol. Chem.* 276(42):38665-72 (2001); Miao et al., "Identification of Two Repressor Elements in the Mouse $\alpha_2$(I) Collagen Promoter," *Arch. Biochem. Biophys.* 361(1):7-16 (1999)), and also enhance fibronectin gene expression (Du et al., "Transcriptional Up-Regulation of the Delayed Early Gene HRS/SRp40 During Liver Regeneration. Interactions Among YY1, GA-Binding Proteins, and Mitogenic Signals," *J. Biol. Chem.* 273(52):35208-15 (1998)). The expression of cyclooxygenase-2 (which also contributes to lung fibrosis) is also regulated by YY1 in macrophages (Joo et al., "Yin Yang 1 Enhances Cycloxygenase-2 Gene Expression in Macrophages," *Am. J. Physiol. Lung Cell. Mol. Physiol.* 292(5):L1219-26 (2007)). These reports suggest that YY1 may play a role in fibrotic responses in the lung or other organs, but very little is known about the expression or function of YY1 in fibrotic conditions in vivo.

Experiments employing conditional deletion mouse stains revealed a crucial role for YY1 in the proliferation and differentiation of B lymphocytes (Liu et al., "Yin Yang 1 Is a Critical Regulator of B-Cell Development," *Genes Dev.* 21(10):1179-89 (2007)) and oligodendrocytes (He et al., "The Transcription Factor Yin Yang 1 Is Essential for Oligodendrocyte Progenitor Differentiation," *Neuron* 55(2):217-30 (2007)). Embryonic fibroblasts from YY1-deficient mice demonstrated reduced proliferation in vitro in proportion to the levels of YY1 protein expression. This finding indicates that YY1 controls fibroblast proliferation in a gene dosage-dependent manner (Affar el et al., "Essential Dosage-Dependent Functions of the Transcription Factor Yin Yang 1 in Late Embryonic Development and Cell Cycle Progression," *Mol. Cell Biol.* 26(9):3565-81 (2006)). However, very little is known about the expression or function of YY1 in fibrotic conditions or disorders, such as lung fibrosis.

The present invention is directed to overcoming these and other deficiencies in the art.

SUMMARY OF THE INVENTION

A first aspect of the present invention is directed to a method of diagnosing a fibrotic condition in a subject by measuring the level of trimethylation at lysine residue 27 of histone-3 ("H3K27") in a biological sample from the subject. The level of H3K27 trimethylation is compared to a standard level of H3K27 trimethylation, and the presence or absence of a fibrotic condition is correlated to the results of the comparison.

A second aspect of the present invention is directed to a method of diagnosing a fibrotic condition in a subject by measuring the expression level of Enhancer of Zeste Homolog 2 ("EZH2") or Yin-Yang-1 ("YY-1") in a biological sample from the subject. The expression level of EZH2 or YY-1 in the biological sample is compared to a standard expression level of EZH2 or YY-1, and the presence or absence of a fibrotic condition is correlated to the results of the comparison.

Another aspect of the present invention is directed to a method of treating a subject having a fibrotic condition. This method involves administering to the subject an agent that inhibits or reduces H3K27 trimethylation under conditions effective to treat a fibrotic condition in the subject.

Another aspect of the present invention relates to a method of identifying an agent that is effective for treating a fibrotic condition. This method involves obtaining a first biological sample from an in vivo or in vitro experimental model of fibrosis and administering a candidate agent to the experimental model of fibrosis. A second biological sample is obtained from the experimental model after administering the candidate agent, and the level of H3K27 trimethylation in the first and second biological samples is measured. The level of H3K27 trimethylation in the first and second biological samples is then compared. A decrease in the level of H3K27 trimethylation in the second biological sample relative to the level of H3K27 trimethylation in the first biological sample indicates that the agent is effective for treating a fibrotic condition.

Another aspect of the present invention is directed to a pharmaceutical composition. The pharmaceutical composition contains a pharmaceutically acceptable delivery vehicle and an effective amount of one or more agents selected from the group consisting of an agent that inhibits or reduces H3K27 trimethylation, an inhibitor of EZH2, an inhibitor of YY-1, and an inhibitor of histone deacetylase. The pharmaceutical composition of the present invention is suitable for treating a fibrotic condition.

Pulmonary fibrosis, like other fibrotic conditions, is a progressive and chronic condition involving the formation of excess connective scar tissue within the lung. Pulmonary fibrosis alone affects more than five million people worldwide, resulting in more than 40,000 deaths per year. The present invention provides, inter alia, an understanding of the molecular mechanisms underlying the pathogenesis of fibrosis and fibrotic conditions that facilitates the development of early diagnostic markers as well as effective therapeutic agents that can prevent or reduce disease progression.

BRIEF DESCRIPTION OF THE DRAWINGS

FIG. 1A is a series of representative light photomicrographs of lung tissue samples from IPF patients ("IPF") and healthy controls ("Normal") (n=5). Samples in the top panel ("H&E") were stained with hemotoxylin and eosin to identify histological features. H&E staining shows that highly inflammatory lung was found in IPF samples. Immunohistochemistry was used on the samples in the bottom panel ("YY1") to identify the expression of YY1. Pictures were obtained at the original magnification of 10×. The 63× magnification is shown in the upper right-hand corner. FIG. 1B is an immunoblot of whole lung tissue extracts from IPF patients ("IPF") and healthy controls ("Normal"), using anti-YY1 (H414, Santa Cruz) and anti-β-actin antibodies. YY1 expression is upregulated in whole lung tissue lysates of IPF patients. FIG. 1C is a graph showing the relative fold induction of YY-1 mRNA expression in lung tissue derived from IPF subjects ("IPF") compared to lung tissue from healthy controls ("Normal") (n=5), assessed by quantitative PCR. *$p<0.05$ by Student's t-test. YY1 transcription level is upregulated in whole lung tissues of IPF patients.

FIG. 2A is a series of representative light photomicrographs of lung tissue samples from C57BL/6 mice treated with silica ("Silica") or saline ("PBS") (n=5 mice per group). Samples in the top panel ("H&E") were stained with hemotoxylin and eosin to identify histological features. H&E staining shows that highly inflammatory lung was found in silica-induced pulmonary fibrosis. Immunohistochemistry was used on the samples in the bottom panel ("YY1") to identify the expression of YY1. Pictures were obtained at the original magnification of 10×. The 63× magnification is shown in the upper right-hand corner. FIG. 2B is an immunoblot of whole lung tissue extracts from C57BL/6 mice treated with silica ("Silica") or saline ("PBS"), using anti-YY1 (H414, Santa Cruz) and anti-GAPDH antibodies. YY1 expression is upregulated in whole lung tissue lysates of silica-induced fibrosis. FIG. 2C is a graph showing the relative fold induction of YY-1 mRNA expression in the samples shown in FIG. 2A, assessed by quantitative PCR. **$p<0.01$ by Student's t-test. YY1 transcription level is upregulated in whole lung tissues of silica-induced fibrosis.

FIG. 3A is a series of representative light photomicrographs of lung tissue samples from C57BL/6 mice treated with bleomycin ("Bleomycin") or saline ("PBS") (n=5 mice per group). Samples in the top panel ("H&E") were stained with hemotoxylin and eosin to identify histological features. H&E staining shows that highly inflammatory lung was found in bleomycin-induced pulmonary fibrosis. Immunohistochemistry was used on the samples in the bottom panel ("YY1") to identify the expression of YY1. Pictures were obtained at the original magnification of 10×. The 63× magnification is shown in the upper right-hand corner. FIG. 3B is an immunoblot of cytoplasmic and nuclear fractions from C57BL/6 mice treated with the indicated amounts of bleomycin, using anti-YY1 (H414, Santa Cruz) and anti-β-actin antibodies. YY1 expression is upregulated in whole lung tissue lysates of bleomycin-induced fibrosis. FIG. 3C is a graph showing the relative fold induction of YY-1 mRNA expression in the samples shown in FIG. 3A, assessed by quantitative PCR. *$p<0.05$ by Student's t-test. YY1 transcription level is upregulated in whole lung tissues of bleomycin-induced fibrosis.

FIGS. 7A and 7B are immunoblots of human WI-38 cells (FIG. 7A) and mouse MLg2908 cells (FIG. 7B) treated with TGF-β. After serum starvation for 24 hours, cells were treated with 10 ng/ml of TGF-β for the indicated times in serum-free DMEM. Extracts from whole cells were subjected to immunoblot analysis with anti-YY1 or anti-β-actin antibody. FIGS. 7C and 7D are graphs showing the relative fold induction of YY-1 mRNA expression, detected by quantitative PCR, in WI-38 cells (FIG. 7C) and MLg2908 cells (FIG. 7D) treated with TGF-β. FIGS. 7E and 7F are graphs relating to the YY1 promoter activity in YY1-Luc-transfected WI-38 cells (FIG. 7E) and YY1-Luc-transfected MLg2908 cells (FIG. 7F) treated with PBS or TGF-β for 24 hours. The full-length YY1 promoter-luciferase reporter (YY1-LUC) was transfected into the cells by electroporation. Relative light units (RLU) were measured with a luminometer. Fold changes result from the RLU of stimulated cells divided by the RLU of non-stimulated cells. The data are presented with standard errors derived from at least three independent experiments performed in triplicate. *$p<0.05$ and **$p<0.01$ by the Student's t-test.

FIG. 8A is an immunoblot of whole cell extracts from MRC5 cells treated with TGF-β for 8 hours. FIG. 8B is a graph of the relative light units of YY1-Lluc-transfected MRC5 cells treated with phosphate-buffered saline ("0") or TGF-β ("10") for 24 hours. The data are presented with standard errors derived from at least three independent experiments performed in triplicate. *$p<0.05$ by the Student's t-test.

FIGS. 9A and 9B are immunoblots of human WI-38 cells (FIG. 9A) and mouse MLg2908 cells (FIG. 9B) treated with TNF-α. After serum starvation for 24 hours, cells were treated with 10 ng/ml of TNF-α for the indicated times in serum-free DMEM. Extracts from whole cells were subjected to immunoblot analysis with anti-YY1 or anti-β-actin antibody. FIGS. 9C and 9D are graphs showing the relative fold induction of YY-1 mRNA expression, detected by quantitative PCR, in WI-38 cells (FIG. 9C) and MLg2908 cells (FIG. 9D) treated with TGF-β. FIGS. 9E and 9F are graphs relating to the YY1 promoter activity in YY1-Luc-transfected WI-38 cells (FIG. 9E) and YY1-Luc-transfected MLg2908 cells (FIG. 9F) treated with TNF-α for 8 hours. The full-length YY1 promoter-luciferase reporter (YY1-LUC) was transfected into the cells by electroporation. Relative light units (RLU) were measured with a luminometer. Fold changes result from the RLU of stimulated cells divided by the RLU of non-stimulated cells. The data are presented with standard errors derived from at least three independent experiments performed in triplicate. *$p<0.05$, $p<0.01$, and *$p<0.001$ by the Student's t-test.

FIG. 12A is a graph of the relative fold induction of YY1 mRNA expression in WI-38 cells transfected with a wild-type YY1 promoter construct ("YY1"). FIG. 12B is a graph of the relative fold induction of YY1 mRNA expression in WI-38 cells transfected with a mutant YY1 promoter contruct that has a disrupted NF-κB binding site ("mutant YY1"). In both cases, the cells were also transiently co-transfected with a vector control ("pSG5") or 2.5 μg of NF-κB ("p65") plasmid by electroporation, and then treated with PBS or 10 ng/ml of TGF-β for 24 hours. Data are presented with standard errors derived from at least three independent experiments performed in triplicate. ***$P<0.001$ (untreated pSG5 vs. untreated p65; TGF-β-treated pSG5 vs. TGF-β-treated p65). FIG. 12C is an immunoblot of WI-38 cells pre-treated with 5 μM of Bay 11-7085 (an NF-κB inhibitor) for one hour and then treated with 10 ng/ml of TGF-β for the indicated times in serum-free DMEM. Extracts from whole cells were immunoblotted with anti-YY1 or anti-β-actin antibody.

FIG. 13A is a graph of α-SMA activity in WI-38 cells transfected with the mouse α-SMA luciferase reporter (α-SMA-Luc). Cells were also transiently transfected by electroporation with control vector ("pSG5") or 2.5 μg of YY1 ("YY1") and NF-κB ("p65") (alone or in combination) and then treated with PBS or 10 ng/ml of TGF-β for 24 hours. *$p<0.05$, **$p<0.01$. FIG. 13B is an electrophoretic mobility shift assay (EMSA) showing YY1 binding activity at the α-SMA promoter in nuclear extracts isolated from WI-38 cells. EMSA was performed with a biotin-labeled probe containing a known YY1 binding site in the α-SMA promoter. EMSAs with no antibody, control IgG, and YY1 antibody were used to confirm the presence of YY1 binding complexes. FIG. 13C is a graph of α-SMA activity in lung fibroblasts obtained from YY1$^{+/-}$ mice or wide type mice transfected with the mouse α-SMA-Luc by electroporation and then treated with PBS or 10 ng/ml of TGF-β for 24 hours. *$p<0.05$, *$p<0.01$. All reporter data were normalized using an empty vector control. RLU data are shown from at least five independent experiments performed in duplicate.

FIG. 14A is a series of images of lung fibroblasts isolated from YY1$^{CC10}$ and wild type ("WT") mice immunostained with α-SMA (green) and YY1 (red). All pictures are shown at the original magnification of 20× or 40×. FIG. 14B is a western blot of lung fibroblasts derived from two individual YY1$^{CC10}$ mice ("CC10-YY1-1" and "CC10-YY1-2") and two wild type mice ("WT1" and "WT2"). Whole-cell lysates were immunoblotted with anti-YY1, anti-collagen 1, anti-α-SMA, and β-actin antibodies. Representative examples obtained from three independent experiments are shown. FIG. 14C is a series of light photomicrographs of lung samples from YY1$^{CC10}$ and wildtype mice ("Littermate") (n=8 mice per group). Immunohistochemistry was used to compare the α-SMA and collagen expression in the control mice and the YY1$^{CC10}$ mice. Pictures are presented at the original magnification (10×), and a 63× micrograph is shown in the upper right-hand corner.

FIG. 15A is a series of images of lung fibroblasts isolated from YY1$^{f/f}$ mice and then transfected with Cre-GFP vector to knockdown YY1 expression. The fibroblasts were then immunostained with anti-α-SMA (red) antibody ("α-SMA"). The pictures illustrate the original magnification at 40×. FIG. 15B is a western blot showing YY1 protein expression in primary lung fibroblasts obtained from YY1$^{f/f}$ mice and transfected with Lenti-Cre or pLL37 as a control, at the indicated multiplicities of infection ("MOI"). The cells were blotted with anti-YY1 and anti-β-actin antibodies. FIG. 15C is a series of images of LL97A cells transduced with one of two control lentivirus vector shRNAs ("Control-1" and "Control-2") or one of two lentivirus vector YY1 shRNAs ("YY1-lenti-shRNA-1" and "YY1-lenti-shRNA-2") for three days. Puromycin was then used to select transduced cells. The selected LL97A cells were immunostained with anti-α-SMA (green) and anti-YY1 (red) antibodies, or with anti-collagen I (green) and anti-YY1 (red) antibodies. Pictures are presented at the original magnification of 40×. FIG. 15D is a western blot of LL97A cells transduced with the indicated vectors, showing the expression levels of collagen 1 and YY1. Extracts from whole cells were immunoblotted with anti-collagen 1 and anti-YY1 antibodies. Representative examples of three independent experiments are shown.

FIG. 16A is a series of light photomicrographs of lung sections from silica-treated YY1$^{+/-}$ or littermate mice evaluated 21 days after silica treatment (n=6 mice per group). H&E staining and immunohistochemistry were used to compare histological features and the expression of α-SMA and collagen in YY1$^{+/-}$ compared to littermate mice. Pictures are presented at their original magnification of 10× (63× is shown in the right-hand corner). FIG. 16B is a graph of the fibrosis grade-score for the lung tissue sections showin in FIG. 16A, evaluated by double blind scoring using immunohistochemistry for α-SMA. *$p<0.05$ by the Student's t-test. FIG. 16C is a series of light photomicrographs of lung sections obtained from bleomycin-treated YY1$^{f/f}$ mice (F4) or wild type mice evaluated 21 days after bleomycin treatment (n=4 mice per group). H&E staining and immunohistochemistry were used to compare histological features and the expression of α-SMA and YY1 in the YY1$^{f/f}$ mice compared to the wild type control mice. Pictures are shown at their original magnification of 10× (63× is indicated in the upper right-hand corner). FIG. 16D is a graph of the fibrosis grade-score for the lung tissue sections show in FIG. 16C, evaluated by double blind scoring using immunohistochemistry for α-SMA. **p<0.01 by the Student's t-test. All experiments were performed at least 2 times.

FIG. 17A is a series of light photomicrographs, in which H&E staining and immunohistochemistry were used to compare the histological features and the expression of α-SMA and collagen in YY1$^{f/f}$ compared to WT mice. Pictures are presented at their original magnification of 10× (63× is shown in the right-hand corner). FIG. 17B is a graph of the fibrosis grade-score for the lung tissue sections shown in FIG. 17A evaluated by double blind scoring using immunohistochemistry for α-SMA (n=4 mice per group). *p<0.05 by the Student's t-test. FIG. 17C is a graph of the relative fold induction of mRNA YY1 expression in YY1$^{f/f}$ mice versus wildtype mice, evaluated by quantitative PCR. FIG. 17D is a western blot of lung sections obtained from adenoviral Cre- and silica-treated YY1$^{f/f}$ mice ("YY1$^{f/f}$+ad-cre") and wild type mice ("Wild type+ad-cre") (n=3 per group). Lung sections were ground in liquid nitrogen and part of grinded lung for extraction of RNA or lyses for western blot.

DETAILED DESCRIPTION OF THE INVENTION

Figure 1A:
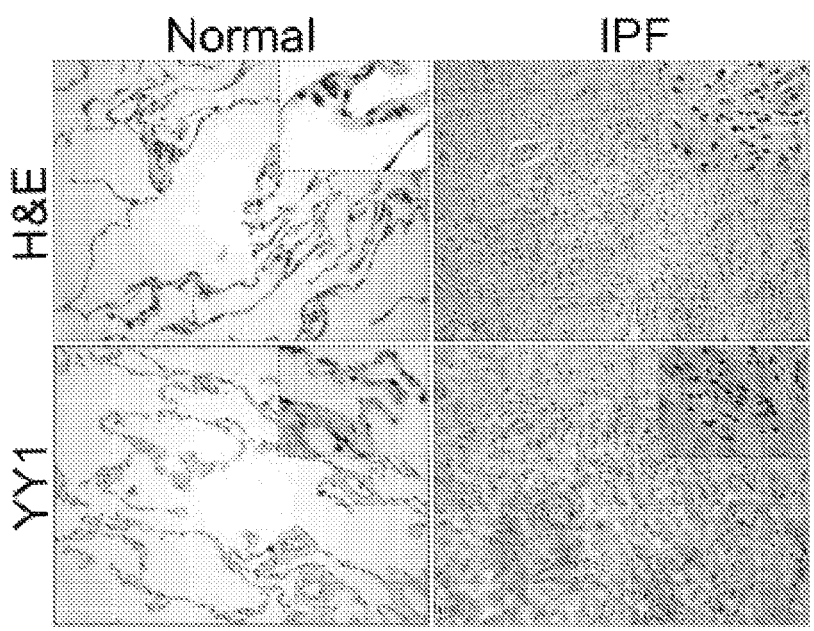
FIGS. 1A-1C show that YY1 protein expression is increased in the lungs of idiopathic pulmonary fibrosis (IPF) patients.

The present invention relates to several methods for diagnosing and treating a fibrotic condition in a subject. The subject can be any animal that exhibits fibrotic processes, preferably a mammalian subject. Exemplary mammalian subjects include, without limitation, humans, non-human primates, dogs, cats, rodents (e.g., mouse, rat, guinea pig), horses, cattle and cows, sheep, and pigs.

A fibrotic condition generally refers to the formation or development of excess fibrous connective tissue in an organ or tissue and resulting disorders/diseases. Fibrosis can affect the lungs, heart, kidneys, liver, brain, skin, or any other organ. Fibrotic conditions that can be diagnosed according to the methods of the present invention include, without limitation, acute and chronic forms of pulmonary fibrosis, interstitial lung disease, human fibrotic lung disease, liver fibrosis, cardiac fibrosis, kidney fibrosis, macular degeneration, retinal and vitreal retinopathy, myocardial fibrosis, Grave's ophthalmopathy, drug induced ergotism, cardiovascular disease, atherosclerosis/restenosis, keloids and hypertrophic scars, cancer, Alzheimer's disease, skin fibrosis, scarring, scleroderma, glioblastoma in Li-Fraumeni syndrome, sporadic glioblastoma, myeloid leukemia, acute myelogenous leukemia, myelodysplastic syndrome, myeloproferative syndrome, gynecological cancer, Kaposi's sarcoma, Hansen's disease and inflammatory bowel disease, including collagenous colitis, ocular scarring, and cataracts.

A first aspect of the present invention is directed to a method of diagnosing a fibrotic condition in a subject by measuring the level of trimethylation at lysine residue 27 of histone-3 ("H3K27") in a biological sample from the subject. The level of H3K27 trimethylation is compared to a standard level of trimethylation at lysine residue 27 of histone-3 and the presence or absence of a fibrotic condition is correlated to the results of the comparison.

Histone 3 is a protein found in association with DNA in the chromation of eukaryote cells. The full-length amino acid sequences of human and mouse histone-3 (H3) proteins are well known in the art (see GenBank Accession Nos. NM_0003493 (human) and NM_030082 (mouse), which are hereby incorporated by reference in their entirety). As shown herein, an increase in H3K27 trimethylation is an indicator of a fibrotic condition.

H3K27 trimethylation may be determined using any convenient method for detecting amino acid methylation known to one skilled in the art. Generally, protein methylation at a specific residue, in this case K27 of H3, is detected using an antibody or other binding molecule which recognizes and binds to a methylated K27 residue. In a preferred embodiment, the antibody or other binding molecule recognizes and binds to trimethylated K27 but not an unmethylated, monomethylated, or di-methylated H3K27 residue. Antibodies specific for trimethylated H3K27 are readily known in the art and are commercially available from, e.g., Santa Cruz Biotechnology, Santa Cruz, Calif., and Millipore, Billerica, Mass. Alternatively, antibodies selective for binding to the trimethylated H3K27 residue can be obtained by any standard technique for generating antibodies.

Procedures for raising polyclonal antibodies are well known in the art. Typically, such antibodies can be raised by administering a peptide containing the epitope of interest, i.e., an H3 peptide trimethylated at residue K27, subcutaneously to New Zealand white rabbits which have first been bled to obtain pre-immune serum. The antigens can be injected at a total volume of 100 µl per site at six different sites. Injected material will contain synthetic surfactant adjuvant pluronic polyols, or pulverized acrylamide gel containing the protein or polypeptide after SDS-polyacrylamide gel electrophoresis. The rabbits are bled approximately every two weeks after the first injection and periodically boosted with the same antigen three times every six weeks. A sample of serum is collected 10 days after each boost and polyclonal antibodies are recovered by affinity chromatography using the corresponding antigen to capture the antibody. This and other procedures for raising polyclonal antibodies are disclosed in ANTIBODIES: A LABORATORY MANUAL (Harlow et al. eds., 1988), which is hereby incorporated by reference in its entirety.

A monoclonal antibody is obtained from a substantially homogeneous population of antibodies, i.e., the individual antibodies comprising the population are identical except for possible naturally occurring mutations that may be present in minor amounts. Monoclonal antibodies may be prepared using hybridoma methods, such as those described by Kohler et al., "Continuous Cultures of Fused Cells Secreting Antibody of Predefined Specificity," *Nature* 256:495-7 (1975), and ANTIBODIES: A LABORATORY MANUAL (Harlow et al. eds., 1988), which are hereby incorporated by reference in their entirety. In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro. In accordance with the present invention, the immunizing agent comprises a H3 peptide sequence containing a trimethylated K27 residue.

The antibody producing cells are then fused with an immortalized cell line using a suitable fusing agent, such as polyethylene glycol, to form hybridoma cells, which are cultured in a suitable culture medium that preferably contains one or more substances that inhibit the growth or survival of the unfused, immortalized cells. This and other procedures for producing monoclonal antibodies are disclosed in GODING, MONOCLONAL ANTIBODIES: PRINCIPLES AND PRACTICE 59-103 (1986), Kozbor et al., "A Human Hybrid Myeoloma for Production of Human Monoclonal Antibodies," *J. Immunol.* 133: 3001-05 (1984), and MONOCLONAL ANTIBODY PRODUCTION TECHNIQUES AND APPLICATIONS 51-63 (L. B. Shook ed., 1987), which are hereby incorporated by reference in their entirety.

Detection of H3K27 trimethylation using an antibody or other protein binding molecule selective for binding to the trimethylated K27 residue of H3 can be carried out using any suitable hybridization assay. Suitable hybridization assays include, but are not limited to, enzyme-linked immunosorbent assay (ELISA), dot blot, western blot, chromatin immunoprecipitation (ChIP), ChIP/microarray analysis (see U.S. Patent Application Publication NO. 20070292857 to Rama et al., which is hereby incorporated by reference in its entirety), immunocytochemistry, and immunohistochemistry.

Other binding molecules that can be used for selective binding to trimethylated H3K27 include, without limitation, antibody fragments, antibody mimics, and nucleic acid aptamers.

A number of antibody mimics are known in the art including, without limitation, those known as monobodies, which are derived from the tenth human fibronectin type III domain ($^{10}$Fn3) (Koide et al., "The Fibronectin Type III Domain as a Scaffold for Novel Binding Proteins," *J. Mol. Biol.* 284:1141-1151 (1998); Koide et al., "Probing Protein Conformational Changes in Living Cells by Using Designer Binding Proteins: Application to the Estrogen Receptor," *Proc. Nat'l Acad. Sci. USA* 99:1253-1258 (2002), each of which is hereby incorporated by reference in its entirety); and those known as affibodies, which are derived from the stable α-helical bacterial receptor domain Z of staphylococcal protein A (Nord et al., "Binding Proteins Selected from Combinatorial Libraries of an α-Helical Bacterial Receptor Domain," *Nat. Biotechnol.* 15(8):772-777 (1997), which is hereby incorporated by reference in its entirety). Variations in these antibody mimics can be created by substituting one or more domains of these polypeptides and then screening the modified monobodies or affibodies for specificity for binding to trimethylated H3K27.

Other suitable binding molecules that can be used for detection of trimethylated H3K27 include aptamers that specifically bind to trimethylated H3K27. This is intended to encompass aptamers that, from a structural perspective, are not necessarily considered antibody mimics. Aptamers are single-stranded, partially single-stranded, partially double-stranded, or double-stranded nucleotide sequences, advantageously a replicatable nucleotide sequence, capable of specifically recognizing a selected non-oligonucleotide molecule or group of molecules by a mechanism other than Watson-Crick base pairing or triplex formation. Aptamers include, without limitation, defined sequence segments and sequences comprising nucleotides, ribonucleotides, deoxyribonucleotides, nucleotide analogs, modified nucleotides, and nucleotides comprising backbone modifications, branchpoints, and non-nucleotide residues, groups, or bridges. Aptamers include partially and fully single-stranded and double-stranded nucleotide molecules and sequences; synthetic RNA, DNA, and chimeric nucleotides; hybrids; duplexes; heteroduplexes; and any ribonucleotide, deoxyribonucleotide, or chimeric counterpart thereof and/or corresponding complementary sequence, promoter, or primer-annealing sequence needed to amplify, transcribe, or replicate all or part of the aptamer molecule or sequence.

Alternatively, H3K27 trimethylation can be detected using any other means for detecting protein or peptide modifications that are known in the art, including, but not limited to, two-dimensional gel electrophoresis, mass spectroscopy, matrix-assisted laser desorption/ionization-time of flight (MALDI-TOF), surface-enhanced laser desorption ionization-time of flight (SELDI-TOF), high performance liquid chromatography (HPLC), fast protein liquid chromatography (FPLC), and multidimensional liquid chromatography (LC) followed by tandem mass spectrometry (MS/MS).

In accordance with this aspect of the present invention, the level of H3K27 trimethylation in a sample obtained from a subject is compared to a standard level of H3K27 trimethylation.

In one embodiment of the present invention, the standard level of H3K27 trimethylation is the average level of H3K27 trimethylation in one or more normal or non-fibrotic samples, or a range of values that are consistent with the average level of H3K27 trimethylation in normal or non-fibrotic tissue. A non-fibrotic sample can be a sample that was taken from the subject being diagnosed prior to the onset of the potential fibrotic condition or a sample from one or more non-fibrotic tissues of the subject. A non-fibrotic sample can also be derived from another subject (other than the subject being diagnosed) who does not have fibrosis. According to this embodiment, a higher level of H3K27 trimethylation in the sample from the subject being diagnosed compared to the standard level of H3K27 trimethylation indicates the presence of a fibrotic condition. A similar or lower level of H3K27 trimethylation in the sample from the subject compared to the standard level of H3K27 trimethylation indicates the absence of a fibrotic condition.

In another embodiment, the standard level of H3K27 trimethylation is the average level of H3K27 trimethylation in one or more known fibrotic samples or a range of values that are consistent with the level of H3K27 trimethylation in a fibrotic condition. Accordingly, a lower level of H3K27 trimethylation in the sample from the subject being diagnosed compared to the standard level of H3K27 trimethylation indicates the absence of a fibrotic condition. A similar or higher level of H3K27 trimethylation in the sample from the subject being diagnosed compared to the standard level of H3K27 trimethylation indicates the presence of a fibrotic condition.

This aspect of the present invention may also be used to determine a subject's predisposition to developing a fibrotic condition. This involves comparing the level of H3K27 trimethylation in a biological sample from the subject to a standard level of H3K27 trimethylation in a non-fibrotic tissue or cell sample and to a standard level of H3K27 trimethylation in a fibrotic tissue or cell sample. If the level of H3K27 trimethylation in the sample from the subject is higher than the standard level of H3K27 trimethylation in a non-fibrotic sample, but lower than the standard level of H3K27 trimethylation in a fibrotic sample, the subject may have a predisposition to developing a fibrotic condition. Monitoring changes in H3K27 trimethylation in a subject over time to track development of, or recovery from, a fibrotic condition is also contemplated by the present invention.

A second aspect of the present invention is directed to a method of diagnosing a fibrotic condition in a subject by measuring the expression level of Enhancer of Zeste Homolog 2 ("EZH2") or Yin-Yang-1 ("YY-1") in a biological sample from the subject. The expression level of EZH2 or YY-1 in the biological sample is compared to a standard expression level of EZH2 or YY-1 and the presence or absence of a fibrotic condition is correlated to the results of the comparison.

YY-1 is known to play an important role in the regulation of tumor cell resistance to Fas-induced apoptosis. Increased YY-1 expression represses Fas expression and decreases apoptosis. Blocked NF-κB and p38 decrease YY-1 expression and activate Fas expression (Huerta-Yepez et al., "Involvement of the TNF-α Autocrine-Paracrine Loop, via NF-κB and YY1, in the Regulation of Tumor Cell Resistance to Fas-induced Apoptosis," *Clin. Immunol.* 120(3):297-309 (2006); Vega et al., "Rituximab (Chimeric Anti-CD20) Sensitizes B-NHL Cell Lines to Fas-induced Apoptosis," *Oncogene* 24(55):8114-27 (2005); Lei et al., "p38 MAPK-dependent and YY1-mediated Chemokine Receptors CCR5 and CXCR4 Up-regulation in U937 Cell Line Infected by *Mycobacterium tuberculosis* or *Actinobacillus actinomycetemcomitans*," *Biochem. Biophys. Res. Commun.* 329(2):610-15 (2005), which are hereby incorporated by reference in their entirety). YY-1 and activator protein 1 work synergistically in the activation of the tumor suppressor HLJ1 (Wang et al., "Synergistic Activation of the Tumor Suppressor, HLJ1, by the Transcription Factors YY1 and Activator Protein 1," *Cancer Res.* 67(10):4816-26 (2007), which is hereby incorporated by reference in its entirety). Interestingly, YY1 can bind to type I and II collagen (COL 1 and COL 2) promoters and positively activate these genes in fibroblasts (Riquet et al., "YY1 Is a Positive Regulator of Transcription of the Col1 a1 Gene," *J. Biol. Chem.* 276(42):38665-72 (2001); Miao et al., "Identification of Two Repressor Elements in the Mouse Alpha 2(I) Collagen Promoter," *Arch. Biochem. Biophys.* 361(1):7-16 (1999), which are hereby incorporated by reference in their entirety). YY1 also enhances cyclooxygenase-2 (CoX-2) expression in macrophages (Joo et al., "Yin Yang 1 Enhances Cyclooxygenase-2 Gene Expression in Macrophages," *Am. J. Physiol. Lung Cell Mol. Physiol.* 292(5):L1219-L1226 (2007), which is hereby incorporated by reference in its entirety).

EZH2 is a member of the Polycomb Group (PcG) of genes that is important for differentiation and cell cycle regulation and is aberrantly expressed in several cancers. The EZH2 protein endows the Polycomb complexes, PRC2 and PR3, with histone lysine methyltransferase activity that is associated with gene transcriptional repression (Caretti et al., "The Polycomb EZH2 Methyltransferase Regulates Muscle Gene Expression and Skeletal Muscle Differentiation," *Genes Devel.* 18:2627-38 (2004), which is hereby incorporated by reference in its entirety).

In accordance with this aspect of the present invention, the expression level of EZH2 or YY-1 in a sample obtained from a subject is compared to a standard expression level of EZH2 or YY-1.

In one embodiment of the present invention, the standard expression level of EZH2 or YY-1 is the average expression level of EZH2 or YY-1 in one or more non-fibrotic samples or a range of values that is consistent with the expression levels of EZH2 or YY-1 in normal or non-fibrotic tissue. A non-fibrotic sample can be a sample taken from the subject to be diagnosed prior to the onset of the potential fibrotic condition or from one or more non-fibrotic tissues of the subject. A non-fibrotic sample can also be derived from another subject (other than the subject being diagnosed) who does not have fibrosis. According to this embodiment, a higher expression level of EZH2 or YY-1 in the sample from the subject to be diagnosed compared to the standard expression level of EZH2 or YY-1 indicates the presence of a fibrotic condition. A similar or lower expression level of EZH2 or YY-1 in the sample from the subject compared to the standard expression level of EZH2 or YY-1 indicates the absence of a fibrotic condition.

In another embodiment, the standard expression level of EZH2 or YY-1 is the average expression level of EZH2 or YY-1 in one or more known fibrotic samples or a range of values that is consistent with the expression level of EZH2 or YY-1 in a fibrotic condition. Accordingly, a lower expression level of EZH2 or YY-1 in the sample from the subject to be diagnosed compared to the standard expression level of EZH2 or YY-1 indicates the absence of a fibrotic condition. A similar or higher expression level of EZH2 or YY-1 in the sample from the subject compared to the standard expression level of EZH2 or YY-1 indicates the presence of a fibrotic condition.

This aspect of the present invention may also be used to determine a subject's predisposition to developing a fibrotic condition. This involves comparing the level of EZH2 or YY-1 expression in a biological sample from the subject to a standard level of EZH2 or YY-1 expression in a non-fibrotic tissue or cell sample and to a standard level of EZH2 or YY-1 expression in a fibrotic tissue or cell sample. If the level of EZH2 or YY-1 expression in the sample from the subject is higher than the standard level of EZH2 or YY-1 expression in a non-fibrotic sample, but lower than the standard level of EZH2 or YY-1 expression in a fibrotic sample, the subject may have a predisposition to developing a fibrotic condition. Monitoring changes in EZH2 and/or YY-1 expression in a subject over time to track development of, or recovery from, a fibrotic condition is also contemplated by the present invention.

As described herein, detecting the "expression level" of EZH2 or YY-1 can be achieved by measuring any suitable value that is representative of gene expression level. The measurement of gene expression levels can be direct or indirect. A direct measurement involves measuring the level or quantity of RNA or protein. An indirect measurement may involve measuring the level or quantity of cDNA, or amplified RNA, DNA, or protein; the activity level of RNA or protein; or the level or activity of other molecules (e.g., a metabolite) that are indicative of the foregoing. The measurement of expression can be a measurement of the absolute quantity of a gene product. The measurement can also be a value representative of the absolute or relative quantity, i.e., a normalized value (e.g., a quantity of gene product normalized against the quantity of a reference gene product), an averaged value (e.g., average quantity obtained at different time points or from different tumor cell samples from a subject, or average quantity obtained using different probes, etc.), or a combination of both.

In a preferred embodiment of the present invention, the expression level of EZH2 or YY-1 is measured by measuring the RNA expression level of EZH2 or YY-1. Methods for isolation and purification of nucleic acids suitable for measuring RNA expression levels in accordance with the methods of the present invention are described in detail in LABORATORY TECHNIQUES IN BIOCHEMISTRY AND MOLECULAR BIOLOGY: HYBRIDIZATION WITH NUCLEIC ACID PROBES, PART I. THEORY AND NUCLEIC ACID PREPARATION (P. Tijssen ed., 1993) which is hereby incorporated by reference in its entirety. Total RNA can be isolated from a given sample using, for example, an acid guanidinium-phenol-chloroform extraction, a guanidinium isothiocyanate-ultracentrifugation method, or a lithium chloride-SDS-urea method, and polyA$^+$ mRNA can be isolated using oligo(dT) column chromatography or (dT)n magnetic beads (see, e.g., JOSEPH SAMBROOK et al., 1-3 MOLECULAR CLONING: A LABORATORY MANUAL (2d ed. 1989); 1-4 CURRENT PROTOCOLS IN MOLECULAR BIOLOGY (Fred M. Ausubel et al. eds., 1994), which are hereby incorporated by reference in their entirety). See also WO/2000024939 to Dong et al., which is hereby incorporated by reference in its entirety, for complexity management and other nucleic acid sample preparation techniques.

It may be desirable to amplify the nucleic acid sample prior to detecting gene expression. Typically, methods for amplifying nucleic acids employ a polymerase chain reaction (PCR) (see e.g., PCR TECHNOLOGY: PRINCIPLES AND APPLICATIONS FOR DNA AMPLIFICATION (Erlich ed., 1992); PCR PROTOCOLS: A GUIDE TO METHODS AND APPLICATIONS (Innis et al. eds., 1990); Mattila et al., "Fidelity of DNA Synthesis by the *Thermococcus litoralis* DNA Polymerase—An Extremely Heat Stable Enzyme with Proofreading Activity," *Nucleic Acids Res.* 19:4967-73 (1991); Eckert et al., "DNA Polymerase Fidelity and the Polymerase Chain Reaction," *PCR Meth. Applic.* 1:17-24 (1991); MICHAEL MCPHERSON & SIMON MØLLER, PCR (THE BASICS) (2d. ed. 2006); U.S. Pat. No. 4,683,202 to Mullis et al.; U.S. Pat. No. 4,683,195 to Mullis et al.; U.S. Pat. No. 4,800,159 to Mullis et al.; U.S. Pat. No. 4,965,188 to Mullis et al.; U.S. Pat. No. 5,333,675 to Mullis et al., which are hereby incorporated by reference in their entirety). The sample may also be amplified on an array as described in U.S. Pat. No. 6,300,070 to Boles, which is incorporated herein by reference in its entirety.

Other suitable amplification methods include the ligase chain reaction (LCR) (e.g., Wu et al., "The Ligation Amplification Reaction (LAR)—Amplification of Specific DNA Sequences Using Sequential Rounds of Template-Dependent Ligation," *Genomics* 4:560-9 (1989); Landegren et al., "A Ligase-Mediated Gene Detection Technique," *Science* 241: 1077-80 (1988); Barringer et al., "Blunt-End and Single-Strand Ligations by *Escherichia coli* Ligase: Influence on an In vitro Amplification Scheme," *Gene* 89:117-22 (1990), which are hereby incorporated by reference in their entirety); transcription amplification (Kwoh et al., "Transcription-Based Amplification System and Detection of Amplified Human Immunodeficiency Virus Type 1 with a Bead-Based Sandwich Hybridization Format," *Proc. Nat'l Acad. Sci. USA* 86:1173-77 (1989); International Patent Publication No. WO88/10315 to Gingeras, which are hereby incorporated by reference in their entirety); self-sustained sequence replication (Guatelli et al., "Isothermal, In vitro Amplification of Nucleic Acids by a Multienzyme Reaction Modeled After Retroviral Replication," *Proc. Nat'l Acad. Sci. USA* 87:1874-78 (1990); International Patent Publication No. WO90/06995 to Gingeras, which are hereby incorporated by reference in their entirety); selective amplification of target polynucleotide sequences (U.S. Pat. No. 6,410,276 to Burg et al, which is hereby incorporated by reference in its entirety); consensus sequence primed polymerase chain reaction (CP-PCR) (U.S. Pat. No. 5,437,975 to McClelland, which is hereby incorporated by reference in its entirety); arbitrarily primed polymerase chain reaction (AP-PCR) (U.S. Pat. No. 5,413,909 to Bassam; U.S. Pat. No. 5,861,245 to McClelland, which are hereby incorporated by reference in their entirety); and nucleic acid based sequence amplification (NABSA) (see U.S. Pat. No. 5,409,818 to Davey; U.S. Pat. No. 5,554,517 to Davey; U.S. Pat. No. 6,063,603 to Davey, which are hereby incorporated by reference in their entirety). Other amplification methods that may be used are described in U.S. Pat. No. 5,242,794 to Whiteley; U.S. Pat. No. 5,494,810 to Barmy; and U.S. Pat. No. 4,988,617 to Landegren, which are hereby incorporated by reference in their entirety.

Measuring gene expression by quantifying mRNA expression can be achieved using any method known in the art including northern blotting and in situ hybridization (Parker et al., "mRNA: Detection by In Situ and Northern Hybridization," *Meth. Mol. Biol.* 106:247-283 (1999), which is hereby incorporated by reference in its entirety); RNAse protection assay (Hod et al., "A Simplified Ribonuclease Protection Assay," *Biotechniques* 13:852-854 (1992), which is hereby incorporated by reference in its entirety); reverse transcription polymerase chain reaction (RT-PCR) (Weis et al., "Detection of Rare mRNAs via Quantitative RT-PCR," *Trends Genet.* 8:263-264 (1992), which is hereby incorporated by reference in its entirety), and serial analysis of gene expression (SAGE) (e.g., Velculescu et al., "Serial Analysis of Gene Expression," *Science* 270:484-487 (1995); Velculescu et al., "Characterization of the Yeast Transcriptome," *Cell* 88:243-51 (1997), which are hereby incorporated by reference in their entirety). Alternatively, antibodies may be employed that recognize specific duplexes, including DNA duplexes, RNA duplexes, and DNA-RNA hybrid duplexes or DNA-protein duplexes.

In a preferred embodiment of the present invention, mRNA expression is measured using a nucleic acid amplification assay that is a semi-quantitative or quantitative real-time polymerase chain reaction (RT-PCR) assay. Because RNA cannot serve as a template for PCR, the first step in gene expression profiling by RT-PCR is the reverse transcription of the RNA template into cDNA, followed by its exponential amplification and detection in a PCR reaction. The two most commonly used reverse transcriptases are avilo myeloblastosis virus reverse transcriptase (AMV-RT) and Moloney murine leukemia virus reverse transcriptase (MLV-RT), although others are also known and suitable for this purpose. The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. TaqMan® PCR typically utilizes the 5'-nuclease activity of Taq or Tth polymerase to hydrolyze a hybridization probe bound to its target amplicon, but any enzyme with equivalent 5' nuclease activity can be used. TaqMan® PCR further involves the use of two oligonucleotide primers to generate an amplicon typical of a PCR reaction. A third oligonucleotide, or probe, is designed to detect the nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TaqMan® PCR can be performed using commercially available equipment, such as, for example, the ABI PRISM 7700® Sequence Detection System® (Perkin-Elmer-Applied Biosystems, Foster City, Calif., USA) or the Lightcycler (Roche Molecular Biochemicals, Mannheim, Germany).

TaqMan® PCR is one of many quantitative PCR systems known and available in the art. Other quantitative methods and reagents for real-time PCR detection that are known in the art (e.g. SYBR green, Molecular Beacons, Scorpion Probes, etc) are also suitable for use in the methods of the present invention.

To minimize errors and the effect of sample-to-sample variation, RT-PCR is usually performed using an internal standard. The ideal internal standard is expressed at a constant level among different tissues, and is unaffected by the experimental treatment or disease. RNAs most frequently used to normalize patterns of gene expression are mRNAs for the housekeeping genes glyceraldehyde-3-phosphate-dehydrogenase (GAPDH) and β-actin.

Real time PCR is compatible both with quantitative competitive PCR, where an internal competitor for each target sequence is used for normalization and quantitative comparative PCR using a normalization gene contained within the sample, or a housekeeping gene for RT-PCR. For further details see, e.g., Heid et al., "Real Time Quantitative PCR," *Gen. Res.* 6:986-94 (1996), which is incorporated by reference in its entirety.

When it is desirable to analyze a large quantity of samples for EZH2 and YY-1 expression levels in a high-throughput manner, or when it is desirable to measure the expression levels of other genes in addition to EZH2 and YY-1, an array-based technique can be employed. These arrays, also commonly referred to as "microarrays" or "chips," have been generally described in the art (e.g., U.S. Pat. No. 5,143,854 to Pirrung et al.; U.S. Pat. No. 5,445,934 to Fodor et al.; U.S. Pat. No. 5,744,305 to Fodor et al.; U.S. Pat. No. 5,677,195 to Winkler et al.; U.S. Pat. No. 6,040,193 to Winkler et al.; U.S. Pat. No. 5,424,186 to Fodor et al., which are all hereby incorporated by reference in their entirety). A microarray comprises an assembly of distinct polynucleotide or oligonucleotide probes immobilized at defined positions on a substrate. Arrays are formed on substrates fabricated with materials such as paper, glass, plastic (e.g., polypropylene, nylon), polyacrylamide, nitrocellulose, silicon, optical fiber or any other suitable solid or semi-solid support, and configured in a planar (e.g., glass plates, silicon chips) or three-dimensional (e.g., pins, fibers, beads, particles, microtiter wells, capillaries) configuration. Probes forming the arrays may be attached to the substrate by any number of ways including (i) in situ synthesis (e.g., high-density oligonucleotide arrays) using photolithographic techniques (Fodor et al., "Light-directed, Spatially Addressable Parallel Chemical Synthesis," *Science* 251:767-773 (1991); Pease et al., "Light-generated Oligonucleotide Arrays for Rapid DNA Sequence Analysis," *Proc. Nat'l Acad. Sci. U.S.A.* 91:5022-5026 (1994); Lockhart et al., "Expression Monitoring by Hybridization to High-Density Oligonucleotide Arrays," *Nat. Biotechnol.* 14:1675 (1996); U.S. Pat. No. 5,578,832 to Trulson; U.S. Pat. No. 5,556,752 to Lockhart; U.S. Pat. No. 5,510,270 to Fodor, which are hereby incorporated by reference in their entirety); (ii) spotting/printing at medium to low-density (e.g., cDNA probes) on glass, nylon or nitrocellulose (Schena et al., "Quantitative Monitoring of Gene Expression Patterns with a Complementary DNA Microarray," *Science* 270:467-470 (1995); DeRisi et al., "Use of a cDNA Microarray to Analyze Gene Expression Patterns in Human Cancer," *Nat. Genet.* 14:457-460 (1996); Shalon et al., "A DNA Microarray System for Analyzing Complex DNA Samples Using Two-Color Fluorescent Probe Hybridization," *Gen. Res.* 6:639-645 (1996); Schena et al., "*Proc. Nat'l Acad. Sci. U.S.A.* 93:10539-11286) (1995), which are hereby incorporated by reference in their entirety); (iii) masking (Maskos et al., "Oligonucleotide Hybridizations on Glass Supports: A Novel Linker for Oligonucleotide Synthesis and Hybridization Properties of Oligonucleotides Synthesized In Situ," *Nucl. Acids. Res.* 20:1679-1684 (1992), which is hereby incorporated by reference in its entirety); and (iv) dot-blotting on a nylon or nitrocellulose hybridization membrane (e.g., JOSEPH SAMBROOK et al., 1-3 MOLECULAR CLONING: A LABORATORY MANUAL (2d ed. 1989), which is hereby incorporated by reference in its entirety). Probes may also be non-covalently immobilized on the substrate by hybridization to anchors, by means of magnetic beads, or in a fluid phase such as in microtiter wells or capillaries. The probe molecules are generally nucleic acids such as DNA, RNA, PNA, and cDNA, but may also include proteins, polypeptides, oligosaccharides, cells, tissues, and any permutations thereof which can specifically bind the target molecules.

Fluorescently labeled cDNA for hybridization to the array may be generated through incorporation of fluorescent nucleotides by reverse transcription of RNA extracted from the fibrotic tissue of interest. Labeled cDNA applied to the array hybridizes with specificity to each nucleic acid probe spotted on the array. After stringent washing to remove non-specifically bound cDNA, the array is scanned by confocal laser microscopy or by another detection method, such as a CCD camera. Quantitation of hybridization of each arrayed element allows for assessment of corresponding mRNA abundance. With dual color fluorescence, separately labeled cDNA samples generated from two sources of RNA are hybridized pairwise to the array. The relative abundance of the transcripts from the two sources corresponding to each specified gene is thus determined simultaneously.

Other nucleic acid detection protocols can also be employed, including (without limitation) those described in U.S. patent application Ser. Nos. 10/847,233 and 11/337,905 to Rothberg et al., which are hereby incorporated by reference in their entirety; arrayed imaging reflectometry ("AIR") (U.S. Pat. No. 7,292,349 to Miller et al., which is hereby incorporated by reference in its entirety); Brewster angle straddle interferometry (BASI) (U.S. Patent Publication No. 2007/0076214, which is hereby incorporated by reference in its entirety); imaging ellipsometry (U.S. Pat. No. 5,076,696 to Cohn et al.; U.S. Pat. No. 6,594,011 to Kempen, which are hereby incorporated by reference in their entirety); and surface plasmon resonance ellipsometry ("SPR") (U.S. Pat. No. 7,332,239 to Wark et al., which is hereby incorporated by reference in its entirety).

In another embodiment of the present invention, the expression levels of EZH2 or YY-1 is measured by measuring the level of protein expression. Measuring the protein expression levels of EZH1 or YY-1 can be achieved using any standard protein immunodetection assay known in the art.

Protein preparation for analysis of protein expression level is carried out using any method that produces analyzable protein. For example, the sample cells or tissue can be lysed in a protein lysis buffer (e.g., 50 mM Tris-HCl (pH, 6.8), 100 mM DTT, 100 µg/ml PMSF, 2% SDS, 10% glycerol, 1 µg/ml each of pepstatin A, leupeptin, and aprotinin, and 1 mM sodium orthovanadate) and sheared with a 22-gauge needle. Other methods of protein isolation that are suitable for use in carrying out the methods of the present invention are fully described in C. DENNISON, A GUIDE TO PROTEIN ISOLATION (2d ed. 2003), which is hereby incorporated by reference in its entirety. The protein content of the samples can be estimated using the Lowry, Bradford, or bicinchoninic acid assays, or any commercially available assay based on the aforementioned techniques.

In a preferred embodiment of the present invention, a protein immunodetection assay using an antibody or other agent that selectively binds to EZH2 of YY-1 is employed to detect EZH2 or YY-1 protein expression in a sample. For example, the level of protein expression can be measured using methods that include, but are not limited to, western blot, immunoprecipitation, ELISA, radioimmunoassay (RIA), and fluorescent activated cell sorting (FACS), or a combination thereof. Also, antibodies, aptamers, or other ligands that specifically bind to a protein can be affixed to so-called "protein chips" (protein microarrays) and used to measure the level of expression of a protein in a sample. Immunofluorescence techniques can be used to visually assess the expression level of a protein in a sample. Immunofluorescence techniques involve the utilization of antibodies that specifically bind to a protein and are visualized to indirectly detect the presence of a protein in a sample. Alternatively, assessing the level of protein expression can involve analyzing one or more proteins by two-dimensional gel electrophoresis, mass spectroscopy, MALDI-TOF, surface-enhanced laser desorption ionization-time of flight (SELDI-TOF), high performance liquid chromatography (HPLC), fast protein liquid chromatography (FPLC), multidimensional liquid chromatography (LC) followed by tandem mass spectrometry (MS/MS), protein chip expression analysis, gene chip expression analysis, and laser densitometry, or any combinations of these techniques.

Another aspect of the present invention is directed to a method of treating a subject having a fibrotic condition. This method involves administering to the subject an agent that inhibits or reduces H3K27 trimethylation under conditions effective to treat a fibrotic condition in the subject.

In a preferred embodiment of this aspect of the present invention, a subject having a fibrotic condition is selected prior to administering an agent that inhibits or reduces H3K27 trimethylation. Subjects who are suitable for receiving treatment in accordance with this aspect of the present invention are those suffering from a fibrotic condition affecting the lungs, heart, kidney, liver, brain, skin, or any fibrosis related disease, including, but not limited to, those described above. In a preferred embodiment the fibrotic condition is lung or pulmonary fibrosis (e.g., idiopathic pulmonary fibrosis).

In another embodiment of this aspect of the present invention, administering the agent that inhibits or reduces H3K27 trimethylation is repeated one or more times as needed to alleviate the fibrotic condition.

Agents suitable for treating a subject having a fibrotic condition include those agents that inhibit or reduce H3K27 methylation. Exemplary agents include histone lysine demethylases, such as those of the human jumonji C (JmjC)-domain-containing-3 family of histone demethylases. Preferably, the histone lysine demethylase is (a) jumonji domain containing-3 (JMJD$_3$) or (b) ubiquitously transcribed tetratricopeptide repeat, X chromosome (UTX) demethylase.

In another embodiment of this aspect of the present invention, agents suitable for treating a subject having a fibrotic condition are agents that inhibit EZH2 expression or activity or agents that inhibit YY-1 expression or activity. Therapeutic agents that inhibit EZH2 or YY-1 expression include nucleic acids, proteins or peptides, and small molecule inhibitors.

Suitable nucleic acid molecule inhibitors of EZH2 and YY-1 include antisense RNAs or RNAi, such as short interfering RNAs (siRNA), short hairpin RNAs (shRNA), and microRNAs.

The use of antisense methods to inhibit the in vivo translation of genes is well known in the art (e.g., U.S. Pat. No. 7,425,544 to Dobie et al.; U.S. Pat. No. 7,307,069 to Karras et al.; U.S. Pat. No. 7,288,530 to Bennett et al.; U.S. Pat. No. 7,1791796 to Cowsert et al., which are hereby incorporated by reference in their entirety). Antisense nucleic acids are nucleic acid molecules (e.g., molecules containing DNA nucleotides, RNA nucleotides, or modifications (e.g., modification that increase the stability of the molecule, such as 2'-O-alkyl (e.g., methyl) substituted nucleotides) or combinations thereof) that are complementary to, or that hybridize to, at least a portion of a specific nucleic acid molecule, such as an RNA molecule (e.g., an mRNA molecule) (e.g., Weintraub, H. M., "Antisense DNA and RNA," *Scientific Am.* 262:40-46 (1990), which is hereby incorporated by reference in its entirety). The antisense nucleic acids hybridize to corresponding nucleic acids, such as mRNAs, to form a double-stranded molecule, which interferes with translation of the mRNA, as the cell will not translate a double-stranded mRNA. Antisense nucleic acids used in the invention are typically at least 10-12 nucleotides in length, for example, at least 15, 20, 25, 50, 75, or 100 nucleotides in length. The antisense nucleic acid can also be as long as the target nucleic acid with which it is intended to form an inhibitory duplex. Antisense molecules directed to YY-1 and EZH2, which are known in the art, are particularly suited for use in the methods of the present invention (Kwon et al., "Yin Yang-1, A Vertebrate Polycomb Group Gene, Regulates Antero-Posterior Neural Patterning," *Biochem. Biophys. Res. Comm.* 306(4) 1008-1013 (2003); Varambally et al., "The Polycomb Group Protein EZH2 is Involved in Progression of Prostate Cancer," *Nature* 419:624-629 (2002), which are hereby incorporated by reference in their entirety). Antisense nucleic acids can be introduced into cells as antisense oligonucleotides, or can be produced in a cell in which a nucleic acid encoding the antisense nucleic acid has been introduced, for example, using gene therapy methods.

siRNAs are double stranded synthetic RNA molecules approximately 20-25 nucleotides in length with short 2-3 nucleotide 3' overhangs on both ends. The double stranded siRNA molecule represents the sense and anti-sense strand of a portion of the target mRNA molecule, in this case a portion of the EZH2 or YY-1 mRNA sequence. siRNA molecules are typically designed to target a region of the mRNA target approximately 50-100 nucleotides downstream from the start codon. Upon introduction into a cell, the siRNA complex triggers the endogenous RNA interference (RNAi) pathway, resulting in the cleavage and degradation of the target mRNA molecule. A number of siRNA molecules directed to interfering with EZH2 expression are known in the art (e.g., U.S. Patent Publication No. 2005/0159382, which is hereby incorporated by reference in its entirety) and are suitable for use in the present invention. In addition, various improvements of siRNA compositions, such as the incorporation of modified nucleosides or motifs into one or both strands of the siRNA molecule to enhance stability, specificity, and efficacy, have been described and are suitable for use in accordance with this aspect of the invention (International Patent Publication No. WO 2004/015107 to Giese et al.; International Patent Publication No. WO 2003/070918 to McSwiggen et al.; International Patent Publication No. WO 1998/39352 to Imanishi et al.; U.S. Patent Application Publication No. 2002/0068708 to Jesper et al.; U.S. Patent Application Publication No. 2002/0147332 to Kaneko et al; U.S. Patent Application Publication No. 2008/0119427 to Bhat et al., which are hereby incorporated by reference in their entirety).

Short or small hairpin RNA molecules are similar to siRNA molecules in function, but comprise longer RNA sequences that make a tight hairpin turn. Like siRNA, they silence gene expression via the cellular RNA interference pathway. shRNA is cleaved by cellular machinery into siRNA. Suitable shRNA molecules for inhibiting YY-1 expression that can be used in accordance with the methods of the present invention include, without limitation:

(SEQ ID NO: 1)
CGACGGTTGTAATAAGAAGTTCTCGAGAACTTCTTATTACAACCGTCG, (SEQ ID NO: 2)
CCCTAAGCAACTGGCAGAATTCTCGAGAATTCTGCCAGTTGCTTAGGG, (SEQ ID NO: 3)
GTGGTTGAAGAGCAGATCATTCTCGAGAATGATCTGCTCTTCAACCAC, (SEQ ID NO: 4)
CACATCTTAACACACGCTAAACTCGAGTTTAGCGTGTGTTAAGATGTG, (SEQ ID NO: 5)
GCCCTCATAAAGGCTGCACAACTCGAGTTGTGCAGCCTTTATGAGGGC, (SEQ ID NO: 6)
CCCTCCTGATTATTCAGAATATTAGTGAAGCCACAGATGTAATATTCTGAATAATCAGGAGGT, (SEQ ID NO: 23)
CCGGGCCCTCATAAAGGCTGCACAACTCGAGTTGTGCAGCCTTTATGAGGGCTTTTTG,
(sense)

(SEQ ID NO: 24)
CAAAAAGCCCTCATAAAGGCTGCACAACTCGAGTTGTGCAGCCTTTATGAGGGCCCGG,
(antisense)

(SEQ ID NO: 25)
CCGGGTGGTTGAAGAGCAGATCATTCTCGAGAATGATCTGCTCTTCAACCACTTTTTG,
(sense)
and (SEQ ID NO: 26)
CAAAAAGTGGTTGAAGAGCAGATCATTCTCGAGAATGATCTGCTCTTCAACCACCCGG.
(antisense)

Aptamers are molecules that interact and bind to a target molecule with a very high degree of specificity. Typically, aptamers are small nucleic acids ranging from 15-50 bases in length that fold into defined secondary and tertiary structures, such as stem-loops or G-quartets. Aptamers can bind small molecules as well as large molecules (U.S. Pat. No. 5,631,146; U.S. Pat. No. 5,786,462; U.S. Pat. No. 5,543,293; U.S. Pat. No. 5,580,737, which are hereby incorporated by reference in their entirety). Aptamers can bind very tightly with $K_d$s for the target molecule of less than $10^{-12}$ M. It is preferred that the aptamers bind the target molecule with a $K_d$ less than $10^{-6}$. It is more preferred that the aptamers bind the target molecule with a $K_d$ less than $10^{-8}$.

Other nucleic acid molecules suitable for the inhibition of EZH2 or YY-1 include ribozymes (U.S. Pat. No. 5,334,711 to Sproat et al; U.S. Pat. No. 5,646,031 to DeYoung et al.; U.S. Pat. No. 5,595,873 to Joyce et al.; U.S. Pat. No. 5,580,967 to Joyce et al., which are hereby incorporated by reference in their entirety), triplex forming functional nucleic acid molecules (U.S. Pat. No. 5,176,996 to Hogan et al., which is hereby incorporated by reference in its entirety), and external guide sequences (EGSs) (International Patent Publication No. WO 92/03566 to Yale; Forster & Altman, "External Guide Sequences for an RNA Enzyme," *Science* 249:783-86 (1990), which are hereby incorporated by reference in their entirety).

Therapeutic protein or peptide inhibitors of EZH2 or YY-1 expression or activity are also suitable for use in accordance with this aspect of the present invention. Protein inhibitors include antibodies (e.g. single chain antibodies, chimeric antibodies, hybrid antibodies), intrabodies, peptide aptamers, or any other binding molecules, including synthetic peptide inhibitors, having antigen binding specificity for EZH2 or YY-1. Therapeutically effective antibodies or other binding molecules of the present invention are those having antigen specificity for EZH2 or YY-1, which inhibit EZH2 or YY-1 activity upon binding of the antibody or binding molecule to EZH2 or YY-1. Preferably the antibody or other binding molecule of the present invention recognizes one or more portions of the EZH2 or YY-1 proteins involved in polycomb repressive complex formation, DNA binding, or histone-3 methylation, such that H3K27 trimethylation is inhibited. Antibodies having antigen specificity for EZH2 and YY-1 are known in the art (Bergad et al., "Yin-Yang 1 and Glucocorticoid Receptor Participate in the StatS-Mediated Growth Hormone Response of the Serine Protease Inhibitor 2.1 Gene," *J.*

Biol. Chem. 275(11):8114-20 (2000); Raman et al., "Increased Expression of the Polycomb Group Gene, EZH2, in Transitional Cell Carcinoma of the Bladder," *Clin. Cancer Res.* 11:8750-76 (2005), which are hereby incorporated by reference in their entirety). Alternatively, the antibody or other binding molecule of the present invention has antigen binding specificity for a protein in the EZH2 or YY-1 signal transduction pathway, where upon binding of the antibody or other binding molecule to its target protein, EZH2 and/or YY-1 function is indirectly disrupted. An exemplary antibody known to inhibit YY-1 function indirectly that is suitable for use in the methods of the present invention is Rituximab. Rituximab inhibits YY-1 expression and activity by disrupting both the p38 mitogen-activated protein kinase signaling pathway and NFκB activity (Vega et al., "Rituximab (Chimeric Anti-CD20) Sensitized B-NHL Cell Lines to Fas-Induced Apoptosis," *Oncogene* 24:8114-8127 (2005), which is hereby incorporated by reference in its entirety).

Alternative therapeutic protein inhibitors suitable for use in this aspect of the present invention include dominant negative forms of the EZH2 or YY-1 protein. Preferable dominant negative EZH2 or YY-1 proteins are deficient in polycomb repressive complex formation or DNA binding capacity such that histone-3 methylation or transcriptional activity are attenuated. A preferred dominant negative YY-1 protein that is particularly suitable for use in the methods of the present invention is the DZ-YY-1 protein, described herein, that lacks four zinc-finger domains and is deficient in DNA binding and subsequent transcriptional activity.

Other known inhibitors of YY-1 that are suitable for use in accordance with this aspect of the invention include nitric oxide or nitric oxide donors, such as DEA-NONOate, as described in Garban & Bonavida, "Nitric Oxide Inhibits the Transcription Repressor Yin-Yang 1 Binding Activity at the Silencer Region of the Fas Promoter: A Pivitol Role for Nitric Oxide in the Up-Regulation of Fas Gene Expression in Human Tumor Cells," *J. Immun.* 167:75-81 (2001), which is hereby incorporated by reference in its entirety, and NPI-0052, as described in Baritaki et al., "Inhibition of Yin Yang 1-Dependent Repressor Activity of DR5 Transcription and Expression by the Novel Proteasome Inhibitor NPI-0052 Contributes to Its TRAIL-Enhanced Apoptosis in Cancer Cells," *J. Immun.* 180:6199-210 (2008), which is hereby incorporated by reference in its entirety.

In another embodiment of this aspect of the present invention, the agent for treating a subject having a fibrotic condition is a histone deacetylase (HDAC) inhibitor. HDAC inhibitors suitable for use in the present invention include nucleoplasmin, chamydocin, Cyl-2, cyclic(eta-oxo-alpha-aminooxiraneoctanoylphenylalanylleucyl-2-piperidinecarbonyl (WF-3161), depudecin, radicocol, oxamfiatin, apidicin, suberoxylanilide hydroxamic acid, and 2-amino-8-oxo-9,10-epoxy-decanoic acid as disclosed in U.S. Patent Application Publication No. 2005/0222013 to Mira et al., which is hereby incorporated by reference in its entirety. In addition, U.S. Pat. No. 6,376,508 to Li, which is hereby incorporated by reference in its entirety, discloses the use of butyrate, trapoxin analogs, and trichostatin A as potent HDAC inhibitors that are also suitable for use in the present invention. Other HDAC inhibitors known in the art that are suitable for use in the present invention include valproic acid and its derivatives (U.S. Pat. No. 7,265,154 to Gottlicher, which is hereby incorporated by reference in its entirety); carbamic acid compounds comprising sulfonamide linkages (U.S. Pat. No. 6,888,027 to Watkins, which is hereby incorporated by reference in its entirety); compounds having a zinc-binding moiety, such as a hydroxamic acid group (U.S. Pat. No. 6,495,716 to Lan-Hargest et al., which is hereby incorporated by reference in its entirety); cyclic tetrapeptide derivatives disclosed in U.S. Pat. No. 6,825,317 to Nishino, which is hereby incorporated by reference in its entirety; and any of the HDAC inhibitory compounds disclosed in U.S. Pat. No. 7,399,884 to Bressi, U.S. Pat. No. 7,381,825 to Bressi, U.S. Pat. No. 7,375,228 to Bressi, U.S. Pat. No. 7,169,801 to Bressi, and U.S. Pat. No. 7,154,002 to Bressi, which are hereby incorporated by reference in their entirety. Other HDAC inhibitors, including m-carboxycinnamic acid bis-hydroxamie and the bicyclic depsipeptide FK228 (Adachi et al., "Synergistic Effect of Histone Deacetylase Inhibitors FK228 and m-Carboxycinnamic Acid Bis-Hydroxamide with Proteasome Inhibitors PSI and PS-341 Against Gastrointestinal Adenocarcinoma Cells," *Clin. Cancer Res.* 10:3853-62 (2004), which is hereby incorporated by reference in its entirety); the benzamide M344 (Riessland et al., "The Benzamide M344, A Novel Histone Deacetylase Inhibitor, Significantly Increases SMN2 RNA/Protein Levels in Spinal Muscular Atrophy Cells," *Hum. Genet.* 120(10)101-10 (2006), which is hereby incorporated by reference in its entirety); and 3-(4-aroyl-2-pyrrolyl)-N-hydroxy-2-propenamides (Massa et al., "3-(4-aroyl-1H-pyrrol-2-yl)-N-hydroxy-2-propenamides, A New Class of Synthetic Histone Deacetylase Inhibitors," *J. Med. Chem.* 44(13)2069-72 (2001), which is hereby incorporated by reference in its entirety), are also suitable for use in the present invention.

In another embodiment of the present invention, an anti-inflammatory agent is administered in conjunction with the agent that inhibits or reduces H3K27 trimethylation. Suitable anti-inflammatory agents include, but are not limited to, nimesulide, 4-hydroxynimesulide, flosulide, meloxicam, celecoxib, and Rofecoxib.

Another aspect of the present invention is directed to a pharmaceutical composition that is suitable for the treatment of a fibrotic condition. The pharmaceutical composition contains a pharmaceutically acceptable delivery vehicle and an effective amount of one or more agents selected from an agent that inhibits or reduces H3K27 trimethylation, an inhibitor of EZH2, an inhibitor of YY-1, an inhibitor of histone deacetylase, or any combination of agents thereof. Appropriate delivery vehicles include, but are not limited to, lung surfactants, liposomes, viral vectors, and nanoparticle delivery vehicles, which are all described in more detail below.

The methods of the present invention are intended to be carried out by administering the active agents alone or in combination with one another, but preferably in the form of one or more pharmaceutical compositions that include a pharmaceutically acceptable carrier for the therapeutic agent(s).

As will be apparent to one of ordinary skill in the art, administering any of the above agents to a subject to treat fibrosis may be carried out using generally known methods. Typically, the agent is administered by introducing the agent into the subject. Administration can be accomplished either via systemic administration to the subject, administration directly to a fibrotic tissue site, or via targeted administration to affected cells. Exemplary routes of administration include, without limitation, by intratracheal inoculation, aspiration, airway instillation, aerosolization, nebulization, intranasal instillation, oral or nasogastric instillation, intraperitoneal injection, intravascular injection, topically, transdermally, parenterally, subcutaneously, by intravenous injection, by intra-arterial injection (such as via the pulmonary artery), by intramuscular injection, by intrapleural instillation, intraventricularly, intralesionally, by application to mucous membranes (such as that of the nose, throat, and/or bronchial tubes), or by implantation of a sustained release vehicle adjacent to the affected tissue.

Typically, the therapeutic agent (i.e., histone lysine demethylase, EZH2 or YY-1 inhibitor, or histone deacetylase inhibitor) will be administered to a mammal as a pharmaceutical formulation that includes the therapeutic agent and any pharmaceutically acceptable suitable adjuvants, carriers, excipients, and/or stabilizers, and can be in solid or liquid form, such as tablets, capsules, powders, solutions, suspensions, or emulsions. The compositions preferably contain from about 0.01 to about 99 weight percent, more preferably from about 2 to about 60 weight percent, of therapeutic agent together with the adjuvants, carriers, and/or excipients. The amount of active compound in such therapeutically useful compositions is such that a suitable dosage unit will be obtained.

The agents may be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, these active compounds may be incorporated with excipients and used in the form of tablets, capsules, elixirs, suspensions, syrups, and the like. Such compositions and preparations should contain at least 0.1% of the agent. The percentage of the agent in these compositions may, of course, be varied and may conveniently be between about 2% to about 60% of the weight of the unit. The amount of the agent in such therapeutically useful compositions is such that a suitable dosage will be obtained.

The tablets, capsules, and the like may also contain a binder such as gum tragacanth, acacia, corn starch, or gelatin; excipients such as dicalcium phosphate; a disintegrating agent such as corn starch, potato starch, or alginic acid; a lubricant such as magnesium stearate; and a sweetening agent such as sucrose, lactose, or saccharin. When the dosage unit form is a capsule, it may contain, in addition to materials of the above type, a liquid carrier, such as a fatty oil.

Various other materials may be present as coatings or to modify the physical form of the dosage unit. For instance, tablets may be coated with shellac, sugar, or both. A syrup may contain, in addition to active ingredient(s), sucrose as a sweetening agent, methyl and propylparabens as preservatives, a dye, and flavoring such as cherry or orange flavor.

The agents may also be administered parenterally. Solutions or suspensions of the agent can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The agents according to this aspect of the present invention may also be administered directly to the airways in the form of an aerosol. For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

As another alternative, the agents of the present invention may be administered to the airways in the form of a lung surfactant formulation. The lung surfactant formulation can include exogenous lung surfactant formulations (e.g., Infasurf® (Forest Laboratories), Survanta® (Ross Products), and Curosurf® (DEY, California, USA) or synthetic lung surfactant formulations (e.g., Exosurf (GlaxoWellcome Inc.) and ALEC). These surfactant formulations are typically administered via airway instillation (i.e., after intubation) or intratracheally.

The agents of the present invention may be administered directly to the targeted tissue. Additionally and/or alternatively, the agent may be administered to a non-targeted area along with one or more agents that facilitate migration of the agent to (and/or uptake by) a targeted tissue, organ, or cell. While the targeted tissue can be any tissue subject to a fibrotic condition, preferred target tissues are lung tissue, heart tissue, liver tissue, brain tissue, kidney tissue, and the skin. As will be apparent to one of ordinary skill in the art, the therapeutic agent itself can be modified to facilitate its transport to (and uptake by) the desired tissue, organ, or cell. For example, histone lysine demethylases, EZH2 or YY-1 inhibitors, or histone deacetylase inhibitors can be modified as described above to facilitate their transport to a target cell, organ (e.g., lung), and/or tissue (e.g., lung tissue), including their transport across the blood-brain barrier; and/or their uptake by the target cell (e.g., its transport across cell membranes).

Exemplary delivery devices include, without limitation, nebulizers, atomizers, liposomes, transdermal patches, implants, implantable or injectable protein depot compositions, syringes, and gene therapy. Other delivery systems which are known to those of skill in the art can also be employed to achieve the desired delivery of the therapeutic agent to the desired organ, tissue, or cells in vivo to carry out this aspect of the present invention.

Any suitable approach for delivery of the agents can be utilized to practice this aspect of the present invention. Typically, the agent will be administered to a patient in a vehicle that delivers the agent(s) to the target cell, tissue, or organ.

One approach for delivering agents into cells involves the use of liposomes (including the surfactant formulations described above). Basically, this involves providing a liposome which includes agent(s) to be delivered, and then contacting the target cell, tissue, or organ with the liposomes under conditions effective for delivery of the agent into the cell, tissue, or organ.

Liposomes are vesicles comprised of one or more concentrically ordered lipid bilayers which encapsulate an aqueous phase. They are normally not leaky, but can become leaky if a hole or pore occurs in the membrane, if the membrane is dissolved or degrades, or if the membrane temperature is increased to the phase transition temperature. Current methods of drug delivery via liposomes require that the liposome carrier ultimately become permeable and release the encapsulated drug at the target site. This can be accomplished, for example, in a passive manner where the liposome bilayer degrades over time through the action of various agents in the body. Every liposome composition will have a characteristic half-life in the circulation or at other sites in the body and, thus, by controlling the half-life of the liposome composition, the rate at which the bilayer degrades can be somewhat regulated.

In contrast to passive drug release, active drug release involves using an agent to induce a permeability change in the liposome vesicle. Liposome membranes can be constructed so that they become destabilized when the environment becomes acidic near the liposome membrane (see, e.g., Wang & Huang, "pH-Sensitive Immunoliposomes Mediate Target-cell-specific Delivery and Controlled Expression of a Foreign Gene in Mouse," *Proc. Nat'l Acad. Sci. USA* 84:7851-5 (1987), which is hereby incorporated by reference in its entirety). When liposomes are endocytosed by a target cell, for example, they can be routed to acidic endosomes which will destabilize the liposome and result in drug release.

Alternatively, the liposome membrane can be chemically modified such that an enzyme is placed as a coating on the membrane, which enzyme slowly destabilizes the liposome. Since control of drug release depends on the concentration of enzyme initially placed in the membrane, there is no real effective way to modulate or alter drug release to achieve "on demand" drug delivery. The same problem exists for pH-sensitive liposomes in that as soon as the liposome vesicle comes into contact with a target cell, it will be engulfed and a drop in pH will lead to drug release.

This liposome delivery system can also be made to accumulate at a target organ, tissue, or cell via active targeting (e.g., by incorporating an antibody or hormone on the surface of the liposomal vehicle). This can be achieved according to known methods.

Different types of liposomes can be prepared according to Bangham et al., "Diffusion of Univalent Ions Across the Lamellae of Swollen Phospholipids," *J. Mol. Biol.* 13:238-52 (1965); U.S. Pat. No. 5,653,996 to Hsu; U.S. Pat. No. 5,643,599 to Lee et al.; U.S. Pat. No. 5,885,613 to Holland et al.; U.S. Pat. No. 5,631,237 to Dzau & Kaneda; and U.S. Pat. No. 5,059,421 to Loughrey et al., which are hereby incorporated by reference in their entirety.

These liposomes can be produced such that they contain, in addition to the therapeutic agents of the present invention, other therapeutic agents, such as anti-inflammatory agents, which would then be released at the target site (e.g., Wolff et al., "The Use of Monoclonal Anti-Thy1 IgG1 for the Targeting of Liposomes to AKR-A Cells in vitro and in vivo," *Biochim. Biophys. Acta* 802:259-73 (1984), which is hereby incorporated by reference in its entirety).

An alternative approach for delivery of proteins or polypeptide agents (e.g., histone lysine demethylases) involves the conjugation of the desired protein or polypeptide to a polymer that is stabilized to avoid enzymatic degradation of the conjugated protein or polypeptide. Conjugated proteins or polypeptides of this type are described in U.S. Pat. No. 5,681,811 to Ekwuribe, which is hereby incorporated by reference in its entirety.

Yet another approach for delivery of proteins or polypeptide agents involves preparation of chimeric proteins according to U.S. Pat. No. 5,817,789 to Heartlein et al., which is hereby incorporated by reference in its entirety. The chimeric protein can include a ligand domain and the polypeptide agent (e.g., histone lysine demethylase or dominant negative YY-1). The ligand domain is specific for receptors located on a target cell. Thus, when the chimeric protein is delivered intravenously or otherwise introduced into blood or lymph, the chimeric protein will adsorb to the targeted cell, and the targeted cell will internalize the chimeric protein.

Nucleic acid agents (including RNA and DNA) for use in the methods of the present invention can be delivered to a subject in a number of ways known in the art, including through the use of gene therapy vectors and methods as described above. The nucleic acid can be contained within a vector useful for gene therapy, for example, a vector that can be transferred to the cells of a subject and provide for expression of the therapeutic nucleic acid agent therein. Such vectors include chromosomal vectors (e.g., artificial chromosomes), non-chromosomal vectors, and synthetic nucleic acids. Vectors include plasmids, viruses, and phages, such as retroviral vectors, lentiviral vectors, adenoviral vectors, and adeno-associated vectors.

Nucleic acid agents can be transferred into a subject using ex vivo or in vivo methods. Ex vivo methods involve transfer of the nucleic acid into cells in vitro (e.g., by transfection, infection, or injection) that are then transferred into or administered to the subject. The cells can be, for example, cells derived from the subject (e.g., lymphocytes) or allogeneic cells. For example, the cells can be implanted directly into a specific tissue of the subject or implanted after encapsulation within an artificial polymer matrix. Examples of sites of implantation include the lungs or airways, skin, conjunctiva, central nervous system, peripheral nerve, a grafted kidney, or an inflamed joint. Nucleic acids can also be delivered into a subject in vivo. For example, nucleic acids can be administered in an effective carrier, e.g., any formulation or composition capable of effectively delivering the nucleic acid to cells in vivo. Nucleic acids contained within viral vectors can be delivered to cells in vivo by infection or transduction using virus. Nucleic acids and vectors can also be delivered to cells by physical means, e.g., by electroporation, lipids, cationic lipids, liposomes, DNA gun, calcium phosphate precipitation, injection, or delivery of naked nucleic acid.

As an alternative to non-infective delivery of nucleic acids as described above, naked DNA or infective transformation vectors can be used for delivery, whereby the naked DNA or infective transformation vector contains a recombinant gene that encodes, for example, the histone lysine demethylase or the dominant negative YY-1 or EZH2 proteins, of the present invention. The nucleic acid molecule is then expressed in the transformed cell.

The recombinant gene includes, operatively coupled to one another, an upstream promoter operable in mammalian cells and optionally other suitable regulatory elements (i.e., enhancer or inducer elements), a coding sequence that encodes the therapeutic nucleic acid (described above), and a downstream transcription termination region. Any suitable constitutive promoter or inducible promoter can be used to regulate transcription of the recombinant gene, and one of skill in the art can readily select and utilize such promoters, whether now known or hereafter developed. The promoter can also be specific for expression in cells that express YY-1 or EZH2. Tissue specific promoters can also be made inducible/repressible using, e.g., a TetO response element. Other inducible elements can also be used. Known recombinant techniques can be utilized to prepare the recombinant gene, transfer it into the expression vector (if used), and administer the vector or naked DNA to a patient. Exemplary procedures are described in JOSEPH SAMBROOK et al., 1-3 MOLECULAR CLONING: A LABORATORY MANUAL (2d ed. 1989), which is hereby incorporated by reference in its entirety. One of skill in the art can readily modify these procedures, as desired, using known variations of the procedures described therein.

Any suitable viral or infective transformation vector can be used. Exemplary viral vectors include, without limitation, adenovirus, adeno-associated virus, and retroviral vectors (including lentiviral vectors).

Adenovirus gene delivery vehicles can be readily prepared and utilized given the disclosure provided in Berkner, "Development of Adenovirus Vectors for the Expression of Heterologous Genes," *Biotechniques* 6:616-29 (1988); Rosenfeld et al., "Adenovirus-mediated Transfer of a Recombinant α 1-Antitrypsin Gene to the Lung Epithelium in vivo," *Science* 252:431-434 (1991); International Patent Publication No. WO 1993/007283 to Curiel et al.; International Patent Publication No. WO 1993/006223 to Perricaudet et al.; and International Patent Publication No. WO 1993/007282 to Curiel et al., which are hereby incorporated by reference in their entirety. Additional types of adenovirus vectors are described in U.S. Pat. No. 6,057,155 to Wickham et al., U.S. Pat. No. 6,033,908 to Bout & Hoeben, U.S. Pat. No. 6,001,557 to Wilson et al., U.S. Pat. No. 5,994,132 to Chamberlain & Kumar-Singh, U.S. Pat. No. 5,981,225 to Kochanek & Schniedner, U.S. Pat. No. 5,885,808 to Spooner & Epenetos, and U.S. Pat. No. 5,871,727 to Curiel, which are hereby incorporated by reference in their entirety.

Adeno-associated viral gene delivery vehicles can be constructed and used to deliver into cells a recombinant gene encoding a desired nucleic acid. The use of adeno-associated viral gene delivery vehicles in vitro is described in Chatterjee et al., "Dual-Target Inhibition of HIV-1 in vitro by Means of an Adeno-associated Virus Antisense Vector," *Science* 258: 1485-8 (1992); Walsh et al., "Regulated High Level Expression of a Human γ-Globin Gene Introduced into Erythroid Cells by an Adeno-associated Virus Vector," *Proc. Nat'l Acad. Sci. USA* 89:7257-61 (1992); Walsh et al., "Phenotypic Correction of Fanconi Anemia in Human Hematopoietic Cells with a Recombinant Adeno-associated Virus Vector," *J. Clin. Invest.* 94:1440-8 (1994); Flotte et al., "Expression of the Cystic Fibrosis Transmembrane Conductance Regulator from a Novel Adeno-associated Virus Promoter," *J. Biol. Chem.* 268:3781-90 (1993); Ponnazhagan et al., "Suppression of Human α-Globin Gene Expression Mediated by the Recombinant Adeno-associated Virus 2-based Antisense Vectors," *J. Exp. Med.* 179:733-8 (1994); Miller et al., "Recombinant Adeno-associated Virus (rAAV)-mediated Expression of a Human γ-Globin Gene in Human Progenitor-derived Erythroid Cells," *Proc. Nat'l Acad. Sci. USA* 91:10183-7 (1994); Einerhand et al., "Regulated High-level Human β-Globin Gene Expression in Erythroid Cells Following Recombinant Adeno-associated Virus-mediated Gene Transfer," *Gene Ther.* 2:336-43 (1995); Luo et al., "Adeno-associated Virus 2-mediated Gene Transfer and Functional Expression of the Human Granulocyte-macrophage Colony-stimulating Factor," *Exp. Hematol.* 23:1261-7 (1995); and Zhou et al., "Adeno-associated Virus 2-mediated Transduction and Erythroid Cell-specific Expression of a Human β-Globin Gene," *Gene Ther.* 3:223-9 (1996), which are hereby incorporated by reference in their entirety. In vivo use of these vehicles is described in Flotte et al., "Stable in vivo Expression of the Cystic Fibrosis Transmembrane Conductance Regulator with an Adeno-associated Virus Vector," *Proc. Nat'l Acad. Sci. USA* 90:10613-7 (1993), and Kaplitt et al., "Long-term Gene Expression and Phenotypic Correction Using Adeno-associated Virus Vectors in the Mammalian Brain," *Nat. Genet.* 8:148-54 (1994), which are hereby incorporated by reference in their entirety.

Retroviral vectors which have been modified to form infective transformation systems can also be used to deliver a recombinant gene encoding a desired nucleic acid product into a target cell. One such type of retroviral vector is disclosed in U.S. Pat. No. 5,849,586 to Kriegler & Perez, which is hereby incorporated by reference in its entirety. Lentivirus vectors can also be utilized, including those described in U.S. Pat. No. 6,790,657 to Arya, U.S. Patent Application Publication No. 2004/0170962 to Kafri et al., and U.S. Patent Application Publication No. 2004/0147026 to Arya, which are hereby incorporated by reference in their entirety.

Inhibitory RNA can be administered to the subject systemically or locally as described above. Delivery of inhibitory RNA is preferably administered alone or as a component of a composition of the present invention. Suitable compositions include the siRNA formulated or complexed with polyethylenimine (e.g., linear or branched PEI) and/or polyethylenimine derivatives, including for example grafted PEIs such as galactose PEI, cholesterol PEI, antibody derivatized PEI, and polyethylene glycol PEI derivatives thereof (see, e.g., Blazek-Welsh & Rhodes, "Maltodextrin-based Proniosomes," *AAPS Pharm. Sci.* 3(1):1-11 (2001); Furgeson et al., "Modified Linear Polyethylenimine-cholesterol Conjugates for DNA Complexation," *Bioconjug. Chem.* 14:840-7 (2003); Kunath et al., "The Structure of PEG-modified Poly(Ethylene Imines) Influences Biodistribution and Pharmacokinetics of Their Complexes with NF-κB Decoy in Mice," *Pharm. Res.* 19:810-7 (2002); Choi et al., "Effect of Poly(Ethylene Glycol) Grafting on Polyethylenimine as a Gene Transfer Vector in vitro," *Bull. Korean Chem. Soc.* 22(1):46-52 (2001); Bettinger et al., "Size Reduction of Galactosylated PEI/DNA Complexes Improves Lectin-mediated Gene Transfer into Hepatocytes," *Bioconjug. Chem.* 10:558-61 (1999); Petersen et al., "Polyethylenimine-graft-poly(ethylene glycol) Copolymers: Influence of Copolymer Block Structure on DNA Complexation and Biological Activities as Gene Delivery System," *Bioconjug. Chem.* 13:845-54 (2002); Erbacher et al., "Transfection and Physical Properties of Various Saccharide, Poly(Ethylene Glycol), and Antibody-derivatized Polyethylenimines (PEI)," *J. Gene Med.* 1(3):210-22 (1999); Godbey et al., "Tracking the Intracellular Path of Poly(Ethylenimine)/DNA Complexes for Gene Delivery," *Proc. Nat'l Acad. Sci. USA* 96:5177-81 (1999); Godbey et al., "Poly (Ethylenimine) and Its Role in Gene Delivery," *J. Control. Release* 60:149-60 (1999); Diebold et al., "Mannose Polyethylenimine Conjugates for Targeted DNA Delivery into Dendritic Cells," *J. Biol. Chem.* 274:19087-94 (1999); Thomas & Klibanov, "Enhancing Polyethylenimine's Delivery of Plasmid DNA into Mammalian Cells," *Proc. Nat'l Acad. Sci. USA* 99:14640-5 (2002); U.S. Pat. No. 6,586,524 to Sagara, which are hereby incorporated by reference in their entirety).

The inhibitory RNA molecule can also be present in the form of a bioconjugate, for example a nucleic acid conjugate as described in U.S. Pat. No. 6,528,631 to Cook et al., U.S. Pat. No. 6,335,434 to Guzaev et al., U.S. Pat. No. 6,235,886 to Manoharan & Cook, U.S. Pat. No. 6,153,737 to Manoharan et al., U.S. Pat. No. 5,214,136 to Lin & Matteucci, and U.S. Pat. No. 5,138,045 to Cook & Guinosso, which are hereby incorporated by reference in their entirety.

The inhibitory RNA, or any composition or bioconjugate containing the same, can be administered via a liposomal delivery mechanism described above.

Many routes of delivery are known to the skilled artisan for delivery of anti-target antibodies. For example, direct injection may be suitable for delivering the antibody to the site of interest. It is also possible to utilize liposomes with antibodies in their membranes to specifically deliver the liposome to the area where H3K27 trimethylation is to be reduced or EZH2 or YY-1 expression or activity is to be inhibited. These liposomes can be produced such that they contain, in addition to monoclonal antibody, other therapeutic agents, such as those described above, which would then be released at the target site.

Administration can be carried out as frequently as required and for a duration that is suitable to provide effective treatment for a fibrotic condition being treated or prevented. For example, administration can be carried out with a single sustained-release dosage formulation or with multiple daily doses. Where more than one of the above described agents is administered, they may be administered at the same time (e.g., present in the same pharmaceutical formulation), or separately (e.g., each present in a separate pharmaceutical formulation) but during the same course of treatment. Administration can be carried out before, concurrently with, and/or after the appearance of symptoms of the fibrotic condition.

The amount to be administered will, of course, vary depending upon the treatment regimen. Generally, an agent is administered to achieve an amount effective for amelioration of, or prevention of the development of symptoms of, the fibrotic condition (i.e., a therapeutically effective amount). Thus, a therapeutically effective amount can be an amount which is capable of at least partially preventing or reversing the fibrosis related condition. The dose required to obtain an effective amount may vary depending on the agent, formulation, disease or disorder, and individual to whom the agent is administered.

Determination of effective amounts may also involve in vitro assays in which varying doses of agent are administered to cells in culture and the concentration of agent effective for ameliorating some or all symptoms is determined in order to calculate the concentration required in vivo. Effective amounts may also be based on in vivo animal studies. A therapeutically effective amount can be determined empirically by those of skill in the art.

By way of example, the histone lysine demethylase can be administered in an amount between about 500 µg/kg and about 2.5 mg/kg, preferably between about 750 µg/kg and about 2.25 mg/kg, more preferably between about 1 mg/kg and 2 mg/kg Inhibitors of EZH2, YY-1, and histone deacetylase can be administered in an amount between about 500 µg/kg and about 10 mg/kg, preferably between about 750 µg/kg and about 5 mg/kg. In the case of EZH2 or YY-1 siRNA or shRNA, the amount is preferably between about 25 nmol/kg and 10 mmol/kg, more preferably between about 100 nmol/kg and about 5 mmol/kg.

Another aspect of the present invention relates to a method of identifying an agent that is effective for treating a fibrotic condition. This method involves obtaining a first biological sample from an in vivo or in vitro experimental model of fibrosis and administering a candidate agent to the in vivo or in vitro experimental model of fibrosis. A second biological sample is obtained from the experimental model after administering the candidate agent, and the level of H3K27 trimethylation in the first and second biological samples is measured. The level of H3K27 trimethylation in the first and second biological samples is then compared. A decrease in the level of H3K27 trimethylation in the second biological sample relative to the level of H3K27 trimethylation in the first biological sample indicates that the agent is effective for treating a fibrotic condition.

In vivo models of fibrosis are well known in the art. For example, fibrosis can be induced in vivo upon intratracheal instillation of bleomycin, fluorescein isothiocyanate, irradiation, silica, or particulate matter in an animal. Additionally, a fibrotic condition is displayed in transgenic animals overexpressing TGF-β and upon adoptive transfer of human fibrotic fibroblasts into immunodeficient animals (Moore et al., "Murine Models of Pulmonary Fibrosis," *Am. J. Physiol. Lung Cell Mol. Physiol.* 294:L152-60 (2008); Gharaee-Kermani et al., "Animal Models of Pulmonary Fibrosis," *Methods Mol. Med.* 117:251-9 (2005), which are hereby incorporated by reference in their entirety). In one embodiment of this aspect of the present invention, the in vivo experimental model of fibrosis is a silica-treated mouse model as described herein.

In vitro models of fibrosis are also well known in the art. Typically, an in vitro model of fibrosis comprises an isolated tissue or cell sample derived directly from fibrotic condition, for example, lung fibroblasts derived from patients having lung fibrosis, as described herein. Alternatively, an in vitro model of fibrosis can comprises an isolated tissue or cell sample where a fibrotic phenotype is induced. Fibrotic phenotypes can be induced directly by exposure to exogenous agents, or indirectly by stimulation with cytokines and other inflammatory mediators of fibrosis. As described herein, exposing lung fibroblasts to silica directly stimulates a fibrotic phenotype in lung fibroblasts and provides a suitable in vitro model of pulmonary fibrosis for use in accordance with this aspect of the present invention.

As will be apparent to the skilled artisan, the method according to this aspect of the present invention can be used to identify agents effective for treating the fibrotic conditions described above. In a preferred embodiment, the fibrotic condition is lung or pulmonary fibrosis.

The present invention is illustrated, but not limited, by the following examples.

EXAMPLES

Example 1

Animals and Silica or Bleomycin Administration

YY1 heterozygotes (YY1$^{+/-}$) and conditional knockout YY1 (YY1$^{f/f}$) mice were obtained from Dr. Yang Shi (Harvard University, Boston, Mass.). All animals were grouped according to age (6-12) or weight (20-35 g). YY1$^{+/-}$ mice were on a C57BL/6 background (≥6 generations). YY1$^{f/f}$ mice were on a C57BL/6 background (4 generations). These mice received 200-300 µg of silica or three units of bleomycin per kg of body weight by intratracheal injection. The background of YY1$^{cc10}$ is F4 C57BL/6. All animals were housed under specific pathogen-free conditions at the NIH in an American Association for the Accreditation of Laboratory Animal Care-approved facility. The URMC animal care and use committee approved all experimental procedures.

Example 2

Construction of Clara Cell Promoter Driven YY1 (YY1$^{cc10}$)

CC-10-driven YY1 (YY1$^{cc10}$) mice were generated as follows. The plasmid of a rat cc10 promoter (kind gift of Dr. Z. Zhou, Johns Hopkins University) was digested with XbaI-BamHI and the DNA ends were blunted. The murine YY1 gene was digested with BamHI and the DNA ends were blunted. A YY1 insert was subcloned into a blunted rat cc10 plasmid and the plasmid was digested with HindIII and KpnI. The 4 Kb fragment was obtained and injected into zygotes of BJ6 strain to create transgenic mice. Three lines were generated and genotyping was performed using the forward primer 5'-ACTGCCCATTGCCCAAACAC (SEQ ID NO:7) and the reverse primer 5'-GATGGTCTCCACCTCGATCTCATG (SEQ ID NO:8).

Example 3

Cell Lines and Isolation of Primary Mouse Lung Fibroblasts

WI-38 cells (human fetal lung fibroblasts), MLg2908 cells (mouse lung fibroblasts), LL97A cells (human adult lung fibroblasts obtained from a patient with idiopathic pulmonary fibrosis), and MRC-5 (secondary human lung fibroblasts) were all purchased from the American Type Culture Collection. 293FT cells were obtained from Invitrogen. Primary mouse lung fibroblasts were isolated as described in Baglole et al., "Isolation and Phenotypic Characterization of Lung Fibroblasts," *Meth. Mol. Med.* 117:115-27 (2005), which is hereby incorporated by reference in its entirety. Briefly, lungs were minced and digested with collagenase and DNase at 37° C. for two hours. After washing with HBSS, isolated cells were collected by centrifugation and plated in T75 flasks in DMEM/F12 (1:1) containing 10% FBS and antibiotics. This was completed in a humidified atmosphere consisting of 5% $CO_2$ and 95% air overnight. Non-adherent cells were removed by washing the flask with media. After the third passage, the primary lung fibroblasts were used for the experiments.

Example 4

Histopathological and Immunohistochemical Examination

Lungs were fixed with 10% buffered formalin and embedded in paraffin. H&E stains and Masson's Trichrome stains were used for analysis of pathological changes using the Accustain Trichrome Stain Kit (Sigma Chemical Co., St. Louis, Mo.). Immunohistochemical staining for α-SMA and YY1 in tissues was performed according to the instructions provided in the Animal Research Kit (DAKO Cytomation). Briefly, lung sections were deparaffinized, incubated with hot 5% urea to retrieve antigen, blocked, and stained with primary antibodies overnight at 4° C. After application of the appropriate secondary antibody, streptavidin-conjugated horseradish peroxidase (HRP-Streptavidin) was applied, and staining was visualized with NovaRed (Vector Laboratories). Slides were counterstained with hematoxylin for determination of α-SMA expression. The severity of fibrosis was evaluated in stained sections by an individual who was blinded to the genotypes of the mice. Double staining kits were purchased from Biocare Medical (Concord, Calif.) and staining was carried out following the recommended protocols.

Example 5

Quantitative PCR

Total RNA from lung tissue and lung fibroblasts was extracted using TRIzol® reagent (Invitrogen). Then, 0.5-1 μg of total RNA was reverse-transcribed using oligo dT as a primer. Quantitative PCR was performed using an iQ5 Biorad device. Data were analyzed by the $2^{-\Delta(\Delta/C_T)}$ method and normalized to the expression of the GAPDH housekeeping gene. The sequences of the primers utilized are listed in Table 1.

TABLE 1

Primer Pairs Used for Quantitative PCR

| Gene | Forward (5'-3') | Reverse (5'-3') |
|---|---|---|
| YY1 | ACGCTGGTCACCGTGGCGGC (SEQ ID NO: 9) | TTGCCGCTCTTCTTGCCGCC (SEQ ID NO: 10) |
| α-SMA | CATGCCATCATGCGTCTGGACTTG (SEQ ID NO: 11) | ACGAAGGAATAGCCACGCTCAG (SEQ ID NO: 12) |
| Collagen I | TGCCAATGGTGCTCCTGGTATTGC (SEQ ID NO: 13) | GAGCACCAGGTTCACCACTGTT (SEQ ID NO: 14) |
| GAPDH | GCCACCCAGAAGACTGTGGAT (SEQ ID NO: 15) | GAAGGCCATGCCAGTGAGCT (SEQ ID NO: 16) |

Example 6

Immunofluorescent Staining

Primary lung fibroblasts from $YY1^{cc10}$, wild type, and $YY1^{f/f}$ mice were transfected with Cre-GFP, or LL97A cells derived from human fibroblasts obtained from IPF patients were transduced with YY1 shRNA, and were plated in four-well chamber slides. Cells were supplemented with DMEM and 10% FBS at 37° C. for four days. Cells were fixed with 4% paraformaldehyde, permeabilized with 0.1% PBS-Triton-100, blocked with protein block serum-free solution (DAKO Cytomation), and incubated with anti-α-SMA antibody (1A4, DAKO Cytomation) for one hour at room temperature. They were then incubated with secondary antibody (goat anti-mouse Alexa Fluor 488, Invitrogen) for one hour at room temperature. Incubation with anti-YY1 antibody (H-414, Santa Cruz) was performed at 4° C. overnight. Secondary antibody (goat anti-rabbit Texas Red-X, Invitrogen) was used for one hour at room temperature. Stained cells were embedded in mounting medium with DAPI (Invitrogen) and examined with a Zeiss fluorescence microscope.

Example 7

Western Blot Analysis

Cells or lung tissues were solubilized in lysis buffer (50 mM Tris/HCl (pH 8.0), 150 mM NaCl, 0.1% SDS, 0.5% sodium deoxycholate, 0.02% $Na_3N$, 1% Nonidet P40, 1 mM PMSF, and 2 μg/ml aprotinin). Protein concentrations were determined by a BCA assay. Protein samples (20 μg) were separated in 8-16% SDS/PAGE gels and transferred onto a nitrocellulose membrane. The membrane was incubated with primary antibodies diluted in 1% non-fat milk in PBS containing 0.1% Tween 20, followed by incubation with horseradish peroxidase-conjugated IgG as the secondary antibody. Visualization was carried out using an ECL (enhanced chemiluminescence) kit.

Example 8

Luciferase Assay and Construct of YY1 and α-SMA Luciferase Reporter

Plasmids containing only the YY1 promoter (or a YY1 promoter with a mutant NF-κB binding site driving a luciferase reporter gene) were kindly provided by Dr. Denis C. Guttridge (Ohio State University). To construct the α-SMA-luciferase reporter plasmid, the α-SMA promoter was amplified by PCR using primers M_SMA-5'-

CCCGCTCGAGATGGTCCTTAATCATGCT (SEQ ID NO:17) and M_SMA-5'-CCCAAGCTTCTTACCCTGA-CAGCGACTGG (SEQ ID NO:18). Amplification was completed using mouse lung fibroblast genomic DNA. The DNA was cut with XhoI and HindIII and subcloned into the XhoI and HindIII sites of the pGL3 basic vector (Promega). The reporter constructs were transiently transfected into WI-38 cells, MLg2908 cells, and primary lung fibroblast of YY1$^{+/-}$ and wild type mice using electroporation (300V 1050 Capacitance). These plasmids included YY1-Luc, mutant YY1-Luc, and α-SMA-Luc. The transfected cells were placed in OPTI-MEM media containing 0.1% FBS overnight in 24-well plates, and were then stimulated with TGF-β for 24 hours or with TNF-α for 6 hours. Using the same procedure, a p65 (NF-κB) plasmid was cotransfected with YY1-Luc, mutant YY1-Luc, or YY1 with or without a p65 plasmid and α-SMA-Luc.

Example 9

Lentiviral shRNA, Lentiviral-Cre, and Adenoviral-Cre

Constructs used for depletion of YY1 shRNA were obtained from Open Biosystems (Huntsville, Ala.). For each gene, five pre-made shRNA constructs were obtained and tested. The constructs were used to identify genes capable of achieving efficient knockdown of YY1 at the protein level. Negative control constructs for the same vector system (vector alone, scrambled, and luciferase shRNA) were created in Dr. Jia Guo's lab (University of Rochester, Rochester, N.Y.). The lentiviral helper plasmids pHR'8.9ΔR and pCMV-VSV-G were obtained from Dr. Linzhao Chen (Johns Hopkins University). All plasmids were prepped, and their integrity was confirmed by restriction analysis. To prepare transient virus stocks, 1.0×10$^6$ 293T cells were plated in 60-mm dishes. The next day, the cells were cotransfected with shRNA constructs (1.5 μg) along with pHR'8.9ΔR and pCMV-VSV-G helper constructs (1.5 μg and 0.3 μg, respectively) using FuGENE 6 (Roche, Indianapolis, Ind.), and the medium was changed the following day. One day later, virus-containing media was harvested. The viral stocks were centrifuged and filtered to remove any nonadherent 293T cells. Next, WI-38 and LL97A cells were infected with shRNA lentiviruses. To accomplish this, cells were plated at subconfluent densities and infected one day later with a cocktail of one ml of virus-containing medium, three ml of regular medium, and eight μg/ml of Polybrene. The medium was changed one day after infection. Selective medium was added two days post-infection (two μg/ml of puromycin for WI-38 and LL97A cells). After three days of puromycin selection, the mock-infected cells had all died. Stably-infected pooled clones were then studied. The shRNA sequences are listed in Table 2 below.

TABLE 2

Lentiviral shRNA Sequences

Control-shRNA-1

Sense 5'-3'
CCGGGCAGCTGCCAGATAGCATGAACTCGAGTTCATGCTATCTGGCAGCT
GCTTTTTG (SEQ ID NO: 19)

Antisense 5'-3'
AATTCAAAAAGCAGCTGCCAGATAGCATGAACTCGAGTTCATGCTATCTG
GCAGCTGC (SEQ ID NO: 20)

TABLE 2-continued

Lentiviral shRNA Sequences

Control-shRNA-2

Sense 5'-3'
CCGGCGTACGCGGAATACTTCGACTCGAGTCGAAGTATTCCGCGTACGTT
TTTG (SEQ ID NO: 21)

Antisense 5'-3'
CAAAAACGTACGCGGAATACTTCGACTCGAGTCGAAGTATTCCGCGTACG
CCGG (SEQ ID NO: 22)

YY1-shRNA-1

Sense 5'-3'
CCGGGCCCTCATAAAGGCTGCACAACTCGAGTTGTGCAGCCTTTATGAGG
GCTTTTTG (SEQ ID NO: 23)

Antisense 5'-3'
CAAAAAGCCCTCATAAAGGCTGCACAACTCGAGTTGTGCAGCCTTTATGA
GGGCCCGG (SEQ ID NO: 24)

YY1-shRNA-2

Sense 5'-3'
CCGGGTGGTTGAAGAGCAGATCATTCTCGAGAATGATCTGCTCTTCAACC
ACTTTTTG (SEQ ID NO: 25)

Antisense 5'-3'
CAAAAAGTGGTTGAAGAGCAGATCATTCTCGAGAATGATCTGCTCTTCAA
CCACCCGG (SEQ ID NO: 26)

Lung fibroblasts isolated from YY1$^{f/f}$ mice were transduced with Lenti-Cre at different multiplicities of infection (MOI) to knockdown YY1 expression. Extracts from whole cells were immunoblotted with anti-YY1 antibody. The Lenti-Cre vector was purchased from Addgene. The packaging and infection approach employed was the same as that described above.

Adenoviral Cre was purchased from Biomicrobics System Inc. (Canada) in 6×10$^9$ pfu.

Example 10

Statistical Analysis

Quantitative PCR, YY1 and α-SMA promoter reporter assay, and histological score of lung fibrosis were analyzed for statistical significance by using the paired Student's t-test using Microsoft Excel software. A p value of <0.05 was considered statistically significant.

Example 11

Purification of Primary Lung Fibroblasts

Anti-S100A4 (anti-FSP1, AB68124) was purchased from Abcam and anti-mouse-APC (A21057) was purchased from Invitrogen. Primary lung fibroblasts were isolated from mice treated with bleomycin (3 U/kg). After incubation with F12 10% FBS medium for a week, the fibroblasts were labeled following Abcam intracellular staining and indirect labeling protocols. The protocol can produce about 90% purity of lung fibroblasts.

Example 12

Evaluation of YY1 Up-Regulation by TGF-β in MRC5 Human Adult Fibroblasts

Whether YY1 is up-regulated by TGF-β in adult fibroblasts was investigated using a human adult fibroblast cell line, MRC5. After serum starvation for 24 hours, MRC5 cells were treated with 10 ng/ml of TGF-β for 8 hours or 24 hours in serum-free DMEM. Extracts from whole cells treated with TGF-β for 8 hours were subjected to immunoblot analysis with anti-YY1 or anti-β-actin antibody. YY1 expression was found to be up-regulated by TGF-β stimulation. MRC5 cells transfected with the full-length YY1 promoter-luciferase reporter (YY1-LUC) by electroporation were treated with PBS or TGFβ for 24 hours, and the relative light units (RLU) were measured with a luminometer. YY1-LUC was also found to be up-regulated TGF-β stimulation.

Example 13

YY1 Binding Activity at the α-SMA Promoter in Nuclear Extracts from WI-38 Cells

Nuclear extracts from WI-38 cells were prepared as described in Kurisaki et al., "Nuclear Factor YY1 Inhibits Transforming Growth Factor β- and Bone Morphogenetic Protein-Induced Cell Differentiation," *Mol. Cell Biol.* 23(13): 4494-510 (2003), which is hereby incorporated by reference in its entirety. The protein concentration was determined by BCA (Pierce) using bovine serum albumin as a standard. Double-stranded DNA probes were prepared by annealing the oligonucleotides 5'-3' TCAGTTCCTGGTTTCATTAC-TACAACACAA (SEQ ID NO:27) (sense) and 5'-3' TTGT-GTTGTAGTAATGAAACCAGGAACAGA (SEQ ID NO:28) (antisense). The sense oligonucleotide was 5'-end-labeled with biotin during oligonucleotide synthesis (IDT). Protein binding reactions were carried out in 20 ml of buffer (20 mM Hepes pH 7.9, 80 mM KCl, 5 mM $MgCl_2$, 2% (v/v) Ficoll, 5% (v/v) Glycerol, 0.1 mM EDTA, 1 mM Dithiothreitol) with 20 fmole of biotinylated probe, 1 mg of poly dIdC, 50 mg of Bovine serum albumin, and 5 mg of lung fibroblast nuclear protein. The mixture was incubated for 30 minutes at room temperature in the presence or absence of non-labeled competitor oligonucleotides. For super-shift assays, the binding reaction mixture was pre-incubated with YY1 antibodies (1703, Santa Cruz Biotechnology). The protein DNA complexes were resolved by electrophoresis (6% non-denaturing polyacrylamide gel from Invitogen) in 0.5×TBE running buffer. The results identify a YY1 binding site located on the α-SMA protomer at residues −556 to −526. (A potential second binding site is located at residues −279 to −249.)

Example 14

Cytokine Profile 1 ml of bronchoalveolar lavage ("BAL") was obtained from wild type and $YY1^{+/-}$ mice. Cytokines from BALs were measured using a Bio-Plex array (8-plex cytokines) from Bio-Rad. Some cytokines, such as IL-12, IFN-γ, and TNF-α, were significantly decreased in BAL of $YY1^{+/-}$ mice compared to that of wild type mice.

Example 15

Figure 1B:
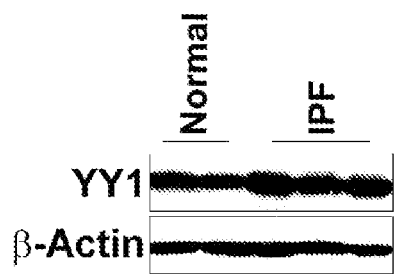
Figure 1C:
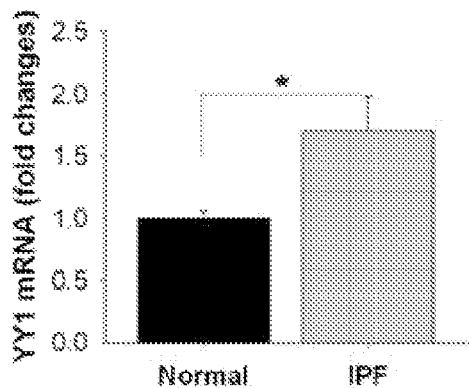
Figure 2A:
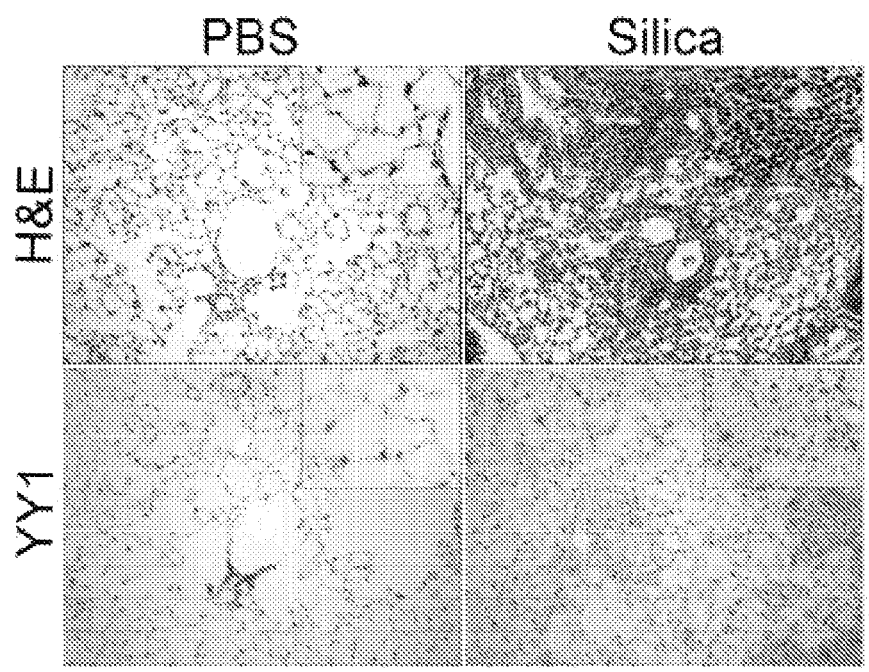
FIGS. 2A-2C show that YY1 protein expression is increased in the lungs of silica-challenged mice.
Figure 2B:
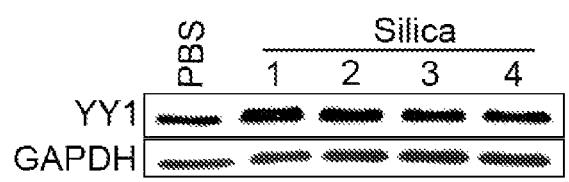
Figure 3A:
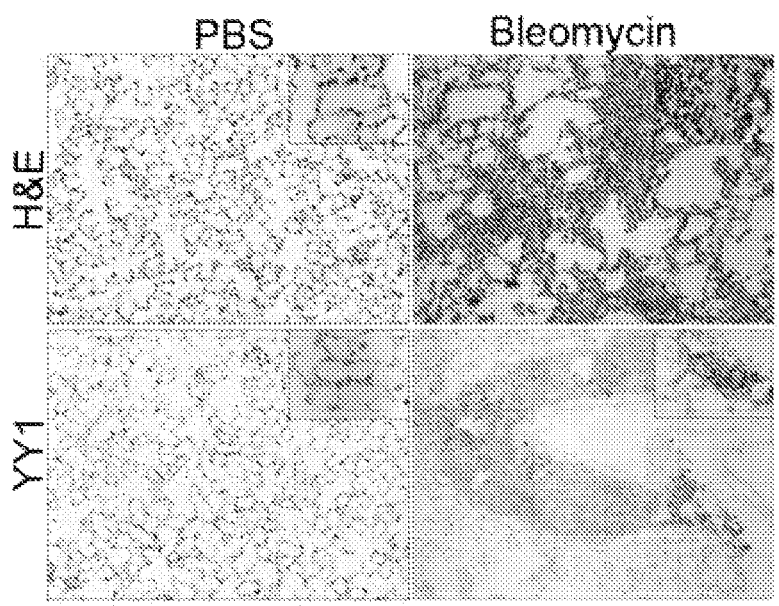
FIGS. 3A-3C show that YY1 protein expression is increased in the lungs of bleomycin-challenged mice.
Figure 3B:
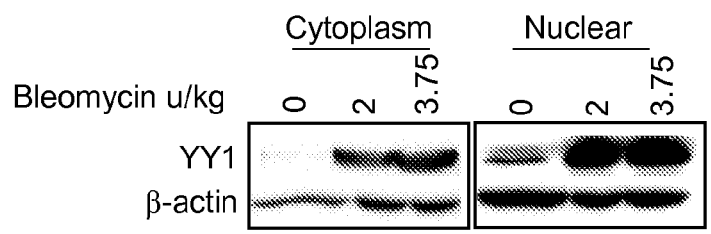
Figure 3C:
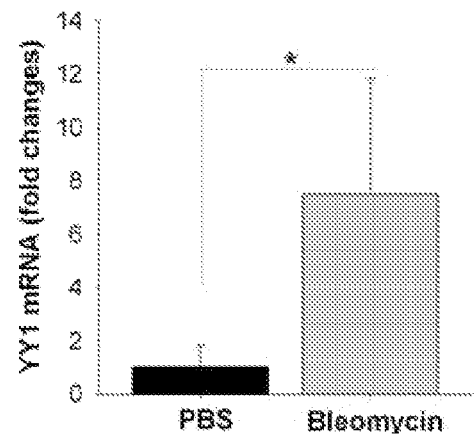

YY1 Expression is Increased in Lung Tissues Obtained from Humans with Idiopathic Pulmonary Fibrosis (IPF), as Well as in Silica and Bleomycin-Exposed Mice To determine whether YY1 is induced in human IPF (FIGS. 1A-1C) and the silica and bleomycin mouse models of lung fibrosis (FIGS. 2A-2B (silica) and FIGS. 3A-3C (bleomy-cin)), immunohistochemistry and immunoblot assays were performed with anti-YY1 and anti-S100A (also called fibroblast specific protein 1, FSP1) antibodies. YY1 was markedly increased in lung fibroblasts of fibrotic areas of human IPF, as shown in FIG. 1A, and in mouse lung models following silica or bleomycin instillation, as shown in FIG. 2A (silica instal-lation) and FIG. 3A (bleomycin installation).

Figure 2C:
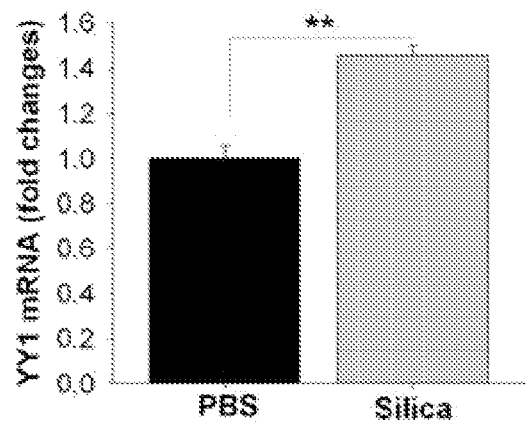

Immunohistochemistry localized YY1 expression to bronchial epithelial cells and fibroblast foci in human IPF and in mice with induced fibrosis. Immunoblot analysis confirmed that total YY1 expression was upregulated in the human IPF lung, as shown in FIG. 1B, as well as in silica and bleomycin mouse models, as shown in FIG. 2B (silica mouse model) and FIG. 3B (bleomycin mouse model). Using quantitative PCR, it was found that YY1 transcript levels were increased both in lungs obtained from subjects with IPF, as shown in FIG. 1C, as well as silica- and bleomycin-exposed mice, as shown in FIG. 2C (silica-exposed) and FIG. 3C (bleomycin-exposed). Taken together, these findings indicate that lung fibrotic responses are associated with enhanced expression of both YY1 mRNA and protein. Next, the cell types expressing YY1 were explored in more detail.

Example 16

YY1 Is Overexpressed in Lung Fibroblasts in Human IPF and Murine Silicosis

Figure 4A:
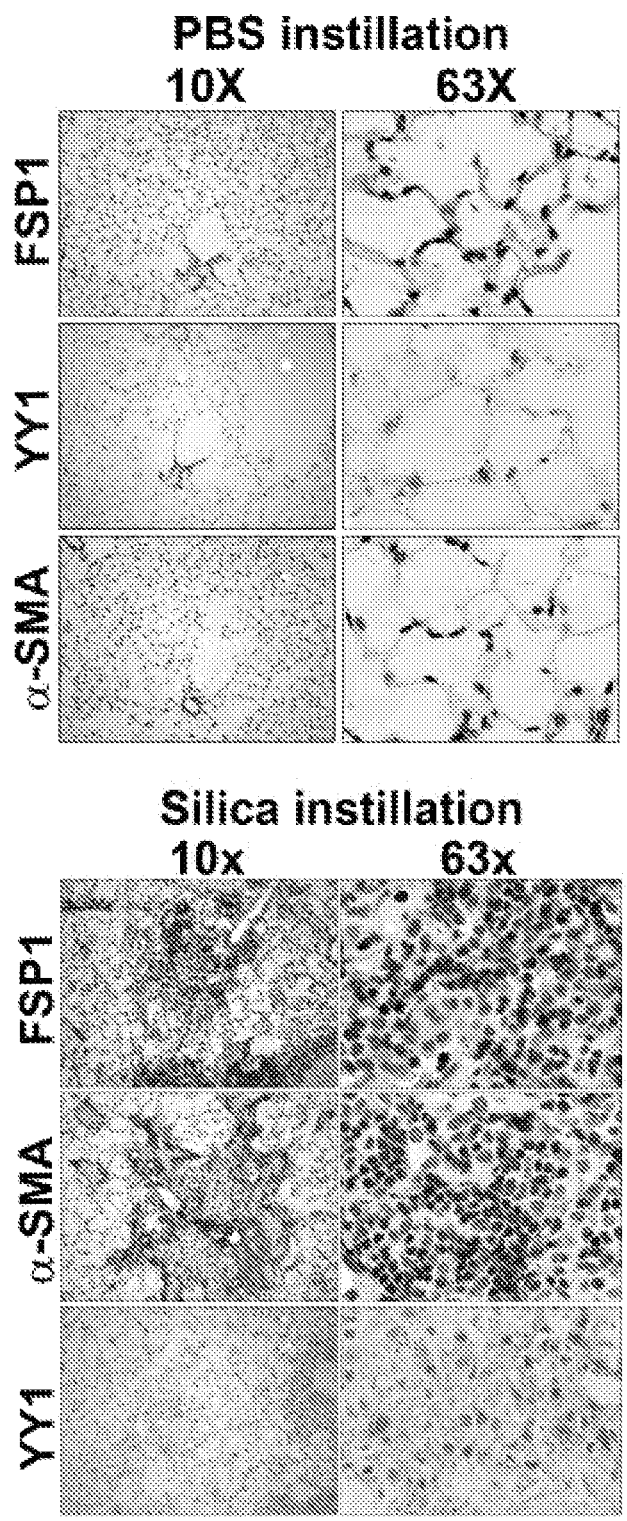
FIG. 4A is a series of light photomicrographs of lung sections from C57BL/6 mice instilled with saline ("PBS") or silica and evaluated 21 days after silica treatment (the YY1-labeled samples are same the same as those shown in FIG. 2A). Samples were stained with anti-YY1, anti-α-SMA, and anti-FSP1. The expression of YY1 and α-SMA were increased in FSP1 positive cells in mouse silicosis compared to PBS instillation control. Magnification was 10× (left panels) and 63× (right panels). All experiments were performed at least three times.
Figure 4B:
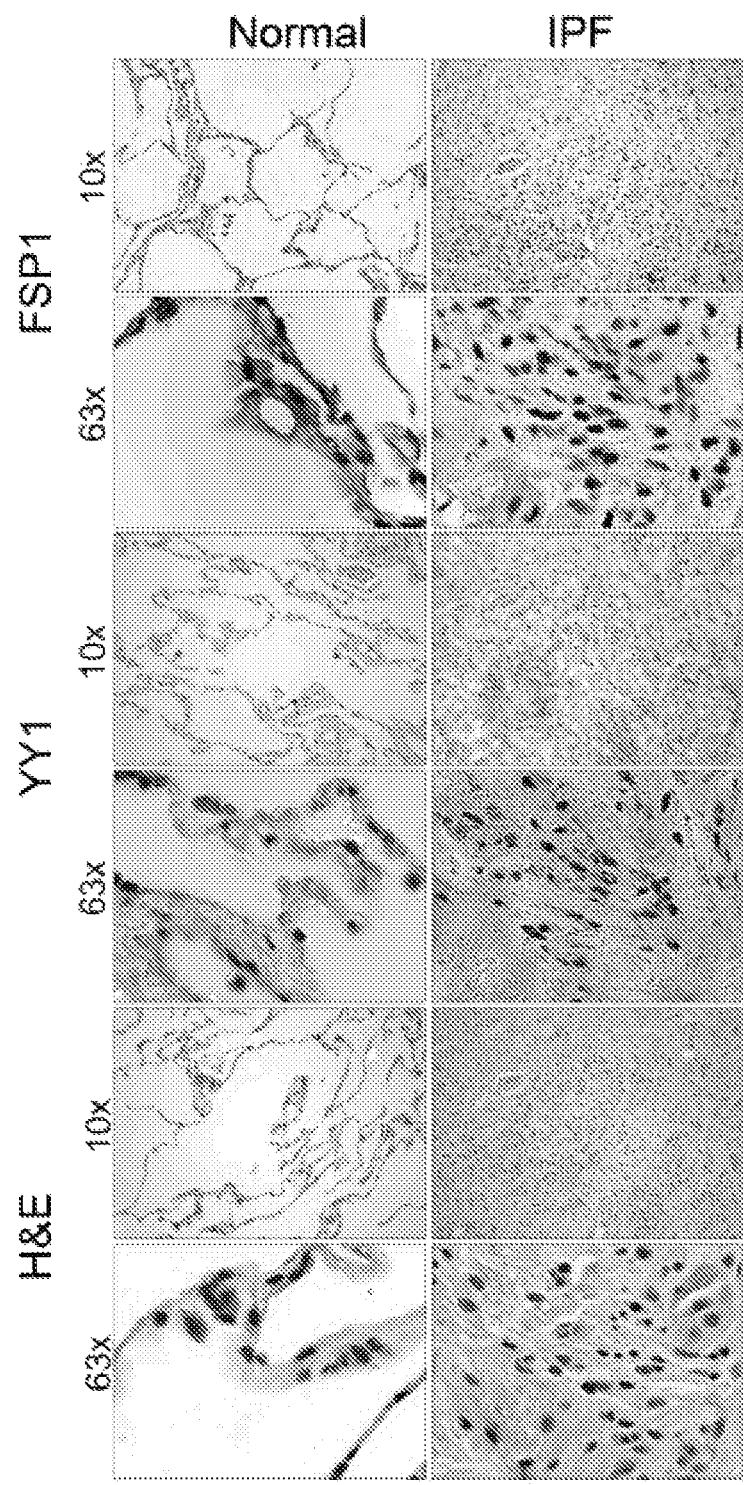
FIG. 4B is a series of light photomicrographs of lung sections from IPF patients ("IPF") and healthy controls ("Normal") (n=3) stained with anti-FSP1, anti-YY1, and hemotoxylin and eosin ("H&E"). YY1 was expression was located in FSP1 positive cells. H&E showed typical lung fibrosis in IPF. Magnification was 10× and 63×, as indicated. All experiments were performed at least three times.

YY1 was found to be over-expressed in lung tissue of human IPF and murine fibrotic models. Determining which cells from lung contribute the YY1 expression can help elucidate a mechanism of lung fibrosis. Injured lung will recruit lung fibroblasts to repair the damaged lung. The recruited lung fibroblasts require YY1 expression for proliferation and differentiation. To investigate whether YY1 is over-expressed in lung fibroblasts, FSP1 and YY1 antibodies were used to determine whether YY1 is up-regulated in lung fibroblasts using IHC staining YY1 was found to be expressed in lung fibroblastal areas in murine silicosis, as shown in FIG. 4A, and in human IPF, as shown in FIG. 4B. This suggests that YY1 expression is located in regions enriched in lung fibroblasts.

Figure 5:
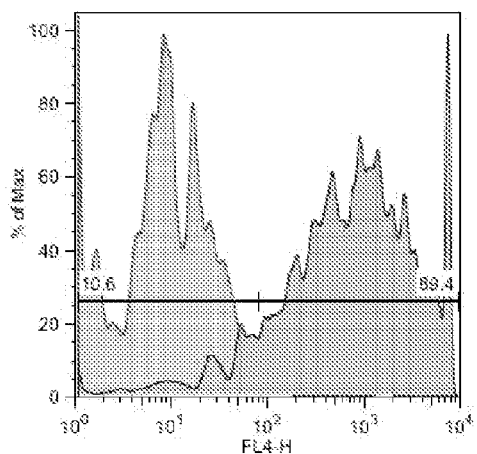
FIG. 5 shows the purity of primary lung fibroblasts isolated from mice treated with bleomycin. After two passages, the fibroblasts were labeled with anti-FSP1 antibody and anti-mouse-APC. Red (light grey) represents isotype labeled-cells and blue (dark grey) represents anti-FSP1 labeled-positive cells (89.4%).
Figure 6A:
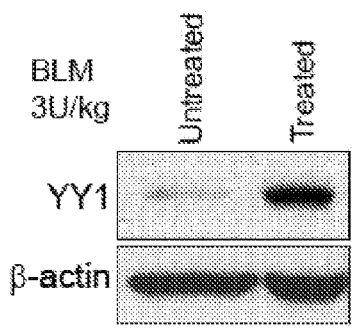
FIG. 6A is an immunoblot of lung fibroblasts isolated from mice treated intratracheally with 3 U/kg of bleomycin ("BLM") and untreated mice (n=4 mice per group). After 12 days, the fibroblasts were isolated and incubated for 6 days (two passages). YY1 expression was determined by immunoblot using anti-YY1 and anti-β-actin antibodies.
Figure 6B:
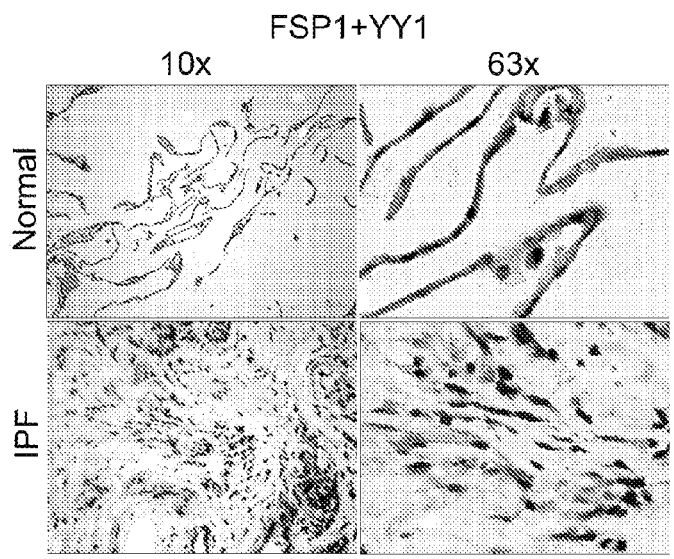
FIG. 6B is a series of light photomicrographs of lung samples from IPF patients ("IPF") and healthy controls ("Normal") double stained with anti-YY1 (brown) and anti-α-SMA (red). Double positive cells are indicated by the arrows. Magnification was as indicated. All experiments were performed at least three times.

In order to further confirm that YY1 is over-expressed in lung fibroblasts, mice were exposed to bleomycin and lung fibroblasts were harvested 12 days later (Lawson et al., "Characterization of Fibroblast-Specific Protein 1 in Pulmonary Fibrosis," *Am. J. Respir. Crit. Care Med.* 171(8):899-907 (2005); Baglole et al., "Isolation and Phenotypic Characterization of Lung Fibroblasts," *Meth. Mol. Med.* 117:115-27 (2005), each of which is hereby incorporated by reference in its entirety). YY1 expression was determined by a western blot in the harvested fibroblasts (see FIG. 5 for the purity of the fibroblasts). As shown in FIG. 6A, YY1 expression was found to be dramatically increased in lung fibroblasts from bleomycin treated mice compared to untreated mice. Double staining IHC was conducted to further confirm that YY1 expression is expressed in lung fibroblasts in human IPF. As shown in FIG. 6B, YY1 was found to be over-expressed in lung fibroblasts. Taken together, not only was YY1 expression found to be located in aggregated lung fibroblasts, but it was also found that YY1 expression is increased in isolated lung fibroblasts. These suggest that increased YY1 expression plays a role in lung fibroblast differentiation and proliferation in injured lung.

Example 17

YY1 is Upregulated by TGF-β and TNF-α in Lung Fibroblasts

Figures 7A, 7B:
FIGS. 7A-7F show that TGF-β induces YY1 protein expression, mRNA levels, and promoter activity in human and mouse lung fibroblasts.
Figures 7C, 7D:
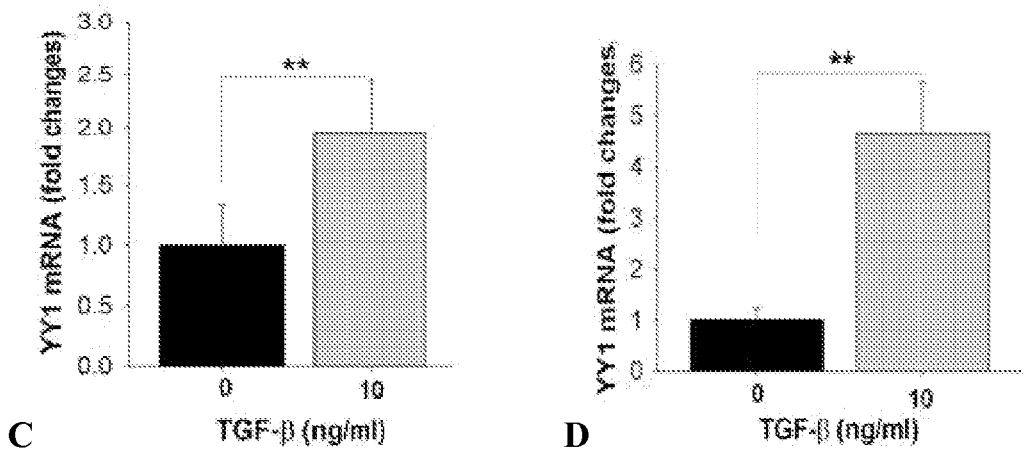
Figures 7E, 7F:
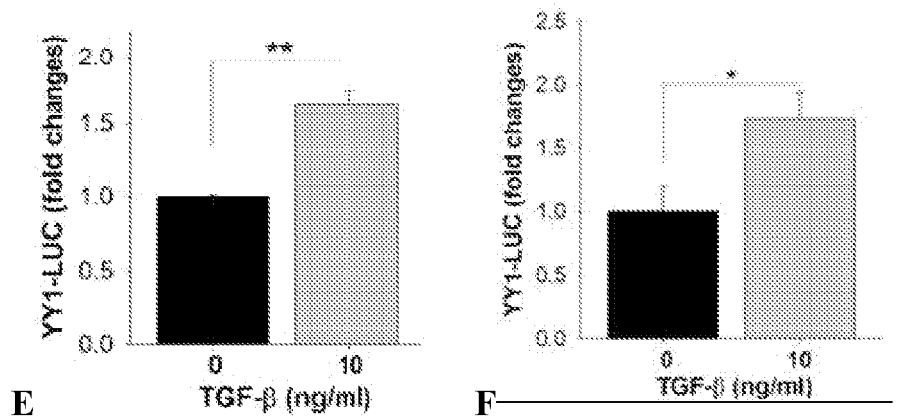
Figure 8A:
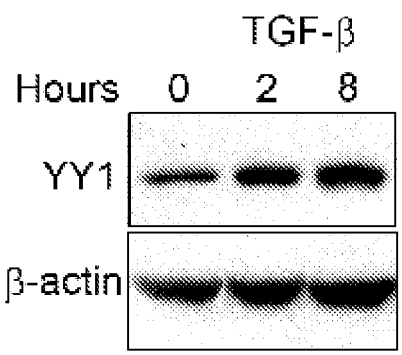
FIGS. 8A-8B show that TGF-β induces YY1 protein expression and promoter activity in adult human lung fibroblasts.
Figure 8B:
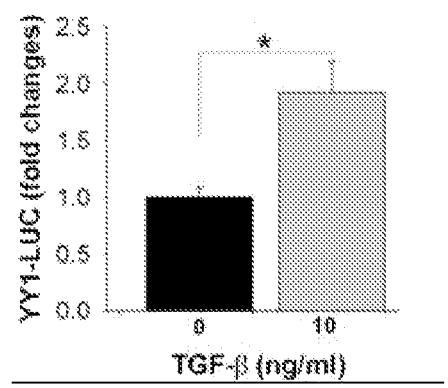

Lung fibrosis results from proliferation and differentiation of fibroblasts in response to the P-fibrotic cytokines TGF-β and TNF-α. To test the possibility that these cytokines directly induce YY1 expression, human WI-38 and mouse MLg2908 lung fibroblast cell lines were grown in vitro and exposed to TGF-β and TNF-α for different times. As shown in FIGS. 7A-7D, YY1 expression was upregulated by TGF-β in both human fetal fibroblasts and murine fibroblasts, as demonstrated by western blot (FIG. 7A (WI-38 cells) and FIG. 7B (MLg2908 cells)) and quantitative PCR (FIG. 7C (WI-38 cells) and FIG. 7D (MLg2908 cells). Using an YY1 promoter-driven luciferase reporter construct, it was discovered that YY1 promoter activity is significantly increased by TGF-β stimulation in lung fibroblasts, as shown in FIG. 7E (YY1-Luc-transfected WI-38 cells) and FIG. 7F (YY1-Luc-transfected MLg2908 cells). A human adult fibroblast cell line (MRC5) was also used, and up-regulation of YY1 expression by TGF-β was confirmed using immunoblot and YY1 reporter activity assays, as shown in FIG. 8A-8B.

Figures 9A, 9B:
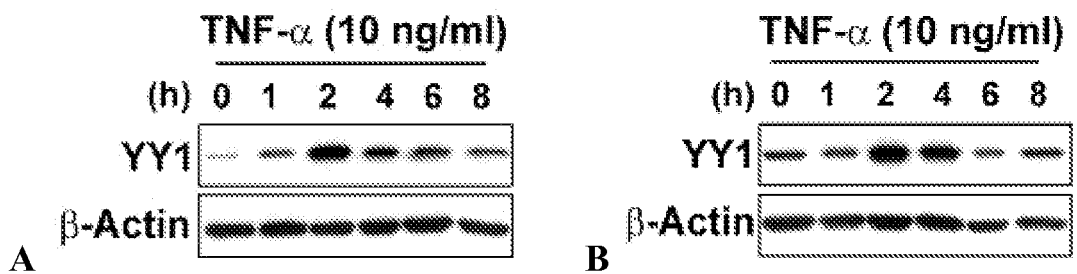
FIGS. 9A-9F show that TNF-α induces YY1 protein expression, mRNA levels, and promoter activity in human and mouse lung fibroblasts.
Figures 9C, 9D:
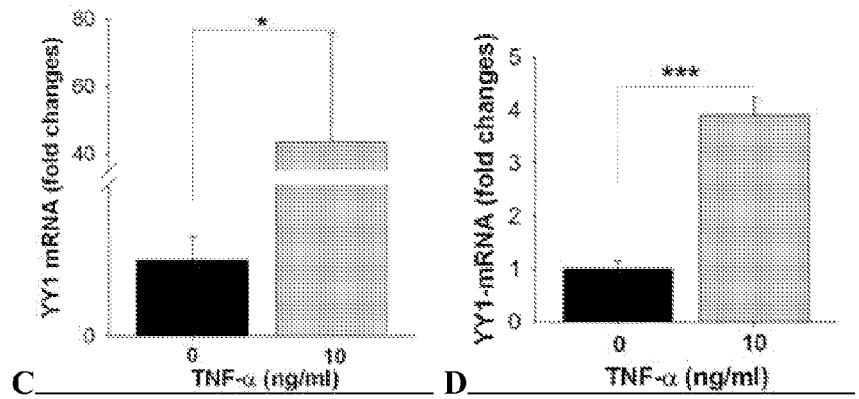
Figures 9E, 9F:
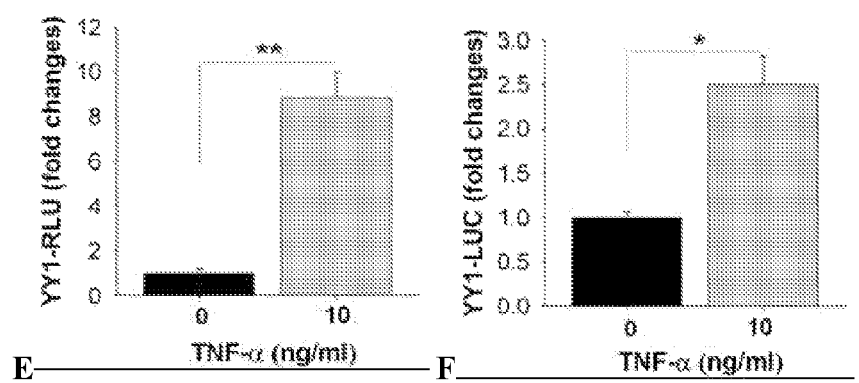

YY1 expression was also found to be increased by TNF-α stimulation, as shown in FIG. 9A (WI-38 cells) and FIG. 9B (MLg2908 cells), although with slightly different kinetics. Quantitative PCR data showed that YY1 transcript levels are upregulated by TNF-α, as shown in FIG. 9C (WI-38 cells) and FIG. 9D (MLg2908 cells). It was also confirmed that YY1 promoter reporter activity is upregulated by TNF-α stimulation in lung fibroblasts, as shown in FIG. 9E (YY1-Luc-transfected MI-38 cells) and FIG. 9F (YY1-Luc-transfected MLg2908 cells). Taken together, these data suggest that YY1 is upregulated by the P-fibrotic cytokines TGF-β and TNF-α in both human and mouse lung fibroblasts.

Example 18

Figures 10A, 10B:
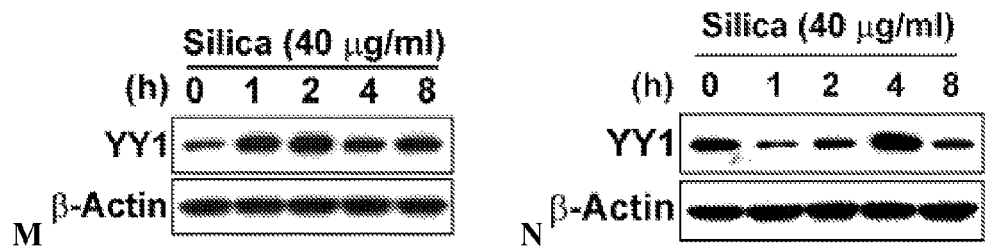
FIGS. 10A-10B are immunoblots that show that YY1 protein expression is increased in WI-38 and MLg2908 cells stimulated with silica. After serum starvation for 24 hours, cells were treated with 40 μg/ml of silica for the indicated time periods in serum-free DMEM. Extracts from WI-38 (FIG. 10A) or MLg2908 (FIG. 10B) cells were immunoblotted with anti-YY1 or anti-β-actin antibodies.
Figure 11:
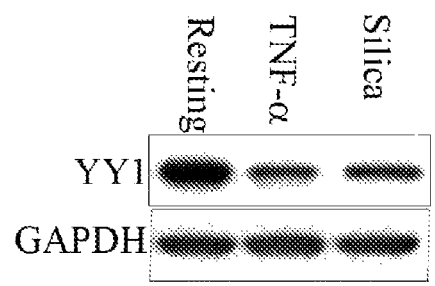
FIG. 11 is a western blot of unstimulated ("resting") IC-21 alveolar macrophages or IC-21 cells stimulated with TNF-α (10 ng/ml) or silica (20 μg/ml). After two days, the cells were harvested and YY1 expression was determined using anti-YY1 and anti-GAPDH antibodies. YY1 expression was slightly decreased by TNF-α and silica.

YY1 is Over-Expressed After Crystalline Silica Stimulation in Lung Fibroblasts In addition to the indirect effects of lung inflammation, crystalline silica can activate cells directly through distinct molecular pathways (Hornung et al., "Silica Crystals and Aluminum Salts Activate the NALP3 Inflammasome Through Phagosomal Destabilization," *Nat. Immunol.* 9(8): 847-56 (2008); Dostert et al., "Innate Immune Activation Through Nalp3 Inflammasome Sensing of Asbestos and Silica," *Science* 320(5876):674-77 (2008), each of which is hereby incorporated by reference in its entirety). Therefore, whether silica particles directly regulate YY1 expression in fibroblasts was tested by incubating cells for up to 8 hours in vitro with a fixed concentration of silica. As shown in FIG. 10A and FIG. 10B, YY1 expression was dramatically increased over an 8-hour time period in both human (FIG. 10A) and mouse (FIG. 10B) lung fibroblasts. This suggests that YY1 expression is directly regulated by silica stimulation in lung fibroblasts. As shown in FIG. 11, neither silica nor TNF-α affected YY1 expression in macrophages, suggesting their enhancing effects on YY1 was relatively specific for fibroblasts.

Example 19

NF-κB-Mediated YY1 Expression in Lung Fibroblasts After TGF-β Stimulation

Figure 12A:
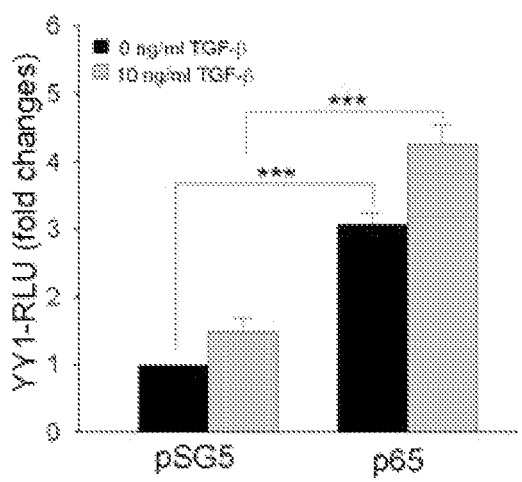
FIGS. 12A-12C demonstrate that TGF-β-induced upregulation of YY-1 expression is mediated by NF-κB.
Figure 12B:
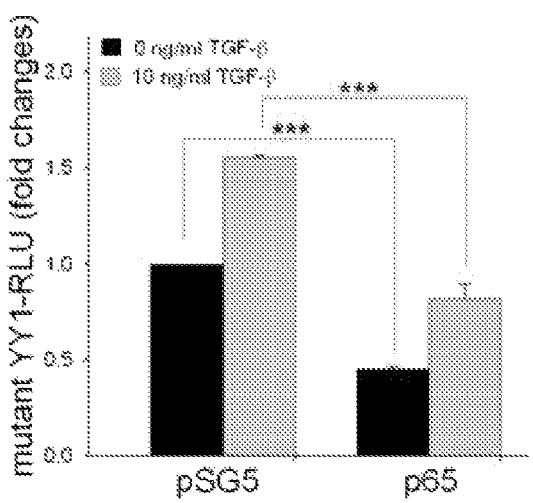

Recent studies have linked the NF-κB pathway to YY1 in other cell types. TNF-α can up-regulate YY1 expression mediated by NF-κB in tumor cells (Huerta-Yepez et al., "Involvement of the TNF-α Autocrine-Paracrine Loop, via NF-κB and YY1, in the Regulation of Tumor Cell Resistance to Fas-Induced Apoptosis," *Clin. Immunol.* 120(3):297-309 (2006), which is hereby incorporated by reference in its entirety). To determine whether TGF-β induces YY1 expression through NF-κB in lung fibroblasts, a YY1 promoter reporter was transiently transfected with or without NF-κB expression vectors into WI-38 cells. Transfected cells were stimulated with TGF-β, and reporter gene activity was analyzed by luminometry. As shown in FIG. 12A, YY1 promoter activity was significantly increased in lung fibroblasts in response to both TGF-β stimulation and co-transfection with NF-κB (p65). As shown in FIG. 12B, disruption of a potential NF-κB site blocked the enhancing effect of NF-κB co-transfection, suggesting that this involves direct binding to the YY1 promoter. This suggests that YY1 gene expression is mediated by NF-κB.

Figure 12C:
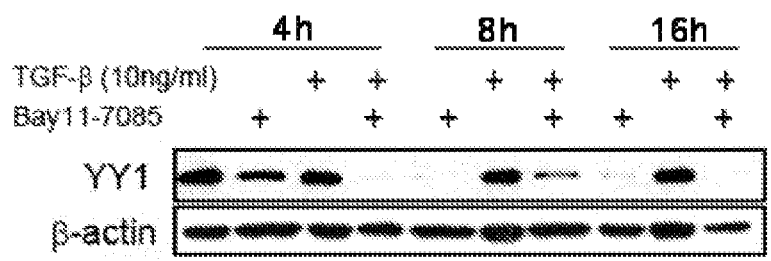

IK-B prevents nuclear translocation of NF-κB. To further investigate the requirement for the NF-κB pathway after TGF-β stimulation, an indirect NF-κB inhibitor (Bay11-7085) was employed to block IK-B degradation and prevent NF-κB translocation into the nucleus. As shown in FIG. 12C, YY1 expression was abolished by Bay11-7085 after TGF-β stimulation. These findings suggest that the pathway leading to YY1 up-regulation is mediated through NF-κB by TGF-β stimulation in lung fibroblasts.

Example 20

Figure 13A:
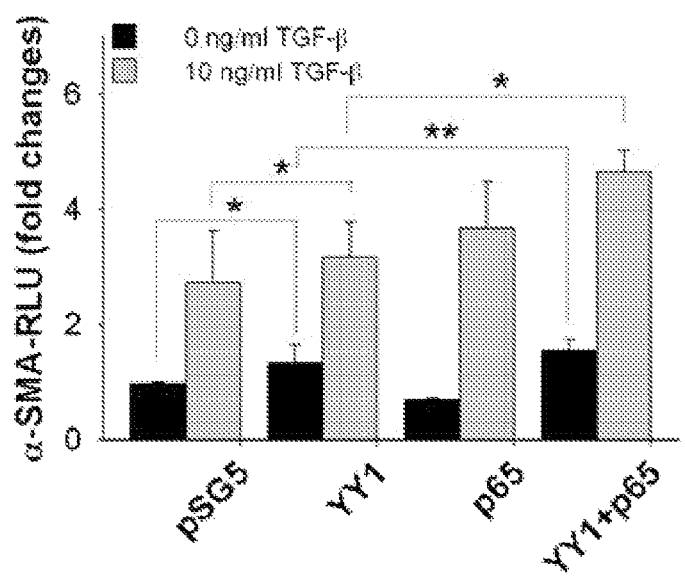
FIGS. 13A-13C show that α-SMA activity is upregulated by YY1.
Figure 13B:
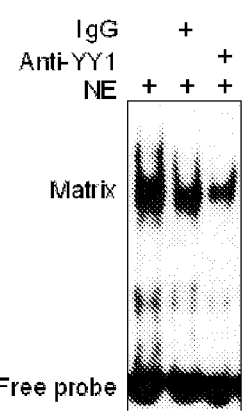
Figure 13C:
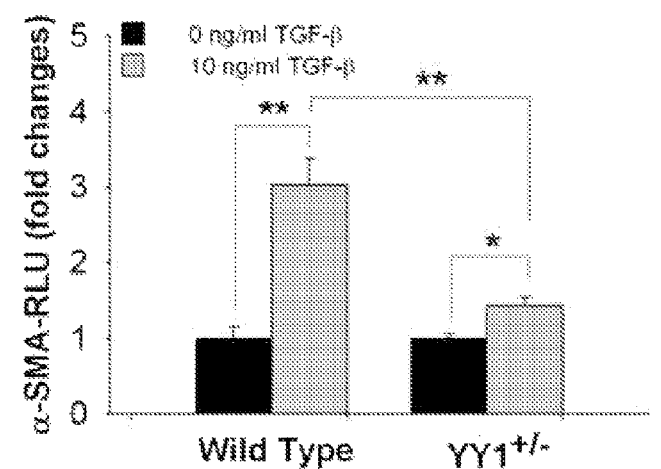

The Myofibroblast Marker α-SMA is Up-Regulated by YY1

α-SMA and collagen are highly expressed in myofibroblasts, the presence of which is a hallmark of fibrotic lung diseases. Collagen has been reported to be up-regulated by YY1 binding to collagen promoters (Riquet et al., "YY1 Is a Positive Regulator of Transcription of the Col1 al Gene," *J. Biol. Chem.* 276(42):38665-72 (2001), which is hereby incorporated by reference in its entirety). Although YY1 can bind to the α-SMA promoter, it is unknown whether it upregulates or downregulates α-SMA promoter activity (Bushel et al., "Two Serum Response Elements Mediate Transcriptional Repression of Human Smooth Muscle α-Actin Promoter in Ras-Transformed Cells," *Oncogene* 10(7):1361-70 (1995), which is hereby incorporated by reference in its entirety). To investigate the ability of YY1 to regulate α-SMA promoter activity, a murine 740-bp construct driving the firefly luciferase gene (α-SMA-Luc) was constructed. This construct was transfected with or without a YY1 expression vector into WI-38 cells. As shown in FIG. 13A, over-expressed YY1 alone significantly increased α-SMA promoter activity, and this effect was further enhanced by TGF-$β_1$ stimulation. Using electromobility gel shift assays, it was confirmed that nuclear YY1 can directly bind to the α-SMA promoter, as shown in FIG. 13B. Therefore, in addition to type I collagen, the α-SMA gene represents another potential YY1 target in lung fibroblasts. The enhancing effects of YY1 on α-SMA-Luc activity were further augmented by co-transfection with NF-κB. This finding suggests that these two factors interact to regulate α-SMA promoter activity, as shown in FIG. 13A. To determine whether YY1 regulates α-SMA promoter activity in primary lung cells, lung fibroblasts were isolated from wild-type and heterozygous YY1$^{+/-}$ mice, which express about half the normal complement of YY1. After transient transfection using electroporation, it was found that α-SMA promoter activity was markedly decreased in fibroblasts from YY1$^{+/-}$ mice compared to wild-type littermates, as shown in FIG. 13C. Taken together, these data provide strong support for the idea that α-SMA is a previously unrecognized and important target of YY1 in primary lung fibroblasts in vivo.

Example 21

Induction of α-SMA and Collagen Expression in Lung Tissues and Fibroblasts Isolated from Transgenic Mice (YY1$^{cc10}$)

Figure 14A:
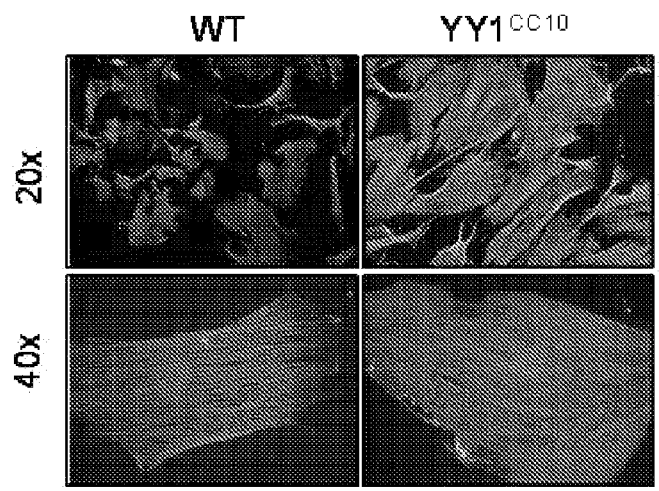
FIGS. 14A-14C show that YY1 expression is greater in YY1$^{CC10}$ mice than in normal littermate mice.
Figure 14B:
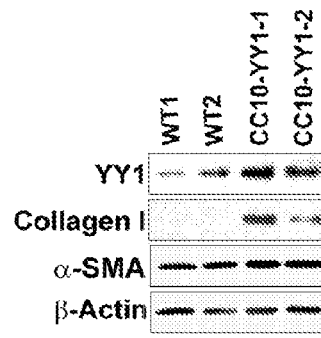
Figure 14C:
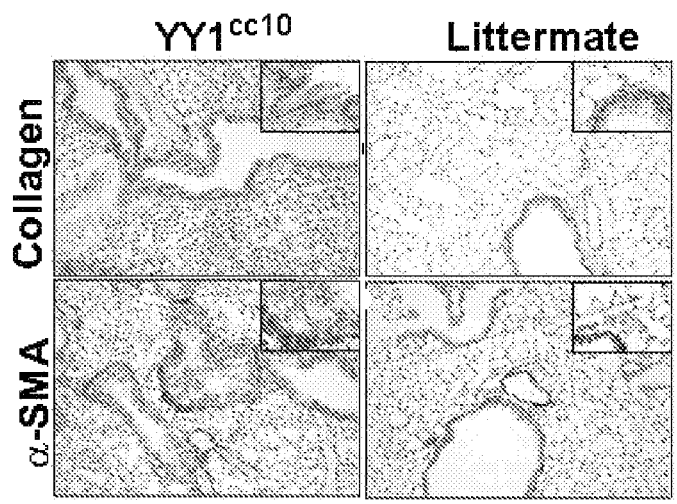

To assess the role of YY1 in α-SMA regulation in vivo, a transgenic mouse was constructed in which the rat clara cell 10 (cc10) promoter drives expression of full-length YY1 cDNA (YY1$^{cc10}$ mice). Although primarily restricted to the airway epithelium, cc10 is also expressed at lower levels in lung fibroblasts (Lesur et al., "Clara Cell Protein (CC-16) Induces a Phospholipase A2-Mediated Inhibition of Fibroblast Migration in Vitro," Am. J. Respir. Crit. Care Med. 152(1):290-97 (1995), which is hereby incorporated by reference in its entirety). When lung fibroblasts were isolated from YY1$^{cc10}$ mice or wild type controls, α-SMA expression was strikingly increased and associated with a larger cell size, as evidenced by immunofluorescent staining, as shown in FIG. 14A. As shown in FIG. 14B, YY1, collagen, and α-SMA protein were increased in the fibroblasts of YY1$^{cc10}$ mice by immunoblotting. Via immunohistochemistry, increased expression of YY1, collagen 1, and α-SMA was observed in the lungs of YY1$^{cc10}$ mice, especially around the airways, as shown in FIG. 14C. Therefore, over-expressed YY1 increases α-SMA expression in fibroblasts both in vitro (see FIG. 15A) and in vivo (see FIG. 14B and FIG. 14C).

Example 22

α-SMA and Collagen Are Downregulated by Inhibition of YY1 Expression Using YY1 shRNA and Conditional Knockout YY1 (YY1$^{f/f}$)

Figure 15A:
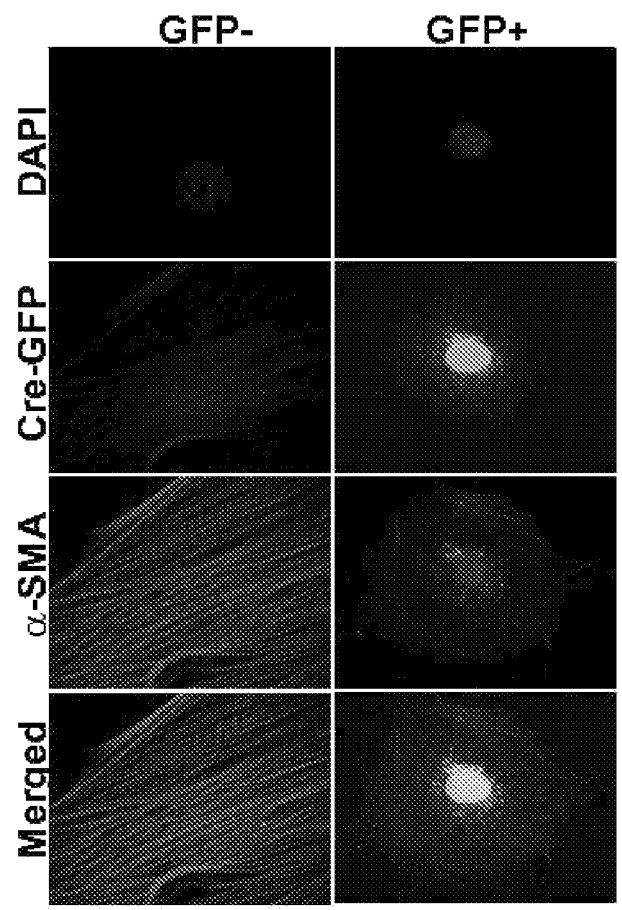
FIGS. 15A-15D, show that expression of α-SMA and collagen 1 is diminished, and this decrease is accompanied by diminished YY1 expression.
Figure 15B:

To complement the gain-of-function studies in YY1$^{cc10}$ mice, two different YY1-knockdown approaches were used to evaluate whether α-SMA and collagen were reduced using loss-of-function strategies. First, lung fibroblasts were isolated from YY1 "foxed" mice (YY1$^{f/f}$), in which the exon 1 is flanked by lox-p sites to allow for Cre-mediated deletion (Liu et al., "Yin Yang 1 Is a Critical Regulator of B-Cell Development," Genes Dev. 21(10):1179-89 (2007), which is hereby incorporated by reference in its entirety). The lung fibroblasts were then infected with lentivirus Cre in vitro. After recovery for five days, immunoblotting was carried out using anti-YY1, demonstrating a lack of YY1 expression in fibroblasts obtained from YY1$^{f/f}$ mice, as shown in FIG. 15B. Using a Cre-GFP fusion protein, it was found that both YY1 and α-SMA expression were markedly reduced in transfected fibroblasts from YY1$^{f/f}$ mice, as shown in FIG. 15A. These data indicate that YY1 is an important regulator of α-SMA expression in lung fibroblasts in vitro.

Figure 15C:
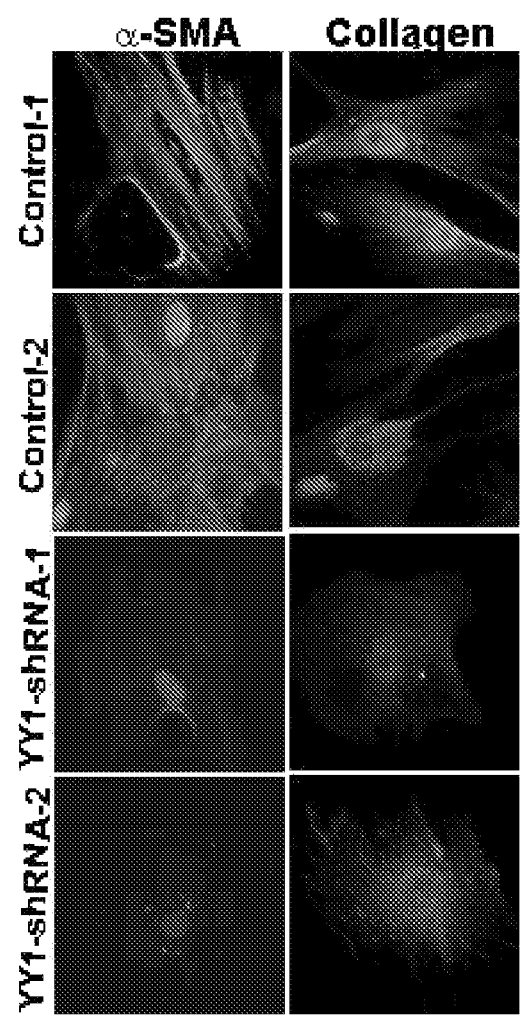
Figure 15D:
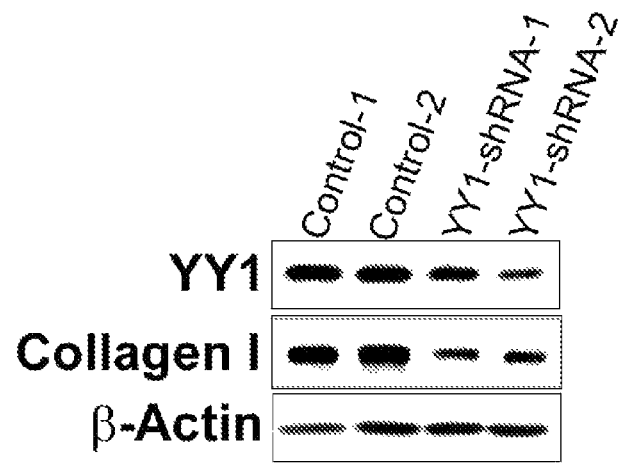

Whether reducing the expression of YY1 would affect gene expression in human lung fibroblasts was then tested. A fibroblast cell line (LL97A) was derived from a human subject with IPF and infected using different YY1 lentiviral shRNA constructs. After transduction with two controls and two YY1 lentiviral shRNA constructs, LL97A cells were allowed to recover for three days and then selected in puromycin to enrich for transduced cells. FIGS. 15C and 15D show that decreased YY1 expression inhibited both α-SMA and collagen expression in human lung fibroblasts, as determined by immunofluorescence staining and immunoblot assays. These data strongly suggest that knockdown of YY1 expression in lung fibroblasts inhibits fibroblast activation. Furthermore, these data suggest that YY1 may be a potential therapeutic target for fibrotic lung disease in vitro.

Example 23

Figure 16A:
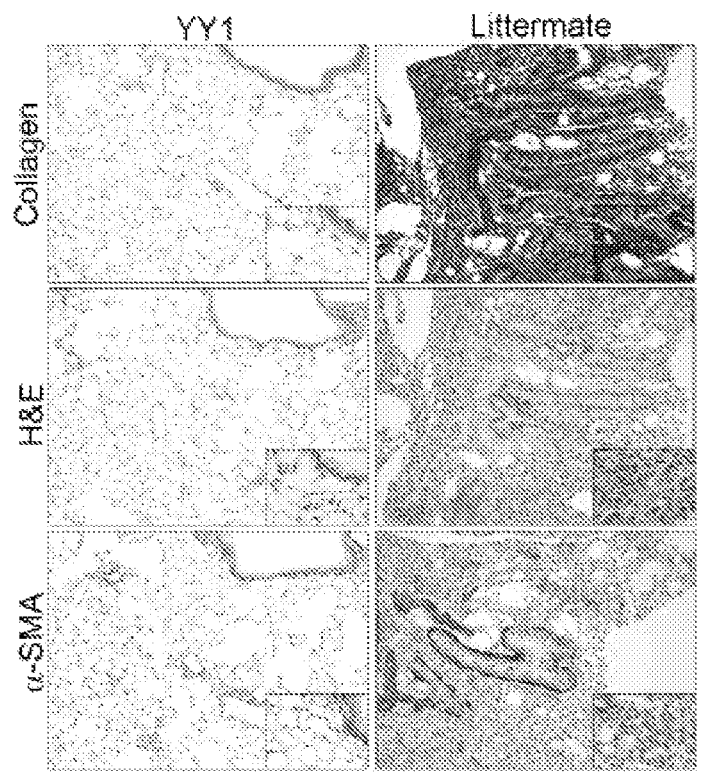
FIGS. 16A-16D show that the expression of α-SMA and collagen is decreased in YY1$^{+/-}$ and YY1$^{f/f}$ compared to littermate mice.
Figure 16B:
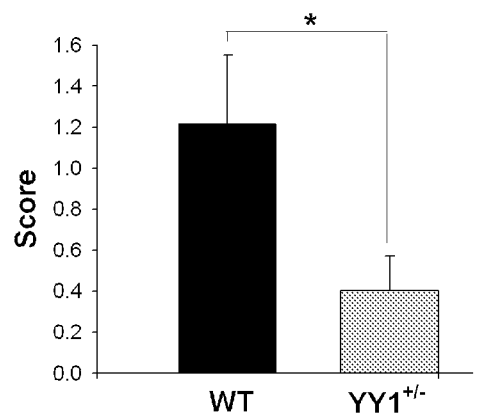

Partial YY1 Deficiency Protects Mice from Lung Fibrosis After Exposure to Both Silica and Bleomycin To test the hypothesis that decreased YY1 expression provides protection against lung fibrosis, two partially deficient mice were utilized in two different fibrotic lung models. First, heterozygous YY1 (YY1$^{+/-}$) mice (or littermate controls on the C57BL/6 background) were instilled with silica particles by intratracheal injection. Three weeks later, the mice were sacrificed and the lungs stained by immunohistochemistry. Connective tissue was also analyzed using Masson's trichrome straining. As shown in FIG. 16A, lung fibrosis was markedly decreased in YY1$^{+/-}$ compared to WT mice (indicated by the arrow). There was elevated α-SMA, collagen, and inflammatory cell numbers in wild type compared to YY1$^{+/-}$ mice. α-SMA staining of scar regions present in whole lung was scored by a double blind method. As shown in FIG. 16B, lung scarring was significantly diminished in YY1$^{+/-}$ than in WT groups. This suggests that lung fibrosis was significantly inhibited in YY1$^{+/-}$ mice, and that decreased YY1 expression protects against lung fibrosis.

Figure 16C:
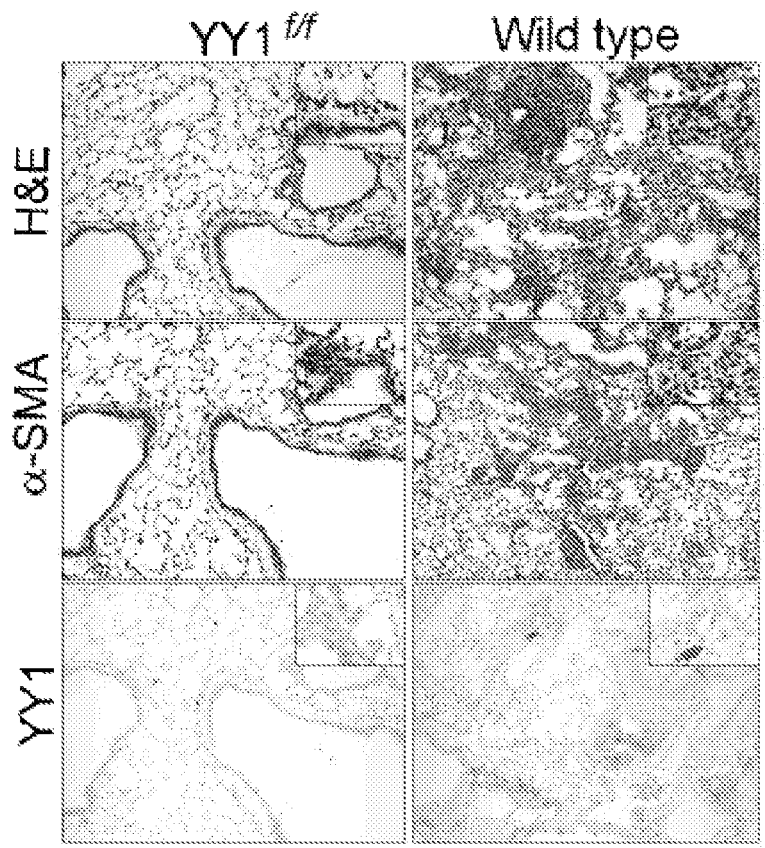
Figure 16D:
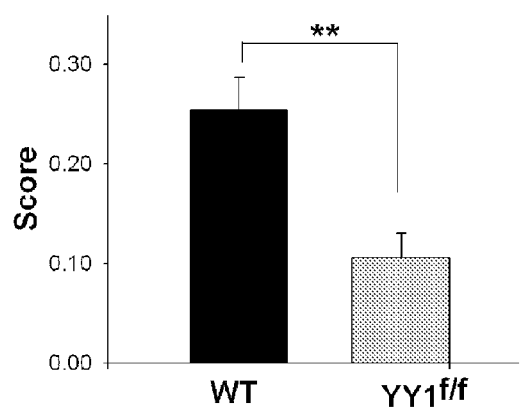

To further demonstrate that partially deficient YY1 mice are protected against lung fibrosis, bleomycin was employed in another YY1-deficient mouse model, i.e., "foxed" YY1$^{f/f}$ mice, which are hypomorphic and express about 75% the normal amount of YY1 protein due to insertion of flox-p sites flanking exon 1 of YY1 (Liu et al., "Yin Yang 1 Is a Critical Regulator of B-Cell Development," Genes Dev. 21(10):1179-89 (2007), which is hereby incorporated by reference in its entirety). Bleomycin was administered by intratracheal instillation into wild-type of YY1$^{f/f}$ littermates, and three weeks post-instillation of bleomycin, the lungs of these mice were harvested and stained by IHC. As shown in FIG. 16C, it was found that lung fibrosis, YY1 expression, and α-SMA expression were increased in the lungs of wild type mice compared to those of YY1$^{f/f}$ mice. Similar to Example 24, scar regions were scored by double blinded method depending on α-SMA expression in fibrotic lung. As shown in FIG. 16D, the scores show that scarring was significantly diminished in YY1$^{f/f}$ compared to WT mice. Taken together, findings obtained from the two YY1-deficient mouse lines indicate that YY1 is a regulator of lung fibrosis and myofibroblast differentiation.

Example 24

Treatment Instilled by Adeno-Cre in YY1$^{f/f}$ Mice

Figure 17A:
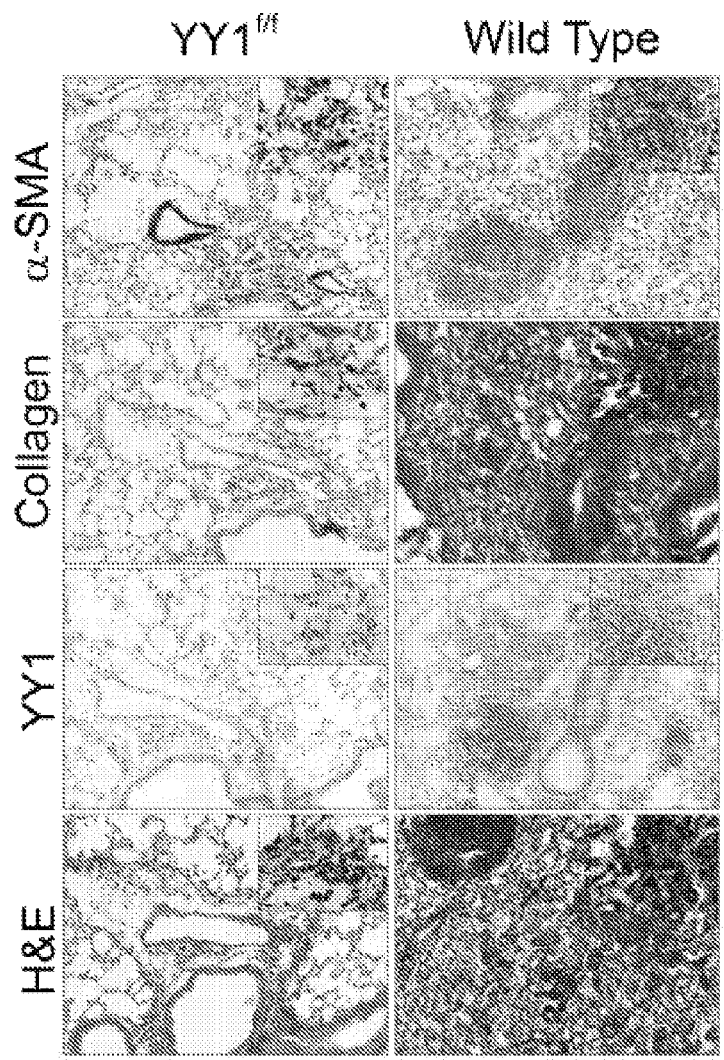
FIGS. 17A-17D show that α-SMA and collagen expression is decreased in YY1$^{f/f}$ compared to wildtype mice. C57BL/6 mice (n=5) and YY1$^{f/f}$ (n=5) mice were instilled by silica (200 µg/mouse). 11 days after silica installation, the mice were treated with adenoviral Cre (4×10$^8$ pfu) for 21 days. Following treatment, lung sections were harvested for analysis.
Figure 17B:
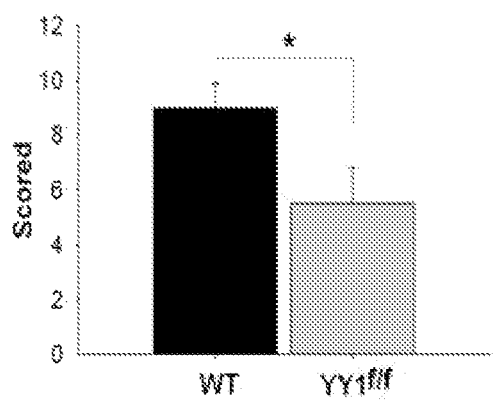
Figure 17C:
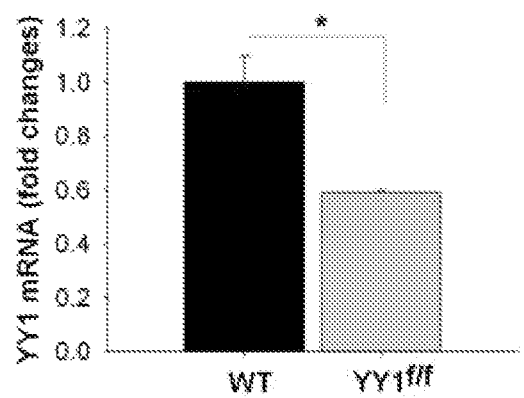
Figure 17D:
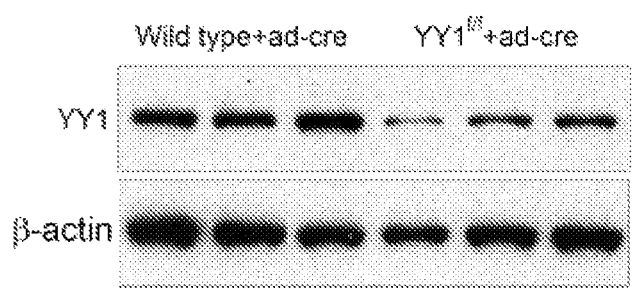

Finally, to further demonstrate that inducible deletion of YY1 could treat mice with fibrosis, adenoviral Cre was instilled into wild-type and YY1$^{f/f}$ mice after silica particles had been instilled into the mice for 5 days. Lungs were harvested 21 days later. FIGS. 17A-17D show that lung fibrosis and YY1 expression were markedly attenuated in YY1$^{f/f}$ (but not wild type mice) exposed to silica and treated with adenoviral Cre. As shown in FIG. 17A, α-SMA and collagen were decreased in YY1$^{f/f}$ mice compared with wild type mice. As shown in FIG. 17B, α-SMA staining of scar regions present in whole lung was scored by a double blind method. YY1 expression was confirmed by immunoblot and quantitative PCR, as shown in FIGS. 17C and 17D.

Discussion of Examples 1-24

YY1 is a versatile transcription factor that can activate, repress or initiate gene expression. Several studies had demonstrated the ability of YY1 to regulate cell growth, differentiation and apoptosis, but relatively little was known about the role of YY1 in irreversible chronic inflammation or tissue injury and repair responses in vivo. Examples 1-25 demonstrate that YY1 mRNA and protein are upregulated in two different mouse models of lung fibrosis, as well as in lungs from human subjects with IPF (see FIGS. 1A-1C, 2A-2C, and 3A-3C), a progressive and incurable disease. Although several lung cells types can express YY1, lung fibroblasts were focused on, because lung fibroblasts ultimately control deposition of extracellular matrix and differentiation to myofibroblasts characterizes the injury/repair response. Importantly, YY1 expression was found to be highly increased in lung fibroblasts of human IPF and murine fibrotic models. This implies that the enhancement of lung fibroblasts requires YY1 expression in injury/repair process. Since YY1 can directly bind to the promoter regions of both the collagen (Riquet et al., "YY1 Is a Positive Regulator of Transcription of the Col1a1 Gene," *J. Biol. Chem.* 276(42):38665-72 (2001), which is hereby incorporated by reference in its entirety) and α-smooth muscle actin (α-SMA) genes, and is required for their expression (see FIG. 13A), it was concluded that YY1 directly regulates two crucial genes involved in fibroblast activation and myofibroblast differentiation. This suggested that YY1 might regulate lung fibrosis in vivo, which was confirmed using both gain-of-function and loss-of-function approaches in two distinct mouse models. Thus, the present studies elucidate that by regulating gene expression in fibroblasts, YY1 plays a novel role in tissue repair and fibroblast differentiation.

Lung myofibroblasts derive from multiple sources including resident progenitor cells, circulating fibrocytes (Andersson-Sjoland et al., "Fibrocytes Are a Potential Source of Lung Fibroblasts in Idiopathic Pulmonary Fibrosis," *Int. J. Biochem. Cell Biol.* 40(10):2129-40 (2008), which is hereby incorporated by reference in its entirety) or by epithelial to mesenchymal transition (EMT) (Kuroishi et al., "Epithelial-Mesenchymal Transition Induced by Transforming Growth Factor-β1 in Mouse Tracheal Epithelial Cells," *Respirology* 14(6):828-37 (2009); Radisky et al., "Fibrosis and Cancer: Do Myofibroblasts Come Also from Epithelial Cells via EMT?," *J. Cell. Biochem.* 101(4):830-39 (2007), each of which is hereby incorporated by reference in its entirety). Regardless of their derivation, the differentiation of fibroblasts into myofibroblasts is recognized as a key process in fibrotic responses. Myofibroblasts, which are characterized by expression of the α-SMA gene, are more resistant to apoptosis (Horowitz et al., "Combinatorial Activation of FAK and AKT by Transforming Growth Factor-β1 Confers an Anoikis-Resistant Phenotype to Myofibroblasts," *Cell Sign.* 19(4):761-71 (2007); Garneau-Tsodikova & Thannickal, "Protein Kinase Inhibitors in the Treatment of Pulmonary Fibrosis," *Curr. Med. Chem.* 15(25):2632-40 (2008), each of which is hereby incorporated by reference in its entirety), and synthesize and secrete collagens, α-SMA, and other extracellular matrix molecules that lead to tissue remodeling. The present Examples show that YY1 expression is not only increased in accumulated fibroblasts but also in individual fibroblasts by silica or bleomycin instillation (see FIGS. 4A-4B, FIG. 5, and FIGS. 6A-6B). This sufficiently demonstrates that YY1 expression plays a very important role in the recruitment of lung fibroblasts of fibrotic lung. It was also demonstrated that YY1 directly binds to the proximal α-SMA promoter (in keeping with Ellis et al., "Increased Actin Polymerization Reduces the Inhibition of Serum Response Factor Activity by Yin Yang 1," *Biochem. J.* 364(Pt 2):547-54 (2002), which is hereby incorporated by reference in its entirety), and that over-expressed YY1 enhances α-SMA gene expression. In contrast, using both shRNA and Cre-mediated knockdown of YY1 expression in primary lung fibroblasts (see FIGS. 15A and 15C), loss of YY1 was found to markedly reduce α-SMA expression. Taken together, these data suggest that YY1 plays a novel role in myofibroblast differentiation at least in part by regulating α-SMA gene expression. In addition to regulating myofibroblast gene expression, YY1 may also confer resistance to apoptosis (Bonavida, "Rituximab-Induced Inhibition of Antiapoptotic Cell Survival Pathways: Implications in Chemo/Immunoresistance, Rituximab, Unresponsiveness, Prognostic and Novel Therapeutic Interventions," *Oncogene* 26(25):3629-36 (2007), which is hereby incorporated by reference in its entirety), which is known to be induced during lung fibrotic responses after exposure to silica (Han et al., "*Angelica sinensis* Down-Regulates Hydroxyproline and Tgfb1 and Provides Protection in Mice with Radiation-Induced Pulmonary Fibrosis," *Radiat. Res.* 165(5):546-52 (2006); Gambelunghe et al., "[Crystalline Silica Can Induce Oxidative Stress by Inhibiting Glyoxalase System in Bronchial Epithelial Cells]," *G. Ital. Med. Lav. Ergon.* 29(3Suppl):397-99 (2007), each of which is hereby incorporated by reference in its entirety), TGF-β (Honda et al., "Immunogenetic Analysis of Silicosis in Japan," *Am. J. Respir. Cell Mol. Biol.* 8(1):106-11 (1993), which is hereby incorporated by reference in its entirety), and TNF-α (Huerta-Yepez et al., "Involvement of the TNF-α Autocrine-Paracrine Loop, via NF-κB and YY1, in the Regulation of Tumor Cell Resistance to Fas-Induced Apoptosis," *Clin. Immunol.* 120 (3):297-309 (2006); Zhao et al., "Time-Dependent Apoptosis of Alveolar Macrophages from Rats Exposed to Bleomycin: Involvement of TNF Receptor 2," *J. Toxicol. Environ. Health A* 67(17):1391-06 (2004)), each of which is hereby incorporated by reference in its entirety). Thus decreasing YY1 expression may attenuate fibrotic responses by decreasing myofibroblast resistance to apoptosis, in keeping with a growing role for YY1 in cell survival in response to injury (Cunningham et al., "mTOR Controls Mitochondrial Oxidative Function Through a YY1-PGC-1α Transcriptional Complex," *Nature* 450(7170):736-406 (2007); Grubach et al., "Gene Expression Profiling of Polycomb, Hox and Meis Genes in Patients with Acute Myeloid Leukaemia," *Eur. J. Haematol.* 81(2):112-22 (2008), each of which is hereby incorporated by reference in its entirety).

Figure 18:
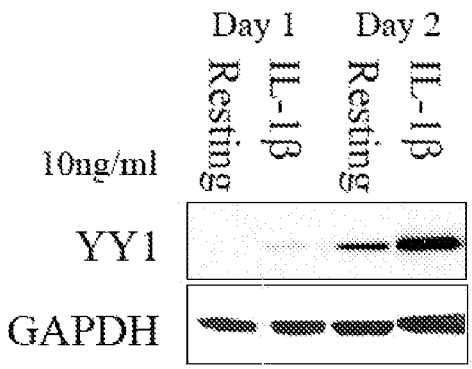
FIG. 18 is an immunoblot showing YY1 in WI-38 cells that were unstimulated ("Resting") or treated with IL-1β (10 mg/ml). Immunoblots were performed on Day 1 and Day 2 using anti-YY1 and anti-GAPDH antibodies. YY1 expression was shown to be upregulated by IL-1β.

Direct exposure to profibrotic silica particles, or indirect exposure to the profibrotic cytokines TNF-α and TGF-β, were found to induce YY1 expression in fibroblasts (see FIGS. 7A-7F, 8A-B, and 9A-9F, and 10A-10B). Although YY1 is upregulated by TGF-β in LPS-induced macrophage (Joo et al., "Yin Yang 1 Enhances Cycloxygenase-2 Gene Expression in Macrophages," *Am. J. Physiol. Lung Cell. Mol. Physiol.* 292(5):L1219-26 (2007), which is hereby incorporated by reference in its entirety), LPS induced the inflammation is different from the inflammation in silica-induced. In contrast YY1 expression was not found to be affected in alveolar macrophages by TNF-α or silica (see FIG. 11). Silica and asbestos particles have been shown to activate the Nalp3 containing inflammasome and induce caspase-1 driven processing of mature IL-1β, (Hornung et al., "Silica Crystals and Aluminum Salts Activate the NALP3 Inflammasome Through Phagosomal Destabilization," *Nat. Immunol.* 9(8): 847-56 (2008); Dostert et al., "Innate Immune Activation Through Nalp3 Inflammasome Sensing of Asbestos and Silica," *Science* 320(5876):674-77 (2008); Cassel et al., "The Nalp3 Inflammasome Is Essential for the Development of Silicosis," *Proc. Nat'l Acad. Sci. U.S.A.* 105(26):9035-40 (2008), each of which is hereby incorporated by reference in its entirety), which the present Examples also show upregulates fibroblast YY1 expression in vitro (see FIG. 18). Cytokine-dependent induction of YY1 required the transcription factor NF-κB (see FIGS. 12A-12C and 13A-13C), in keeping with prior studies in other cell types (Huerta-Yepez et al., "Involvement of the TNF-α Autocrine-Paracrine Loop, via NF-κB and YY1, in the Regulation of Tumor Cell Resistance to Fas-Induced Apoptosis," *Clin. Immunol.* 120(3):297-309 (2006); Baritaki et al., "Inhibition of Yin Yang 1-Dependent Repressor Activity of DR5 Transcription and Expression by the Novel Proteasome Inhibitor NPI-0052 Contributes to Its TRAIL-Enhanced Apoptosis in Cancer Cells," *J. Immunol.* 180(9):6199-210 (2008), each of which is hereby incorporated by reference in its entirety). Thus in addition to promoting expression of cytokines, chemokines, and other mediators that promote inflammation, the present Examples suggest that by inducing YY1 expression, NF-κB promotes the expression of genes involved in tissue repair responses. Increased YY1 expression mediated by NF-κB can downregulate Fas and death receptor 5 (DR5) (Huerta-Yepez et al., "Involvement of the TNF-α Autocrine-Paracrine Loop, via NF-κB and YY1, in the Regulation of Tumor Cell Resistance to Fas-Induced Apoptosis," *Clin. Immunol.* 120(3):297-309 (2006); Huerta-Yepez et al., "Nitric Oxide Sensitizes Tumor Cells to TRAIL-Induced Apoptosis via Inhibition of the DR5 Transcription Repressor Yin Yang 1," *Nitric Oxide* 20(1):39-52 (2009), each of which is hereby incorporated by reference in its entirety) expression and consequently protect lung myofibroblasts from apoptosis. Smads are also activated by TGF-β during lung fibrosis, and although Smad3 can bind to different domains of YY1 (Kurisaki et al., "Nuclear Factor YY1 Inhibits Transforming Growth Factor β- and Bone Morphogenetic Protein-Induced Cell Differentiation," *Mol. Cell Biol.* 23(13):4494-510 (2003), which is hereby incorporated by reference in its entirety), the present Examples found that over-expressed Smad3 did not regulate YY1 promoter activity in lung fibroblasts. Since TGF-β and TNF-α are universally implicated in injury/repair and remodeling, it is predicted that YY1 will play a role in fibroblast differentiation and activation in diverse tissues, and that the paradigms established in the present Examples should be broadly generalizable.

Figure 19:
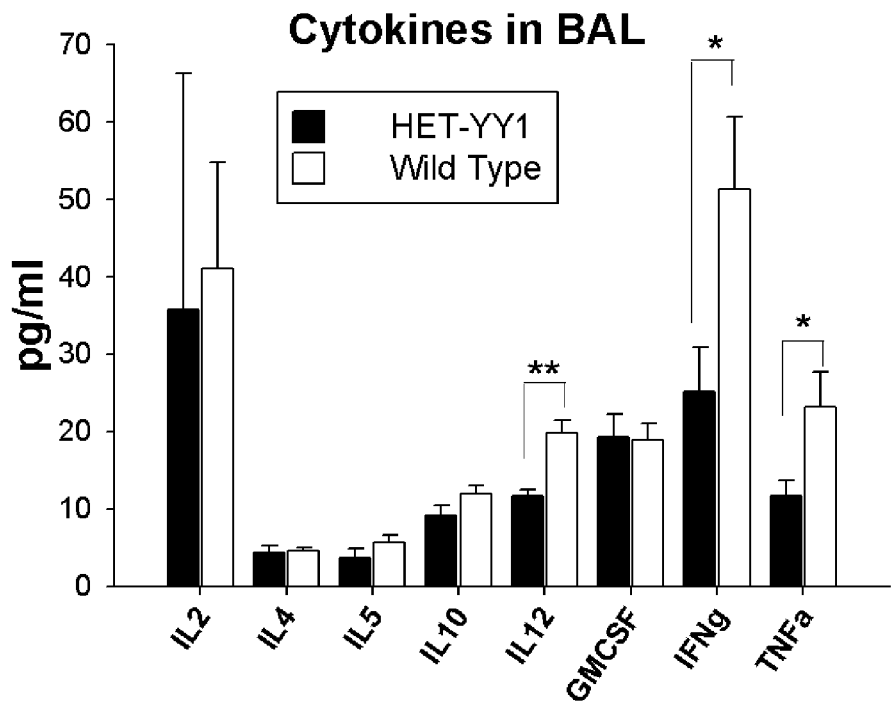
FIG. 19 is a graph of the cytokines present in the bronchoalveolar lavage ("BAL") of wild type and YY1$^{+/-}$ ("HET-YY1") mice. *p<0.05; **p<0.01.

Two distinct models of lung fibrosis were used and it was found that even partial YY1 deficiency protected mice from the effects of both silica particles and bleomycin. Using both models, lung fibrosis was found to be reduced in YY1 deficient mice using both quantitative and qualitative readouts of fibroblast activation and differentiation, in keeping with studies of lung fibroblasts in vitro. Since exposure to silica and bleomycin are thought to induce lung fibrosis by different mechanisms (i.e., mitochondria and lysosome damage caused by silica versus DNA damage caused by bleomycin), this important result suggests that YY1 activation is a final common mechanism leading to fibrosis during repair responses. YY1 also plays a role in DNA repair by homologous recombination (Wu et al., "A YY1-IN080 Complex Regulates Genomic Stability Through Homologous Recombination-Based Repair," *Nat. Struct. Mol. Biol.* 14(12):1165-72 (2007), which is hereby incorporated by reference in its entirety). Therefore, YY1 expression may repair damaged DNA in lung fibrosis. Although Rag knockout mice still develop lung fibrosis in response to fluorescein isothiocyanate (Christensen et al., "Induction of Lung Fibrosis in the Mouse by Intratracheal Instillation of Fluorescein Isothiocyanate Is not T-Cell-Dependent," *Am. J. Pathol.* 155(5):1773-79 (1999), which is hereby incorporated by reference in its entirety), adaptive immune response still can accelerate the formation of lung fibrosis. YY1 can enhance cyclooxygenase-2 expression in alveolar macrophages, which plays a role in inflammation of lung fibrosis (Joo et al., "Yin Yang 1 Enhances Cycloxygenase-2 Gene Expression in Macrophages," *Am. J. Physiol. Lung Cell. Mol. Physiol.* 292(5): L1219-26 (2007), which is hereby incorporated by reference in its entirety), and can increase cytokine expression (Guo et al., "Yin Yang-1 Activates Interleukin-4 Gene Expression in T Cells," *J. Biol. Chem.* 276(52):48871-78 (2001); Guo et al., Yin Yang 1 Regulates Effector Cytokine Gene Expression and $T_H2$ Immune Responses," *J. Allergy Clin. Immunol.* 122(1): 195-201.e5 (2008), each of which is hereby incorporated by reference in its entirety) in T cells. Thus decreasing YY1 expression may inhibit inflammation during injury/repair responses, and may help to protect against lung fibrosis by this mechanism. In support of this idea, lower levels of inflammatory cytokines were detected in bronchoalveolar lavage fluids from silica challenged $YY1^{+/-}$ compared to wild type controls (see FIG. 19). The $YY1^{+/-}$ heterozygous mice used in this study express about 50% of normal YY1 levels (Affar el et al., "Essential Dosage-Dependent Functions of the Transcription Factor Yin Yang 1 in Late Embryonic Development and Cell Cycle Progression," *Mol. Cell Biol.* 26(9): 3565-81 (2006); Donohoe et al., "Targeted Disruption of Mouse Yin Yang 1 Transcription Factor Results in Peri-Implantation Lethality," *Mol. Cell Biol.* 19(10):7237-44 (1999), each of which is hereby incorporated by reference in its entirety), whereas the $YY1^{f/f}$ alleles are hypomorphic leading to expression of about 75% of normal levels of YY1 (Liu et al., "Yin Yang 1 Is a Critical Regulator of B-Cell Development," *Genes Dev.* 21(10):1179-89 (2007); Affar el et al., "Essential Dosage-Dependent Functions of the Transcription Factor Yin Yang 1 in Late Embryonic Development and Cell Cycle Progression," *Mol. Cell Biol.* 26(9):3565-81 (2006), each of which is hereby incorporated by reference in its entirety). In an additional approach, it was also found that decreasing YY1 expression by adenoviral Cre in $YY1^{f/f}$ mice can protect from lung fibrosis. This approach by exogenously given adenoviral Cre suggests that similar strategies may be useful therapeutically. Thus these data indicate that during tissue inflammation and repair responses in vivo, YY1 regulates gene expression in a gene-dosage dependent manner, consistent with prior studies in a model of allergic lung inflammation (Guo et al., Yin Yang 1 Regulates Effector Cytokine Gene Expression and $T_H2$ Immune Responses," *J. Allergy Clin. Immunol.* 122(1):195-201.e5 (2008), which is hereby incorporated by reference in its entirety).

YY1 is generally considered a constitutively expressed nuclear phosphoprotein, but there is growing evidence that YY1 expression can be dynamically regulated, including by compounds in therapeutic use. For example, YY1 and NF-κB expression are diminished in B cells by Rituximab, which is an anti-CD20 antibody used for treating B cell non-Hodgkin's lymphoma (Bonavida, "Rituximab-Induced Inhibition of Antiapoptotic Cell Survival Pathways: Implications in Chemo/Immunoresistance, Rituximab, Unresponsiveness, Prognostic and Novel Therapeutic Interventions," *Oncogene* 26(25):3629-36 (2007), which is hereby incorporated by reference in its entirety). Nitric oxide (NO) can also inhibit YY1 expression in human tumor cells (Hongo et al., "Inhibition of the Transcription Factor Yin Yang 1 Activity by S-Nitrosation," *Biochem. Biophys. Res. Commun.* 336(2):692-701 (2005), which is hereby incorporated by reference in its entirety) as well as in lung fibroblasts, which may explain some of the therapeutic benefits of inhaled NO in lung fibrosis (Yung et al., "Outpatient Inhaled Nitric Oxide in a Patient with Idiopathic Pulmonary Fibrosis: A Bridge to Lung Transplantation," *J. Heart Lung Transplant.* 20(11):1224-27 (2001), which is hereby incorporated by reference in its entirety).

Example 25

Dominant Negative YY-1 Protein Represses α-SMA Promoter Activity

Figure 20:
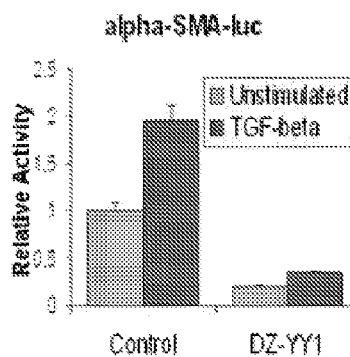
FIG. 20 is a graph showing the relative α-SMA promoter activity in W138 fibroblasts expressing the dominant negative YY-1 protein DZ-YY1. DZ-YY1 is deficient in the four zinc finger domains of YY-1 that mediate its binding to DNA. α-SMA promoter activity in cells dually transfected with the α-SMA promoter luciferase reporter construct (alpha-SMA-luc) and the DZ-YY1 construct (DZ-YY1) was attenuated compared to cells transfected with the α-SMA promoter construct alone (control). TGF-β (TGF-beta) induced α-SMA promoter activity was also significantly reduced in cells transfected with the DZ-YY1 construct compared to unstimulated control.

YY-1 binds to its core consensus sequence, 5'-CCAT-3', using a C-terminal zinc finger DNA binding domain (DBD). A YY-1 DBD mutant lacking the four zinc finger domains that no longer binds DNA (DZ-YY1) was constructed and its capacity to interfere with YY-1 transcriptional activity was assessed. As demonstrated in FIG. 20, DZ-YY1 represses basal and TGF-β induced α-SMA promoter activity in vitro. These data show that an intact YY-1 DBD is essential for transacting effects of YY1.

Example 26

H3K27 Trimethylation is Enhanced in Lung Pulmonary Fibrosis

In addition to directly regulating gene expression at the transcriptional level, YY1 is intimately involved in chromatin remodeling and epigenetic imprinting. For example, YY1 can recruit histone H4-specific methyltransferases to its target promoters (Rezai-Zadeh et al., "Targeted Recruitment of a Histone H4-Specific Methyltransferase by the Transcription Factor YY1," *Genes Dev.* 17(8):1019-29 (2003), which is hereby incorporated by reference in its entirety), and together with Polycomb group family members generates high levels of H3-K27 trimethylation needed to maintain a repressed chromatin state (Caretti et al., "The Polycomb Ezh2 Methyltransferase Regulates Muscle Gene Expression and Skeletal Muscle Differentiation," *Genes. Dev.* 18(21):2627-38 (2004); van Leenders et al., "Polycomb-Group Oncogenes EZH2, BMI1, and RING1 Are Overexpressed in Prostate Cancer with Adverse Pathologic and Clinical Features," *Eur. Urol.* 52(2):455-63 (2007); Nekrasov et al., "Pcl-PRC2 Is Needed to Generate High Levels of H3-K27 Trimethylation at Polycomb Target Genes," *Embo. J.* 26(18):4078-88 (2007), each of which is hereby incorporated by reference in its entirety).

Figures 21A, 21B:
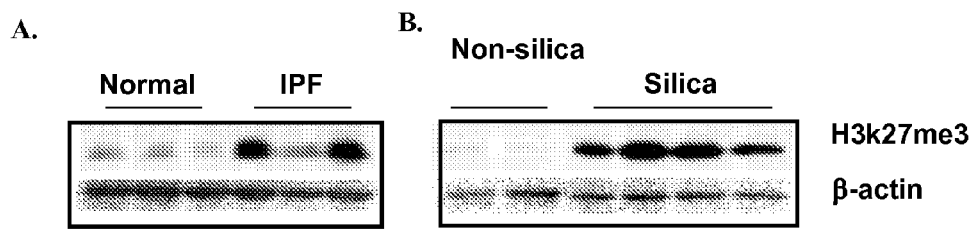
FIGS. 21A-21B are western blots showing the detection of histone-3 (H3) lysine 27 (K27) trimethylation (H3K27me3) in lung tissue samples derived from patients having idiopathic pulmonary fibrosis (IPF) and healthy control individuals (Normal) (FIG. 21A), and H3K27 trimethylation in lung tissue samples derived from silica treated (silica-induced fibrosis) and non-treated (non-silica) mice (FIG. 21B). β-actin was used a loading control.
Figure 22:
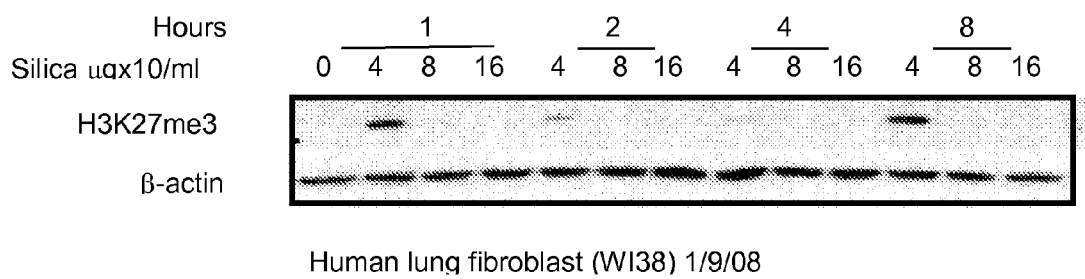
FIG. 22 is a western blot showing the time- and dose-related increase in H3K27 trimethylation (H3K27me3) in human lung fibroblasts following silica exposure at the indicated time points. β-action was used as a loading control.

The level of H3K27 trimethylation was investigated in lung tissues derived from human patients having IPF and compared to that of normal human lung tissue. FIG. 21A is a western blot of lung tissue samples showing the increase in H3 trimethylation in IPF lung samples compared to normal healthy lung tissue. As shown in FIG. 21B, an increase in H3K27 methylation was also observed in lung tissue from mice intratracheally exposed to silica. Time course and dose dependent in vivo silica exposures in mice show an increase in H3 trimethylation at low dose (4 ug) of silica at all timepoints tested, as shown in FIG. 22.

Figure 23:
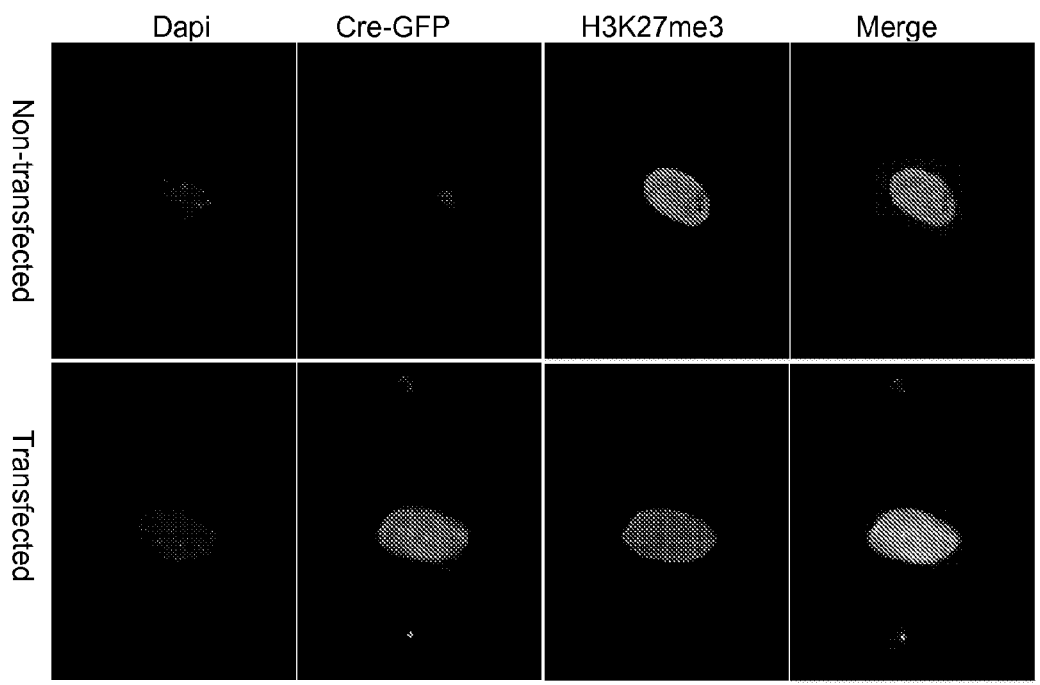
FIG. 23 shows H3K27 trimethylation (H3K27me3) in non-transfected lung fibroblasts from YY1$^{f/f}$ mice (non-transfected) or lung fibroblasts from YY1$^{f/f}$ mice transfected (transfected) with a Cre-recombinase-GFP fusion protein (Cre-GFP). Successful transfection is indicated by GFP (green) fluorescence of the Cre-GFP construct. H3K27 trimethylation was detected using an anti-H3K27 antibody and visualized by red fluorescence (H3K27me3). Nuclear staining is shown by Dapi staining Merged images (Merged) are also shown. Upon transfection of the fibroblasts with cre-recombinase, YY-1 expression was knocked down and a decrease in H3K27 methylation was observed compared to the non-transfected fibroblasts.

H3K27 trimethylation is, in part, mediated by YY-1 expression, as shown in FIG. 23. Lung fibroblasts isolated from YY1$^{f/f}$ mice were transfected with Cre-recombinase-GFP fusion protein to attenuate YY-1 expression and H3K27 trimethylation was assessed using fluorescence immunocytochemistry. Non-transfected cells, expressing normal levels of YY-1 protein, have a higher level of H3K27 trimethylation than transfected cells.

Example 27

EZH2 Expression is Enhanced in Lung Pulmonary Fibrosis

Figure 24:
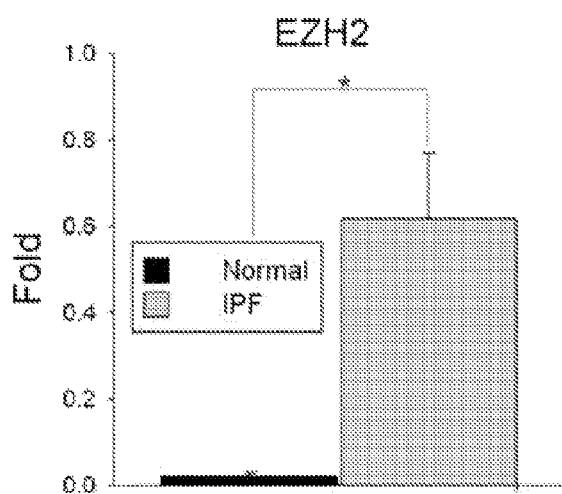
FIG. 24 is a graph showing the relative fold induction of EZH2 mRNA expression in lung tissue derived from patients having idiopathic pulmonary fibrosis (IPF) compared to healthy control individuals (Normal).

To investigate the relevance of EZH2 expression in lung pulmonary fibrosis, the EZH2 mRNA expression level was determined in IPF lung samples and normal healthy lung samples. FIG. 24 shows a four-fold induction of EZH2 expression in IPF lung samples compared to its expression in healthy lung samples.

Example 28

Use of DZ-YY1 to Inhibit Fibrosis

Because DZ-YY1 has "dominant negative" activity on α-SMA promoter activity, its therapeutic potential for inhibiting silica dependent fibroblast activation in vitro and silica induced fibrosis in vivo will be investigated.

WI-38 fibroblasts will be grown to 70-80% confluence and transfected by electroporation (300 volts, 1050 capacitance) with the α-SMA luciferase reporter with or without pSG5 DZ-YY1 (1-6 µg) or empty vector control. After recovery for 16 hours, cells will be transferred to 1% serum for 12 hours, and then stimulated with Crystalline silica (1, 10, 20, 40 µg/ml) for 6, 12, 24, and 48 hours followed by analysis of α-SMA promoter activity by luminescence. Renilla luciferase will be co-transfected as internal control for transfection efficiency and results will be expressed both as raw RLU and also relative to renilla luciferase. A separate aliquot of cells will be lysed and used to evaluate YY-1 and α-SMA protein expression and RNA expression.

Figure 25:
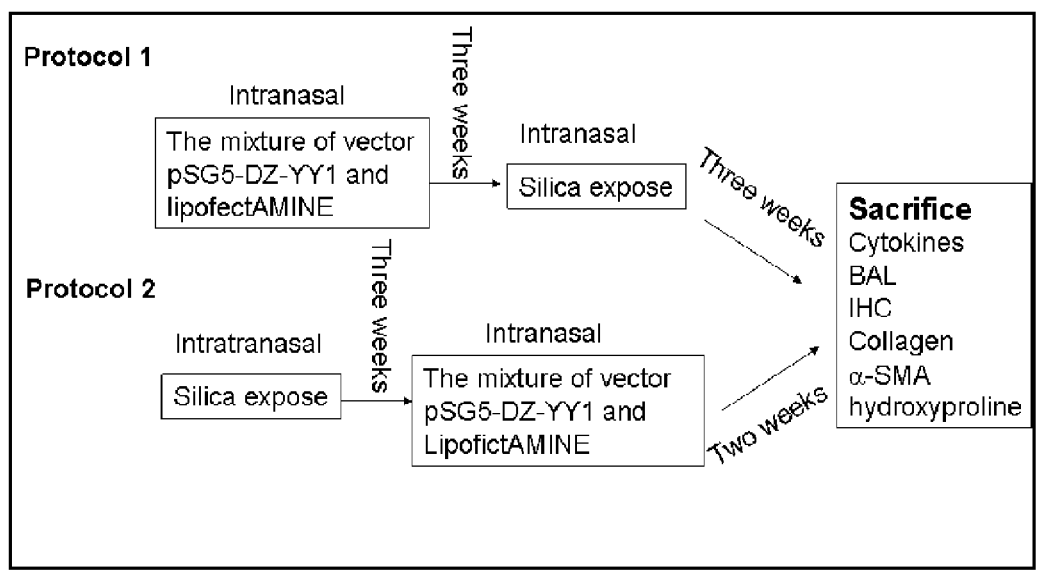
FIG. 25 is a schematic diagram outlining the in vivo study protocols for investigating the therapeutic potential of DZ-YY1 in the prevention and treatment of silica-induced lung fibrosis.

For in vivo studies using DZ-YY1, C57BL/6 wild-type mice will be exposed intranasally to silica either before or after DZ-YY1 administration (see FIG. 25). Using this approach, whether DZ-YY1 can prevent or reverse fibrosis will be determined. A 4:1 molar ratio of DZ-YY1 with transfection reagents LipofectAMINE or DOTAP (N-[1-(2,3-dioleoyl)propyl]-N,N,N-trimethylammonium methylsulfate) will be prepared to form DNA-liposome complexes (Invitrogen Life Technologies and Boehringer Mannheim, respectively). Complexes will be prepared in distilled water and incubated for 10 minutes before being administered to anesthetized mice as follows. Ketamine and xylazine (80-100 mg/kg plus 10 mg/kg, respectively) will be administered intraperitoneally and mice placed onto heated boards in the supine position. Mice will be administered 100 µg plasmid DNA-liposome complex in 60 µl final volume, followed by recovery at a 45° angle to ensure aspiration. This is essentially identical to the silica protocol. Control groups will receive equal amounts of sterile saline, or transfection reagent plus empty vector pSG5. All plasmids will be prepared using endotoxin-free columns, and incubated at 30° C. for 20 minutes prior to injection. To determine whether DZ-YY1 administration can prevent silica induced fibrosis, mice will be administered three weekly treatments of DZ-YY1 beginning one week prior to silica and then weekly for two weeks followed by sacrifice at three weeks. To determine whether DZ-YY1 administration can reverse the formation of fibrosis, mice will be administered three weekly treatments of DZ-YY1 beginning three weeks after silica exposure followed by sacrifice at six weeks. At time of sacrifice, bronchial-alveolar lavage (BAL) will be harvested for cell count analysis and production of cytokines and chemokines in BAL supernatant using bead array technology. Lungs will be perfused with PBS, fixed in 10% formaldehyde, and processed for histochemical analysis using H&E staining, Masson's trichrome, and α-SMA expression. One lung lobe will be removed and homogenized with PBS for measuring collagen, α-SMA, and hydroxyproline using western blot and ELISA.

It is expected that the dominant negative DZ-YY1 protein will compete with endogenous YY1 protein, decreasing YY-1 activities related to cell cycle progression, cell proliferation, and chromatin remodeling.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method of treating a subject having a pulmonary fibrotic condition, said method comprising:
   administering to the subject an agent that inhibits or reduces trimethylation at lysine residue 27 of histone-3 under conditions effective to treat a pulmonary fibrotic condition in the subject, wherein the agent is an EZH2 inhibitor.

2. The method according to claim 1 further comprising: selecting a subject having a pulmonary fibrotic condition before said administering.

3. The method according to claim 1, wherein said pulmonary fibrotic condition is ideopathic pulmonary fibrosis.

4. The method according to claim 1, wherein a pharmaceutical formulation containing the agent is administered.

5. The method according to claim 4, wherein the pharmaceutical composition comprises:
   a pharmaceutically acceptable delivery vehicle; and
   an effective amount of the agent.

* * * * *